(12) United States Patent
Atwell et al.

(10) Patent No.: US 11,891,441 B2
(45) Date of Patent: Feb. 6, 2024

(54) HUMAN INTERLEUKIN-4 RECEPTOR ALPHA ANTIBODIES

(71) Applicant: Eli Lilly and Company, Indianapolis, IN (US)

(72) Inventors: Shane Krummen Atwell, Carlsbad, CA (US); Yiqing Feng, Carmel, IN (US); Maya Rachel Karta, San Diego, CA (US); Donmienne Leung, San Diego, CA (US); Songqing Na, San Diego, CA (US); Diana Isabel Ruiz, San Diego, CA (US); David John Stokell, Indianapolis, IN (US); Laura Anne Pelletier, San Diego, CA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 17/817,754

(22) Filed: Aug. 5, 2022

(65) Prior Publication Data
US 2023/0064378 A1     Mar. 2, 2023

Related U.S. Application Data

(60) Provisional application No. 63/348,388, filed on Jun. 2, 2022, provisional application No. 63/229,836, filed on Aug. 5, 2021.

(51) Int. Cl.
| | |
|---|---|
| *C07K 16/24* | (2006.01) |
| *A61K 47/68* | (2017.01) |
| *A61P 35/00* | (2006.01) |
| *C07K 16/06* | (2006.01) |
| *C12N 15/85* | (2006.01) |

(52) U.S. Cl.
CPC ........ C07K 16/247 (2013.01); A61K 47/6803 (2017.08); A61P 35/00 (2018.01); C07K 16/06 (2013.01); *C07K 2317/21* (2013.01); *C07K 2317/52* (2013.01); *C07K 2317/565* (2013.01); *C12N 2015/8518* (2013.01)

(58) Field of Classification Search
CPC .. C07K 16/247; C07K 16/06; C07K 2317/21; C07K 2317/52; C07K 2317/565; C07K 2317/34; C07K 2317/732; C07K 2317/734; C07K 2317/76; C07K 2317/92; C07K 16/2866; A61K 47/6803; A61P 35/00; C12N 2015/8518
See application file for complete search history.

(56) References Cited

U.S. PATENT DOCUMENTS

| | | | |
|---|---|---|---|
| 2008/0160035 A1* | 7/2008 | Stevens | A61P 37/00 435/69.6 |
| 2009/0202568 A1* | 8/2009 | Eriksson | A61P 11/06 536/23.53 |
| 2013/0336978 A1 | 12/2013 | Eriksson et al. | |

FOREIGN PATENT DOCUMENTS

| | | |
|---|---|---|
| WO | 2018/232088 A1 | 12/2018 |
| WO | 2020/048312 A1 | 3/2020 |
| WO | 2020/135471 A1 | 7/2020 |

OTHER PUBLICATIONS

D M Paton: "Dupilumab: human monoclonal antibody against IL-4Ralpha for moderate to severe atopic dermatitis", Drugs Today, Sep. 1, 2017, vol. 53, No. 9, pp. 477-487.
Kim Jung-Eun et al: "Engineering of anti-human interleukin-4 receptor alpha antibodies with potent antagonistic activity", Scientific Reports, Dec. 1, 2019, vol. 9, No. 1, Retrieved from the internet: URL: https://www.ncbi.nlm.nih.gov/pmc/articles/PMC6533264/pdf/41598_2019_Article_44253.pdf>.
Hershey, G.K.; et al. "The association of atopy with a gain-of-function mutation in the alpha subunit of the interleukin-4 receptor" N. Engl. J. Med. 1997, 337 (24), 1720-1725.
Junttila, I. "Tuning the Cytokine Responses: An Update on Interleukin (IL)-4 and IL-13 Receptor Complexes" Frontiers in Immunology 2018, 9:888.
Labrijn, A.F.; et al. "Therapeutic IgG4 antibodies engage in Fab-arm exchange with endogenous human IgG4 in vivo." Nat. Biotechnol. 2009, 27(8):767.
Le Floc'h, A.; et al. "Dual Blockade of IL- and IL-13 with dupilumab, an IL-4Rα antibody, is required to broadly inhibit type 2 inflammation." Allergy 2020, 75, 1188-1204.
Suzuki, A.; et al. "Targeting of IL-4 and IL-13 receptors for cancer therapy" Cytokine 2015, 75(1), 79-88.

\* cited by examiner

*Primary Examiner* — Nelson B Moseley, II
*Assistant Examiner* — Alyssa Rae Stonebraker
(74) *Attorney, Agent, or Firm* — Dipa Patel

(57) ABSTRACT

The present disclosure relates to antibodies that specifically bind human IL-4Rα, compositions comprising such IL-4Rα antibodies, and methods of using such IL-4Rα antibodies.

69 Claims, 17 Drawing Sheets

Specification includes a Sequence Listing.

Binding affinity of exemplified IL-4Rα antibodies to human IL-4Rα

Binding affinity of exemplified IL-4Ra antibodies to cynomolgus monkey IL-4Ra

IL-4 blocking activity by exemplified IL-4Rα antibodies in HEK-Blue cells

IL-13 blocking activity by exemplified IL-4Rα antibodies in HEK-Blue cells

Inhibition of IL-13 induced pSTAT6 phosphorylation in human B cells

DSC thermogram of exemplifed IL-4Rα antibodies

DSC thermogram of exemplifed IL-4Rα antibodies

SEQUENCE LISTING

```
Sequence total quantity: 53
SEQ ID NO: 1            moltype = AA  length = 13
FEATURE                 Location/Qualifiers
source                  1..13
                        mol_type = protein
                        organism = synthetic construct
SEQUENCE: 1
VASGFTFSHS SMN                                                   13

SEQ ID NO: 2            moltype = AA  length = 10
FEATURE                 Location/Qualifiers
source                  1..10
                        mol_type = protein
                        organism = synthetic construct
SEQUENCE: 2
YISRATGAVY                                                       10

SEQ ID NO: 3            moltype = AA  length = 8
FEATURE                 Location/Qualifiers
source                  1..8
                        mol_type = protein
                        organism = synthetic construct
SEQUENCE: 3
AREPVFDY                                                          8

SEQ ID NO: 4            moltype = AA  length = 11
FEATURE                 Location/Qualifiers
source                  1..11
                        mol_type = protein
                        organism = synthetic construct
SEQUENCE: 4
RASQDISNYL A                                                     11

SEQ ID NO: 5            moltype = AA  length = 8
FEATURE                 Location/Qualifiers
source                  1..8
                        mol_type = protein
                        organism = synthetic construct
SEQUENCE: 5
YAASSLQS                                                          8
```

```
SEQ ID NO: 6            moltype = AA   length = 9
FEATURE                 Location/Qualifiers
source                  1..9
                        mol_type = protein
                        organism = synthetic construct
SEQUENCE: 6
LQWSSYPRT                                                                 9

SEQ ID NO: 7            moltype = AA   length = 115
FEATURE                 Location/Qualifiers
source                  1..115
                        mol_type = protein
                        organism = synthetic construct
SEQUENCE: 7
QVQLVESGGG LVQPGGSLRL SCVASGFTFS HSSMNWVRQA PGKGLEWVSY ISRATGAVYY          60
ADSVKGRFTI SRDNAKNSLY LQMNSLRDED TAVYYCAREP VFDYWGQGTL VTVSS              115

SEQ ID NO: 8            moltype = AA   length = 107
FEATURE                 Location/Qualifiers
source                  1..107
                        mol_type = protein
                        organism = synthetic construct
SEQUENCE: 8
DIQMTQSPSA MSASVGDRVT ITCRASQDIS NYLAWFQQKP GKVPTRLIYA ASSLQSGVPS          60
RFSGSGSGTE FTLTISSLQP EDFATYYCLQ WSSYPRTFGQ GTKVEIK                       107

SEQ ID NO: 9            moltype = AA   length = 445
FEATURE                 Location/Qualifiers
source                  1..445
                        mol_type = protein
                        organism = synthetic construct
SEQUENCE: 9
QVQLVESGGG LVQPGGSLRL SCVASGFTFS HSSMNWVRQA PGKGLEWVSY ISRATGAVYY          60
ADSVKGRFTI SRDNAKNSLY LQMNSLRDED TAVYYCAREP VFDYWGQGTL VTVSSASTKG         120
PCVFPLAPSS KSTSGGTAAL GCLVKDYFPE PVTVSWNSGA LTSGVHTFPA VLQSSGLYSL         180
SSVVTVPSSS LGTQTYICNV NHKPSNTKVD KRVEPKSCDK THTCPPCPAP ELLGGPSVFL         240
FPPKPKDTLM ISRTPEVTCV VVDVSHEDPE VKFNWYVDGV EVHNAKTKPR EEQYNSTYRV         300
VSVLTVLHQD WLNGKEYKCA VSNKALPAPI EKTISKAKGQ PREPQVYTLP PSREEMTKNQ         360
VSLTCLVKGF YPSDICVEWE SNGQPENNYK TTPPVLDSDG SFFLYSKLTV DKSRWQQGNV         420
FSCSVMHEAL HNHYTQKSLS LSPGK                                              445

SEQ ID NO: 10           moltype = AA   length = 214
FEATURE                 Location/Qualifiers
source                  1..214
                        mol_type = protein
                        organism = synthetic construct
SEQUENCE: 10
DIQMTQSPSA MSASVGDRVT ITCRASQDIS NYLAWFQQKP GKVPTRLIYA ASSLQSGVPS          60
RFSGSGSGTE FTLTISSLQP EDFATYYCLQ WSSYPRTFGQ GTKVEIKRTV AAPSVFIFPP         120
SDEQLKSGTA SVVCLLNNFY PREAKVQWKV DNALQSGNSQ ESVTEQDSKD STYSLSSTLT         180
LSKADYEKHK VYACEVTHQG LSSPVTKSFN RGEC                                    214

SEQ ID NO: 11           moltype = DNA   length = 1335
FEATURE                 Location/Qualifiers
source                  1..1335
                        mol_type = other DNA
                        organism = synthetic construct
SEQUENCE: 11
caggtacagc tggtggagtc tgggggaggc ttggtacagc ctgggggtc cctgagactc           60
tcctgtgtcg cctctggatt caccttcagt cattctagca tgaactgggt ccgccaggct         120
ccagggaagg ggctggagtg ggtttcatac attagtcgtg ctactggtgc cgtctactac         180
gcagactctg taaagggccg attcaccatc tccagagata tgccaaaaa ctcactgtat          240
ctgcaaatga acagcctgag agacgaggac acggctgtgt attactgtgc gagagagccg         300
gttttttgact actggggcca gggaaccctg gtcaccgtct cctcagctag caccaagggc        360
ccatgcgtct tcccctggc accctcctcc aagagcacct ctgggggcac agcggccctg          420
ggctgcctg tcaaggacta cttccccgaa ccggtgacgg tgtcgtggaa ctcaggcgca          480
ctgaccagcg gcgtgcacac cttcccggct gtcctacagt cctcaggact ctactccctc         540
agcagcgtgg tgaccgtgcc ctccagcagc ttgggcaccc agacctacat ctgcaacgtg         600
aatcacaagc ccagcaacac caaggtggac aagagagttg agcccaaatc ttgtgacaaa         660
actcacacat gcccaccgtg cccagcacct gaactcctgg ggggaccgtc agtcttcctc         720
ttccccccaa aacccaagga caccctcatg atctcccgga cccctgaggt cacatgcgtg         780
gtggtggacg tgagccacga agaccctgag gtcaagttca actggtatgt ggacggcgtg         840
gaggtgcata atgccaagac aaagccgcgg gaggagcagt acaacagcac gtaccgtgtg         900
gtcagcgtcc tcaccgtcct gcaccaagac tggctgaatg caaggagta caagtgcgcc          960
gtctccaaca agcccctccc agcccccatc gagaaaacca tctccaaagc caagggcag         1020
cccccgagaac cacaggtgta caccctgccc catcccggg aggagatgac caagaaccaa        1080
gtcagcctga cctgcctggt caaaggcttc tatcccagcg acatcgccgt ggagtgggag        1140
agcaatgggc agccggagaa caactacaag accacgcctc ccgtgctgga ctccgacggc       1200
```

```
tccttcttcc tctattccaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gcaaa                                                    1335

SEQ ID NO: 12          moltype = DNA  length = 642
FEATURE                Location/Qualifiers
source                 1..642
                       mol_type = other DNA
                       organism = synthetic construct
SEQUENCE: 12
gacatccaga tgacccagtc tccatctgcc atgtctgcat ctgtgggaga cagagtcacc    60
atcacttgtc gggcgagtca ggacattagc aattatttag cctggtttca gcagaaacca   120
gggaaagtcc ctacgcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag tggccagtt accctcggac gttcggccaa   300
gggaccaagg tggaaatcaa acggaccgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gc                      642

SEQ ID NO: 13          moltype = AA  length = 441
FEATURE                Location/Qualifiers
source                 1..441
                       mol_type = protein
                       organism = synthetic construct
SEQUENCE: 13
QVQLVESGGG LVQPGGSLRL SCVASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSSASTKG   120
PCVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVKF NWYVDGVEVH NAKTKPREEQ FNSTYRVVSV   300
LTVLHQDWLN GKEYKCKVSN KGLPSSIEKT ISKAKGQPRE PQVYTLPPSR EEMTKNQVSL   360
TCLVKGFYPS DICVEWESNG QPENNYKTTP PVLDSDGSFF LYSRLTVDKS RWQQGNVFSC   420
SVMHEALHNH YTQKSLSLSL G                                             441

SEQ ID NO: 14          moltype = DNA  length = 1323
FEATURE                Location/Qualifiers
source                 1..1323
                       mol_type = other DNA
                       organism = synthetic construct
SEQUENCE: 14
caggtacagc tggtggagtc tggggggaggc ttggtacagc ctgggggtc cctgagactc     60
tcctgtgtcg cctctggatt caccttcagt cattctagca tgaactgggt ccgccaggct   120
ccagggaagg ggctggagtg ggtttcatac attagtcgta ctggtgctgc cgtctactac   180
gcagactctg taaagggccg attcaccatc tccagagata atgccaaaaa ctcactgtat   240
ctgcaaatga acagcctgag agacgaggac acggctgtgt attactgtgc gagagagccg   300
gttttttgact actggggcca gggaaccctg gtcaccgtct cctcagcctc caccaagggc   360
ccatgcgtct tcccgctagc gccctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcacga gacctacac tgcaacgta   600
gatcacaagc ccagcaacac caaggtggac aagagagttg agtccaaata tggtccccca   660
tgcccaccct gcccagcacc tgagttcctg ggggaccat cagtcttcct gttcccccca   720
aaacccaagg acactctcat gatctcccgg accccctgag gtcacgtgcg tggtggtgac   780
gtgagccagg aagaccccga ggtcaagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaggca gccccgagag   1020
ccacaggtgt acaccctgcc cccatcccga gaggagatga ccaagaacca ggtcagcctg   1080
acctgcctgg tcaaaggctt ctaccccagc gacatcgccg tggagtggga aagcaatggg   1140
cagccggaga caactacaa gaccacgcct cccgtgctgg actccgacgg ctccttcttc   1200
ctctacagca ggctaaccgt ggacaagagc aggtggcagc aggggaatgt cttctcatgc   1260
tccgtgatgc atgaggctct gcacaaccac tacacacaga gagcctctc cctgtctctg   1320
ggt                                                                1323

SEQ ID NO: 15          moltype = AA  length = 207
FEATURE                Location/Qualifiers
source                 1..207
                       mol_type = protein
                       organism = Homo sapiens
SEQUENCE: 15
MKVLQEPTCV SDYMSISTCE WKMNGPTNCS TELRLLYQLV FLLSEAHTCI PENNGGAGCV    60
CHLLMDDVVS ADNYTLDLWA GQQLLWKGSF KPSEHVKPRA PGNLTVHTNV SDTLLLTWSN   120
PYPPDNYLYN HLTYAVNIWS ENDPADFRIY NVTYLEPSLR IAASTLKSGI SYRARVRAWA   180
QCYNTTWSEW SPSTKWHNSY REPFEQH                                       207
```

```
SEQ ID NO: 16           moltype = AA   length = 207
FEATURE                 Location/Qualifiers
source                  1..207
                        mol_type = protein
                        organism = Macaca fascicularis
SEQUENCE: 16
MKVLQEPTCV SDYMSISTCE WKMGGPTNCS AELRLLYQLV FQSSETHTCV PENNGGVGCV    60
CHLLMDDVVS MDNYTLDLWA GQQLLWKGSF KPSEHVKPRA PGNLTVHTNV SDTVLLTWSN   120
PYPPDNYLYN DLTYAVNIWS ENDPAYSRIH NVTYLKPTLR IPASTLKSGI SYRARVRAWA   180
QHYNTTWSEW SPSTKWYNSY REPFEQR                                      207

SEQ ID NO: 17           moltype = AA   length = 153
FEATURE                 Location/Qualifiers
source                  1..153
                        mol_type = protein
                        organism = Homo sapiens
SEQUENCE: 17
MGLTSQLLPP LFFLLACAGN FVHGHKCDIT LQEIIKTLNS LTEQKTLCTE LTVTDIFAAS    60
KNTTEKETFC RAATVLRQFY SHHEKDTRCL GATAQQFHRH KQLIRFLKRL DRNLWGLAGL   120
NSCPVKEANQ STLENFLERL KTIMREKYSK CSS                                153

SEQ ID NO: 18           moltype = AA   length = 146
FEATURE                 Location/Qualifiers
source                  1..146
                        mol_type = protein
                        organism = Homo sapiens
SEQUENCE: 18
MHPLLNPLLL ALGLMALLLT TVIALTCLGG FASPGPVPPS TALRELIEEL VNITQNQKAP    60
LCNGSMVWSI NLTAGMYCAA LESLINVSGC SAIEKTQRML SGFCPHKVSA GQFSSLHVRD   120
TKIEVAQFVK DLLLHLKKLF REGRFN                                       146

SEQ ID NO: 19           moltype = AA   length = 13
FEATURE                 Location/Qualifiers
source                  1..13
                        mol_type = protein
                        organism = synthetic construct
SEQUENCE: 19
AASGFTFSIS SMN                                                      13

SEQ ID NO: 20           moltype = AA   length = 10
FEATURE                 Location/Qualifiers
source                  1..10
                        mol_type = protein
                        organism = synthetic construct
SEQUENCE: 20
YISRATGAIY                                                          10

SEQ ID NO: 21           moltype =      length =
SEQUENCE: 21
000

SEQ ID NO: 22           moltype = AA   length = 11
FEATURE                 Location/Qualifiers
source                  1..11
                        mol_type = protein
                        organism = synthetic construct
SEQUENCE: 22
RASQGISNYL A                                                        11

SEQ ID NO: 23           moltype =      length =
SEQUENCE: 23
000

SEQ ID NO: 24           moltype = AA   length = 9
FEATURE                 Location/Qualifiers
source                  1..9
                        mol_type = protein
                        organism = synthetic construct
SEQUENCE: 24
LQHNSYPRT                                                            9

SEQ ID NO: 25           moltype = AA   length = 115
FEATURE                 Location/Qualifiers
source                  1..115
                        mol_type = protein
                        organism = synthetic construct
```

```
SEQUENCE: 25
QVQLVESGGG LVQPGGSLRL SCAASGFTFS ISSMNWVRQA PGKGLEWVSY ISRATGAIYY    60
ADSVKGRFTI SRNNAKNSLY LQMNSLRDED TAVYYCAREP VFDYWGQGTL VTVSS        115

SEQ ID NO: 26           moltype = AA   length = 107
FEATURE                 Location/Qualifiers
source                  1..107
                        mol_type = protein
                        organism = synthetic construct
SEQUENCE: 26
DIQMTQSPSA MSASVGDRVT ITCRASQGIS NYLAWFQQKP GKVPTRLIYA ASSLQSGVPS    60
RFSGSGSGTE FTLTISSLQP EDFATYYCLQ HNSYPRTFGQ GTKVEIK                  107

SEQ ID NO: 27           moltype = AA   length = 441
FEATURE                 Location/Qualifiers
source                  1..441
                        mol_type = protein
                        organism = synthetic construct
SEQUENCE: 27
QVQLVESGGG LVQPGGSLRL SCAASGFTFS ISSMNWVRQA PGKGLEWVSY ISRATGAIYY    60
ADSVKGRFTI SRNNAKNSLY LQMNSLRDED TAVYYCAREP VFDYWGQGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEAA GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                              441

SEQ ID NO: 28           moltype = AA   length = 214
FEATURE                 Location/Qualifiers
source                  1..214
                        mol_type = protein
                        organism = synthetic construct
SEQUENCE: 28
DIQMTQSPSA MSASVGDRVT ITCRASQGIS NYLAWFQQKP GKVPTRLIYA ASSLQSGVPS    60
RFSGSGSGTE FTLTISSLQP EDFATYYCLQ HNSYPRTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 29           moltype = DNA   length = 1323
FEATURE                 Location/Qualifiers
source                  1..1323
                        mol_type = other DNA
                        organism = synthetic construct
SEQUENCE: 29
caggtacagc tggtggagtc tgggggaggc ttggtacagc ctggggggtc cctgagactc    60
tcctgtgcag cctctggatt cacccttcag atctctagca tgaactgggt ccgccaggct    120
ccagggaagg ggctggagtg ggtttcatac attagtcgtg ctactggtgc catatactac    180
gcagactctg taaagggccg attcaccatc tccagaaaca atgccaaaaa ctcactgtat    240
ctgcaaatga acagcctgag agacgaggac acggctgtgt attactgtgc gagagagccg    300
gtttttgact actgggggca gggaacccctg gtcaccgtct cctcagcttc taccaagggc    360
ccatcggtct tccccctagc gccctgctcc aggagcacct ccgagagcac agccgccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcacga agacctacac ctgcaacgta    600
gatcacaagc ccagcaacac caaggtggac aagagagttg agtccaaata tggtccccca    660
tgcccacccc tgcccagcac ctgaggccgcc ggggggaccat cagtcttcct gttccccccca    720
aaacccaagg acactctcat gatctcccgg acccctgagg tcacgtgcgt ggtggtggac    780
gtgagccagg aagaccccga ggtccagttc aactggtacg tggatggcgt ggaggtgcat    840
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaaagggca gccccgagag    1020
ccacaggtgt acaccctgcc cccatcccag gaggagatga ccaagaacca ggtcagcctg    1080
acctgcctgg tcaaaggctt ctaccccagc gacatcgccg tggagtggga aagcaatggg    1140
cagccggaga acaactacaa gaccacgcct cccgtgctgg actccgacgg ctccttcttc    1200
ctctacagca agctaaccgt ggacaagagc aggtggcagg aggggaatgt cttctcatgc    1260
tccgtgatgc atgaggctct gcacaaccac tacacacaga gagcctctc cctgtctctg    1320
ggt                                                                  1323

SEQ ID NO: 30           moltype = DNA   length = 642
FEATURE                 Location/Qualifiers
source                  1..642
                        mol_type = other DNA
                        organism = synthetic construct
SEQUENCE: 30
gacatccaga tgacccagtc tccatctgcc atgtctgcat ctgtgggaga cagagtcacc    60
atcacttgtc gggcgagtca gggcattagc aattatttag cctggtttca gcagaaacca    120
gggaaagtcc ctacgcgcct gatctatgct gcatccagtt tgcaaagtgg ggtcccatca    180
aggttcagcg gcagtggatc tgggacagaa ttcactctca caatcagcag cctgcagcct    240
```

```
gaagattttg caacttatta ctgtctacag cataatagtt accctcggac gttcggccaa    300
gggaccaagg tggaaatcaa acgaactgtg gcgcgccat ctgtcttcat cttcccgcca     360
tctgatgagc agttgaaatc cggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg     540
ctgagcaaag cagactacga gaaacacaaa gtctacgcct gcgaagtcac ccatcagggc    600
ctgagctcgc ccgtcacaaa gagcttcaac aggggagagt gc                      642

SEQ ID NO: 31          moltype = AA   length = 441
FEATURE                Location/Qualifiers
source                 1..441
                       mol_type = protein
                       organism = synthetic construct
SEQUENCE: 31
QVQLVESGGG LVQPGGSLRL SCVASGFTFS HSSMNWVRQA PGKGLEWVSY ISRATGAVYY     60
ADSVKGRFTI SRDNAKNSLY LQMNSLRDED TAVYYCAREP VFDYWGQGTL VTVSSASTKG    120
PCVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DICVEWESNG QPENNYKTTP PVLDSDGSFF LYSRLTVDKS RWQEGNVFSC    420
SVMHEALHNH YTQKSLSLSL G                                              441

SEQ ID NO: 32          moltype = DNA   length = 1323
FEATURE                Location/Qualifiers
source                 1..1323
                       mol_type = other DNA
                       organism = synthetic construct
SEQUENCE: 32
caggtacagc tggtggagtc tgggggaggc ttggtacagc ctggggggtc cctgagactc     60
tcctgtgtcg cctctggatt caccttcagt cattctagca tgaactgggt ccgccaggct    120
ccagggaagg gctggagtg ggtttcatac attagtcgtg ctactggtgc cgtctactac     180
gcagactctg taaagggccg attcaccatc tccagagata tgccaaaaa ctcactgtat     240
ctgcaaatga acagcctgag agacgaggac acggctgtgt attactgtgc gagagagccg    300
gtttttgact actggggcca gggaaccctg gtcaccgtct cctcagcctc caccaagggc    360
ccatgcgtct tccccctagc gccctgctcc aggagcacct ccgagagcac agccgccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcacga gaccctacgc ctgcaacgta    600
gatcacaagc ccagcaacac caaggtggac aagagagttg agtccaaata tggtccccca    660
tgcccacccc tgcccagcac ctgagttcctg ggggaccat cagtcttcct gttccccca    720
aaacccaagg acactctcat gatctcccgg acccctgagg tcacgtgcgt ggtggtggac    780
gtgagccagg aagacccccga ggtccagttc aactggtacg tggatggcgt ggaggtgcac    840
aatgccaaga caaagccgcg ggaggagcag ttcaacagca cgtaccgtgt ggtcagcgtc    900
ctcaccgtcc tgcaccagga ctggctgaac ggcaaggagt acaagtgcaa ggtctccaac    960
aaaggcctcc cgtcctccat cgagaaaacc atctccaaag ccaagggca gccccgagag   1020
ccacaggtgt acaccctgcc ccatcccag gaggagatga ccaagaacca ggtcagcctg   1080
acctgcctgg tcaaaggctt ctaccccagc gacatcgcg tggagtggga aagcaatggg   1140
cagccggaga caactacaa gaccacgcct cccgtgctgg actccgacgg ctccttcttc   1200
ctctacagca ggctaaccgt ggacaagagc aggtggcagg aggggaatgt cttctcatgc   1260
tccgtgatgc atgaggctct gcacaaccac tacacacaga gagcctctc cctgtctctg   1320
ggt                                                                 1323

SEQ ID NO: 33          moltype = AA   length = 445
FEATURE                Location/Qualifiers
source                 1..445
                       mol_type = protein
                       organism = synthetic construct
SEQUENCE: 33
QVQLVESGGG LVQPGGSLRL SCVASGFTFS HSSMNWVRQA PGKGLEWVSY ISRATGAVYY     60
ADSVKGRFTI SRDNAKNSLY LQMNSLRDED TAVYYCAREP VFDYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDK THTCPPCPAP ELLGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCA VSNKALPAPI EKTISKAKGQ PREPQVYTLP PSREEMTKNQ    360
VSLTCLVKGF YPSDIAVEWE SNGQPENNYK TTPPVLDSDG SFFLYSKLTV DKSRWQQGNV    420
FSCSVMHEAL HNHYTQKSLS LSPGK                                          445

SEQ ID NO: 34          moltype = DNA   length = 1335
FEATURE                Location/Qualifiers
source                 1..1335
                       mol_type = other DNA
                       organism = synthetic construct
SEQUENCE: 34
caggtacagc tggtggagtc tgggggaggc ttggtacagc ctggggggtc cctgagactc     60
tcctgtgtcg cctctggatt caccttcagt cattctagca tgaactgggt ccgccaggct    120
ccagggaagg gctggagtg ggtttcatac attagtcgtg ctactggtgc cgtctactac     180
gcagactctg taaagggccg attcaccatc tccagagata tgccaaaaa ctcactgtat     240
ctgcaaatga acagcctgag agacgaggac acggctgtgt attactgtgc gagagagccg    300
```

```
gtttttgact actggggcca gggaaccctg gtcaccgtct cctcagctag caccaagggc   360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
ctgaccagcg gcgtgcacac cttccggct gtcctacagt cctcaggact ctactccctc    540
agcagcgtgg tgaccgtgcc ctccagcagc ttgggcaccc agacctacat ctgcaacgtg   600
aatcacaagc ccagcaacac caaggtggac aagagagttg agcccaaatc ttgtgacaaa   660
actcacacat gcccaccgtg cccagcacct gaactcctgg ggggaccgtc agtcttcctc   720
ttccccccaa aacccaagga caccctcatg atctcccgga cccctgaggt cacatgcgtg   780
gtggtggacg tgagccacga agaccctgag gtcaagttca actggtatgt ggacggcgtg   840
gaggtgcata atgccaagac aaagccgcgg gaggagcagt acaacagcac gtaccgtgtg   900
gtcagcgtcc tcaccgtcct gcaccaagac tggctgaatg gcaaggagta caagtgcgcc   960
gtctccaaca aagcccctcc cagccccatc gagaaaacca tctccaaagc caagggcag   1020
ccccgagaac cacaggtgta caccctgccc ccatcccggg aggagatgac caagaaccaa  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctattccaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gcaaa                                                   1335

SEQ ID NO: 35            moltype = AA  length = 441
FEATURE                  Location/Qualifiers
source                   1..441
                         mol_type = protein
                         organism = synthetic construct
SEQUENCE: 35
QVQLVESGGG LVQPGGSLRL SCVASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVKF NWYVDGVEVH NAKTKPREEQ FNSTYRVVSV   300
LTVLHQDWLN GKEYKCKVSN KGLPSSIEKT ISKAKGQPRE PQVYTLPPSR EEMTKNQVSL   360
TCLVKGFYPS DIAVEWESNG QPENNYKTTP PVLDSDGSFF LYSRLTVDKS RWQQGNVFSC   420
SVMHEALHNH YTQKSLSLSL G                                            441

SEQ ID NO: 36            moltype = DNA  length = 1323
FEATURE                  Location/Qualifiers
source                   1..1323
                         mol_type = other DNA
                         organism = synthetic construct
SEQUENCE: 36
caggtacagc tggtggagtc tgggggaggc ttggtacagc ctggggggtc cctgagactc    60
tcctgtgtcg cctctggatt caccttcagt cattctagca tgaactgggt ccgccaggct   120
ccagggaagg ggctggagtg ggtttcatac attagtcgta ctactggtgc cgtctactac   180
gcagactctg taaagggccg attcaccatc tccagagata tgccaaaaa ctcactgtat    240
ctgcaaatga acagcctgag agacgaggac acggctgtgt attactgtgc gagagagccc   300
gtttttgact actggggcca gggaaccctg gtcaccgtct cctcagcctc caccaagggc   360
ccatcggtct tccccctagc gccctgctcc aggagcacct ccgagagccc agcgccctg    420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcacga gacctacac ctgcaacgta    600
gatcacaagc ccagcaacac caaggtggac aagagagttg agtccaaata tggtcccca    660
tgcccaccct gcccagcacc tgagttcctg ggggaccat cagtcttcct gttccccca    720
aaacccaagg acactctcat gatctcccgg acccctgagg tcacgtgcgt ggtggtggac   780
gtgagccagg aagaccccga ggtccagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaagggca gccccgagag  1020
ccacaggtgt acaccctgcc cccatcccga gaggagatga ccaagaacca ggtcagcctg  1080
acctgcctgg tcaaaggctt ctaccccagc gacatcgccg tggagtggga aagcaatggg  1140
cagccggaga acaactacaa gaccacgcct cccgtgctgg actccgacgg ctccttcttc  1200
ctctacagca ggctaaccgt ggacaagagc aggtggcagc aggggaatgt cttctcatgc  1260
tccgtgatgc atgaggctct gcacaaccac tacacacaga agagcctctc cctgtctctg  1320
ggt                                                                1323

SEQ ID NO: 37            moltype = AA  length = 441
FEATURE                  Location/Qualifiers
source                   1..441
                         mol_type = protein
                         organism = synthetic construct
SEQUENCE: 37
QVQLVESGGG LVQPGGSLRL SCVASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL G                                            441
```

```
SEQ ID NO: 38           moltype = DNA   length = 1323
FEATURE                 Location/Qualifiers
source                  1..1323
                        mol_type = other DNA
                        organism = synthetic construct
SEQUENCE: 38
caggtacagc tggtggagtc tgggggaggc ttggtacagc ctgggggtc cctgagactc    60
tcctgtgtcg cctctggatt caccttcagt cattctagca tgaactgggt ccgccaggct   120
ccagggaagg ggctggagtg ggtttcatac attagtcgtg ctactggtgc cgtctactac   180
gcagactctg taaagggccg attcaccatc tccagagata atgccaaaaa ctcactgtat   240
ctgcaaatga acagcctgag agacgaggac acggctgtgt attactgtgc gagagagccg   300
gttttgact actggggcca gggaaccctg gtcaccgtct cctcagcctc caccaagggc   360
ccatcggtct tccccctagc gccctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcacga gacctacac ctgcaacgta   600
gatcacaagc ccagcaacac caaggtggac aagagagttg agtccaaata tggtccccca   660
tgcccaccct gcccagcacc tgagttcctg ggggaccat cagtcttcct gttccccca    720
aaacccaagg acactctcat gatctcccgg acccctgagg tcacgtgcgt ggtggtggac   780
gtgagccagg aagaccccga ggtccagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaaggca gccccgagag  1020
ccacaggtgt acaccctgcc ccatcccag gaggagatga ccaagaacca ggtcagcctg   1080
acctgcctgg tcaaaggctt ctaccccagc gacatcgccg tggagtggga aagcaatggg  1140
cagccggaga acaactacaa gaccacgcct cccgtgctgg actccgacgg ctccttcttc  1200
ctctacagca ggctaaccgt ggacaagagc aggtggcagg aggggaatgt cttctcatgc  1260
tccgtgatgc atgaggctct gcacaaccac tacacacaga gagcctctc cctgtctctg   1320
ggt                                                                 1323

SEQ ID NO: 39           moltype = AA    length = 825
FEATURE                 Location/Qualifiers
source                  1..825
                        mol_type = protein
                        organism = Homo sapiens
SEQUENCE: 39
MGWLCSGLLF PVSCLVLLQV ASSGNMKVLQ EPTCVSDYMS ISTCEWKMNG PTNCSTELRL    60
LYQLVFLLSE AHTCIPENNG GAGCVCHLLM DDVVSADNYT LDLWAGQQLL WKGSFKPSEH   120
VKPRAPGNLT VHTNVSDTLL LTWSNPYPPD NYLYNHLTYA VNIWSENDPA DFRIYNVTYL   180
EPSLRIAAST LKSGISYRAR VRAWAQCYNT TWSEWSPSTK WHNSYREPFE QHLLLGVSVS   240
CIVILAVCLL CYVSITKIKK EWWDQIPNPA RSRLVAIIIQ DAQGSQWEKR SRGQEPAKCP   300
HWKNCLTKLL PCFLEHNMKR DEDPHKAAKE MPFQGSGKSA WCPVEISKTV LWPESISVVR   360
CVELFEAPVE CEEEEEVEEE KGSFCASPES SRDDFQEGRE GIVARLTESL FLDLLGEENG   420
GFCQQDMGES CLLPPSGSTS AHMPWDEFPS AGPKEAPPWG KEQPLHLEPS PPASPTQSPD   480
NLTCTETPLV IAGNPAYRSF SNSLSQSPCP RELGPDPLLA RHLEEVEPEM PCVPQLSEPT   540
TVPQPEPETW EQILRRNVLQ HGAAAAPVSA PTSGYQEFVH AVEQGGTQAS AVVGLGPPGE   600
AGYKAFSSLL ASSAVSPEKC GFGASSGEEG YKPFQDLIPG CPGDPAPVPV PLFTFGLDRE   660
PPRSPQSSHL PSSSPEHLGL EPGEKVEDMP KPPLPQEQAT DPLVDSLGSG IVYSALTCHL   720
CGHLKQCHGQ EDGGQTPVMA SPCCGCCCGD RSSPPTTPLR APDPSPGGVP LEASLCPASL   780
APSGISEKSK SSSSFHPAPG NAQSSSQTPK IVNFVSVGPT YMRVS                   825

SEQ ID NO: 40           moltype = AA    length = 832
FEATURE                 Location/Qualifiers
source                  1..832
                        mol_type = protein
                        organism = Macaca fascicularis
SEQUENCE: 40
MGWLCSGLLF PVSCLVLLQV ASSGCSCVSP GSMKVLQEPT CVSDYMSIST CEWKMGGPTN    60
CSAELRLLYQ LVFQSSETHT CVPENNGGVG CVCHLLMDDV VSMDNYTLDL WAGQQLLWKG   120
SFKPSEHVKP RAPGNLTVHT NVSDTVLLTW SNPYPPDNYL YNDLTYAVNI WSENDPAYSR   180
IHNVTYLKPT LRIPASTLKS GISYRARVRA WAQHYNTTWS EWSPSTKWYN SYREPFEQRL   240
LWGVSAACVF ILFFCLSCYF SVTKIKKEWW DQIPNPARSH LVAIIIQDAQ ESQWEKRSRG   300
QEAAKCPYWK NCLTKLLPCF LEHNMKRDED PHKAVKDLPF RGSGKSAWCP VEISKTVLWP   360
ESISVVRCVE LFEAPVECKE EEEVEEEKGS FCTSSESNRD DFQEGREGIV ARLTESLFLD   420
LLGGENGGFF QQDMGESCLL PPLGSTSAHV PWDEFPSAGS KEVPPWGKEQ PLHQEPSPPA   480
SPTQSPDNPT CTEMPLVISS NPAYRSFSNS LSQSPCPRGL GPDPLLARHL EEVDPEMPCA   540
PQLSEPTTVA PAEPETWEQI LRRNVLQHGA AAAPASAPTS GYREFVHAVQ QGGIQASAVA   600
GLGPPGEAGY KAFSSLLASS AVSPGECGFG ASSGEEGYKP FQDLTPGCPG DPAPVPVPLF   660
TFGLDREPPH SPQSSHLPSN SPEHLALEPG EKVEDMQKPP LPPEQATDPL GDSLGSGIVY   720
SALTCHLCGH LKQCHGQEDG GQAPVVASPC CGCCCGDRSS PPTTPLRAPD PSLGGVPLEA   780
SLCPASLAPS GISEKSKSSL SFHPAPGSAQ SSSQTPQIVN FVSVGPTCMR VS            832

SEQ ID NO: 41           moltype = AA    length = 321
FEATURE                 Location/Qualifiers
source                  1..321
                        mol_type = protein
                        organism = Homo sapiens
```

```
SEQUENCE: 41
MEEGQYSEIE ELPRRRCCRR GTQIVLLGLV TAALWAGLLT LLLLWHWDTT QSLKQLEERA    60
ARNVSQVSKN LESHHGDQMA QKSQSTQISQ ELEELRAEQQ RLKSQDLELS WNLNGLQADL   120
SSFKSQELNE RNEASDLLER LREEVTKLRM ELQVSSGFVC NTCPEKWINF QRKCYYFGKG   180
TKQWVHARYA CDDMEGQLVS IHSPEEQDFL TKHASHTGSW IGLRNLDLKG EFIWVDGSHV   240
DYSNWAPGEP TSRSQGEDCV MMRGSGRWND AFCDRKLGAW VCDRLATCTP PASEGSAESM   300
GPDSRPDPDG RLPTPSAPLH S                                            321

SEQ ID NO: 42         moltype = AA  length = 13
FEATURE               Location/Qualifiers
source                1..13
                      mol_type = protein
                      organism = synthetic construct
SEQUENCE: 42
AASGFTFSHS SMN                                                      13

SEQ ID NO: 43         moltype =     length =
SEQUENCE: 43
000

SEQ ID NO: 44         moltype = AA  length = 115
FEATURE               Location/Qualifiers
source                1..115
                      mol_type = protein
                      organism = synthetic construct
SEQUENCE: 44
QVQLVESGGG LVQPGGSLRL SCAASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSS        115

SEQ ID NO: 45         moltype = AA  length = 107
FEATURE               Location/Qualifiers
source                1..107
                      mol_type = protein
                      organism = synthetic construct
SEQUENCE: 45
DIQMTQSPSA MSASVGDRVT ITCRASQGIS NYLAWFQQKP GKVPTRLIYA ASSLQSGVPS    60
RFSGSGSGTE FTLTISSLQP EDFATYYCLQ WSSYPRTFGQ GTKVEIK                 107

SEQ ID NO: 46         moltype = AA  length = 441
FEATURE               Location/Qualifiers
source                1..441
                      mol_type = protein
                      organism = synthetic construct
SEQUENCE: 46
QVQLVESGGG LVQPGGSLRL SCAASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSSASTKG   120
PCVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DICVEWESNG QPENNYKTTP PVLDSDGSFF LYSRLTVDKS RWQEGNVFSC   420
SVMHEALHNH YTQKSLSLSL G                                            441

SEQ ID NO: 47         moltype = AA  length = 214
FEATURE               Location/Qualifiers
source                1..214
                      mol_type = protein
                      organism = synthetic construct
SEQUENCE: 47
DIQMTQSPSA MSASVGDRVT ITCRASQGIS NYLAWFQQKP GKVPTRLIYA ASSLQSGVPS    60
RFSGSGSGTE FTLTISSLQP EDFATYYCLQ WSSYPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 48         moltype = DNA  length = 1323
FEATURE               Location/Qualifiers
source                1..1323
                      mol_type = other DNA
                      organism = synthetic construct
SEQUENCE: 48
caggtacagc tggtggagtc tgggggaggc ttggtacagc ctggggggtc cctgagactc    60
tcctgtgcag cctctggatt caccttcagt cattctagca tgaactgggt ccgccaggct   120
ccagggaagg ggctggagtg ggtttcatac attagtcgtg ctactggtgc cgtctactac   180
gcagactctg taaagggccg attcaccatc tccagagata atgccaaaaa ctcactgtat   240
ctgcaaatga acagcctgag agacgaggac acggctgtgt attactgtgc gagagagccg   300
gtttttgact actggggcca gggaaccctg gtcaccgtct cctcagcctc caccaagggc   360
ccatgcgtct tccgctagc gcctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
```

```
agcagcgtgg tgaccgtgcc ctccagcagc ttgggcacga agacctacac ctgcaacgta  600
gatcacaagc ccagcaacac caaggtggac aagagagttg agtccaaata tggtccccca  660
tgcccaccct gcccagcacc tgagttcctg gggggaccat cagtcttcct gttcccccca  720
aaacccaagg acactctcat gatctcccgg acccctgagg tcacgtgcgt ggtggtggac  780
gtgagccagg aagaccccga ggtccagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag 1020
ccacaggtgt acaccctgcc cccatcccag gaggagatga ccaagaacca ggtcagcctg 1080
acctgcctgg tcaaaggctt ctaccccagc gacatctgcg tggagtggga aagcaatggg 1140
cagccggaga acaactacaa gaccacgcct cccgtgctgg actccgacgg ctccttcttc 1200
ctctacagca ggctaaccgt ggacaagagc aggtggcagg aggggaatgt cttctcatgc 1260
tccgtgatgc atgaggctct gcacaaccac tacacacaga gagcctctcc ctgtctctg  1320
ggt                                                              1323

SEQ ID NO: 49          moltype = DNA   length = 642
FEATURE                Location/Qualifiers
source                 1..642
                       mol_type = other DNA
                       organism = synthetic construct
SEQUENCE: 49
gacatccaga tgacccagtc tccatctgcc atgtctgcat ctgtgggaga cagagtcacc   60
atcacttgtc gggcgagtca gggcattagc aattatttag cctggtttca gcagaaacca  120
gggaaagtcc ctacgcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag tggtccagtt accctcggac gttcggccaa  300
gggaccaagg tggaaatcaa acggaccgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gc                     642

SEQ ID NO: 50          moltype = AA   length = 441
FEATURE                Location/Qualifiers
source                 1..441
                       mol_type = protein
                       organism = synthetic construct
SEQUENCE: 50
QVQLVESGGG LVQPGGSLRL SCVASGFTFS HSSMNWVRQA PGKGLEWVSY ISRATGAVYY   60
ADSVKGRFTI SRDNAKNSLY LQMNSLRDED TAVYYCAREP VFDYWGQGTL VTVSSASTKG  120
PCVFPLAPCS RSTSGSTAAL GCLVKDYFPE PVTVSWNSGA LTSGVHTFPA VLQSSGLYSL  180
SSVVTVPSSS LGTKTYTCNV NHKPSNTKVD KRVESKYGPP CPPCPAPEFL GGPSVFLFPP  240
KPKDTLMISR TPEVTCVVVD VSQEDPEVKF NWYVDGVEVH NAKTKPREEQ FNSTYRVVSV  300
LTVLHQDWLN GKEYKCKVSN KGLPSSIEKT ISKAKGQPRE PQVYTLPPSR EEMTKNQVSL  360
TCLVKGFYPS DICVEWESNG QPENNYKTTP PVLDSDGSFF LYSRLTVDKS RWQQGNVFSC  420
SVMHEALHNH YTQKSLSLSL G                                            441

SEQ ID NO: 51          moltype = DNA   length = 1323
FEATURE                Location/Qualifiers
source                 1..1323
                       mol_type = other DNA
                       organism = synthetic construct
SEQUENCE: 51
caggtacagc tggtggagtc tgggggaggc ttggtacagc ctgggggtc cctgagactc    60
tcctgtgtcg cctctggatt caccttcagt cattctagca tgaactgggt ccgccaggct  120
ccagggaagg ggctggagtg ggtttcatac attagtcgtg ctactggtgc cgtctactac  180
gcagactctg taaagggccg attcaccatc tccagagata tgccaaaaa ctcactgtat  240
ctgcaaatga acagcctgag agacgaggac acggctgtgt attactgtgc gagagagccg  300
gtttttgact actgggccca gggaaccctg gtcaccgtct cctcagcctc caccaagggc  360
ccatcgcgtc tccccgctag ccctctgctc caggagcacct ccggcagcac agccgccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcacga agacctacac ctgcaacgta  600
aaccacaagc ccagcaacac caaggtggac aagagagttg agtccaaata tggtccccca  660
tgcccaccct gcccagcacc tgagttcctg gggggaccat cagtcttcct gttcccccca  720
aaacccaagg acactctcat gatctcccgg acccctgagg tcacgtgcgt ggtggtggac  780
gtgagccagg aagaccccga ggtcaagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag 1020
ccacaggtgt acaccctgcc cccatcccga gaggagatga ccaagaacca ggtcagcctg 1080
acctgcctgg tcaaaggctt ctaccccagc gacatctgcg tggagtggga aagcaatggg 1140
cagccggaga acaactacaa gaccacgcct cccgtgctgg actccgacgg ctccttcttc 1200
ctctacagca ggctaaccgt ggacaagagc aggtggcagc aggggaatgt cttctcatgc 1260
tccgtgatgc atgaggctct gcacaaccac tacacacaga gagcctctcc ctgtctctg  1320
ggt                                                              1323
```

```
SEQ ID NO: 52          moltype = AA  length = 445
FEATURE                Location/Qualifiers
source                 1..445
                       mol_type = protein
                       organism = synthetic construct
SEQUENCE: 52
QVQLVESGGG LVQPGGSLRL SCVASGFTFS HSSMNWVRQA PGKGLEWVSY ISRATGAVYY    60
ADSVKGRFTI SRDNAKNSLY LQMNSLRDED TAVYYCAREP VFDYWGQGTL VTVSSASTKG   120
PCVFPLAPSS KSTSGGTAAL GCLVKDYFPE PVTVSWNSGA LTSGVHTFPA VLQSSGLYSL   180
SSVVTVPSSS LGTQTYICNV NHKPSNTKVD KRVEPKSCDK THTCPPCPAP EAAGGPSVFL   240
FPPKPKDTLM ISRTPEVTCV VVDVSHEDPE VKFNWYVDGV EVHNAKTKPR EEQYNSTYRV   300
VSVLTVLHQD WLNGKEYKCK VSNKALAAPI EKTISKAKGQ PREPQVYTLP PSREEMTKNQ   360
VSLTCLVKGF YPSDICVEWE SNGQPENNYK TTPPVLDSDG SFFLYSKLTV DKSRWQQGNV   420
FSCSVMHEAL HNHYTQKSLS LSPGK                                        445

SEQ ID NO: 53          moltype = DNA  length = 1335
FEATURE                Location/Qualifiers
source                 1..1335
                       mol_type = other DNA
                       organism = synthetic construct
SEQUENCE: 53
caggtacagc tggtggagtc tgggggaggc ttggtacagc ctgggggtc cctgagactc     60
tcctgtgtcg cctctggatt caccttcagt cattctagca tgaactgggt ccgccaggct   120
ccagggaagg ggctggagtg ggtttcatac attagtcgtg ctactggtgc cgtctactac   180
gcagactctg taaagggccg attcaccatc tccagagata atgccaaaaa ctcactgtat   240
ctgcaaatga acagcctgag agacgaggac acggctgtgt attactgtgc gagagagccg   300
gtttttgact actggggcca gggaaccctg gtcaccgtct cctcagctag caccaagggc   360
ccatgcgtct tccccctggc accctcctcc aagagcacct ctgggggcac agcggccctg   420
ggctgcctgg tcaaggacta cttccccgaa ccggtgacgg tgtcgtggaa ctcaggcgca   480
ctgaccagcg gcgtgcacac cttcccggct gtcctacagt cctcaggact ctactccctc   540
agcagcgtgg tgaccgtgcc ctccagcagc ttgggcaccc agacctacat ctgcaacgtg   600
aatcacaagc ccagcaacac caaggtggac aagagagttg agcccaaatc ttgtgacaaa   660
actcacacat gcccaccgtg cccagcacct gaagccgccg ggggaccgtc agtcttcctc   720
ttccccccaa aacccaagga caccctcatg atctcccgga cccctgaggt cacatgcgtg   780
gtggtggacg tgagccacga agaccctgag gtcaagttca actggtatgt ggacggcgtg   840
gaggtgcata atgccaagac aaagccgcgg gaggagcagt acaacagcac gtaccgtgtg   900
gtcagcgtcc tcaccgtcct gcaccaagac tggctgaatg gcaaggagta caagtgcaag   960
gtctccaaca aagccctcgc cgcccccatc gagaaaacca tctccaaagc caaagggcag  1020
ccccgagaac cacaggtgta caccctgccc ccatcccggg aggagatgac caagaaccag  1080
gtcagcctga cctgcctggt caaaggcttc tatcccagcg acatctgcgt ggagtgggag  1140
agcaatgggc agccggagaa caactacaag accacgcctc ccgtgctgga ctccgacggc  1200
tccttcttcc tctattccaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gcaaa                                                  1335
```

HUMAN INTERLEUKIN-4 RECEPTOR ALPHA ANTIBODIES

The present disclosure is in the field of medicine. Particularly the present disclosure relates to antibodies that specifically bind human Interleukin-4 (IL-4) receptor alpha subunit (IL-4Rα), compositions comprising such IL-4Rα antibodies, and methods of using such IL-4Rα antibodies.

The ongoing epidemic of immune inflammatory disorders such as Type 2 inflammatory diseases, such as atopic dermatitis, asthma, food allergy amongst others, represent a heterogenous set of disorders affecting different target tissues. Immunological and genetic studies have identified various cytokines and cytokine receptors involved in Type 2 inflammatory diseases, particularly Interleukin-4 Receptor alpha and associated cytokines Interleukin-4 and Interleukin-13 have been identified as key drivers of Type 2 inflammatory pathways.

Human Interleukin-4 Receptor alpha (also known as IL-4Rα; IL-4 receptor subunit alpha; CD124; BSF receptor) is a transmembrane glycoprotein in the class I cytokine receptor family that plays an important role in diverse biological processes, including Th2-based immune responses, alternative macrophage and dendritic cell activation, mucosal immunity, allergic inflammation, tumor progression, and atherogenesis. IL-4Rα has been reported as being expressed on T and B lymphocytes, eosinophils, basophils, monocytes and macrophages, dendritic cells, endothelial cells, fibroblasts, airway epithelial cells and smooth muscle cells. IL-4Rα exists in 2 different complexes throughout the body, Type I receptors are composed of the IL-4Rα subunit with a common γ chain and specifically binds IL-4, whereas Type II receptors consist of an IL-4Rα subunit bound to a different subunit known as IL-13Rα1. Both type I and type II IL-4Rα receptors are referred to as IL-4 receptors (IL-4R). Type I IL-4Rα is found in for example, lymphocytes and myeloid cells, and the type II IL-4Rα is found in for example, myeloid cells and non-hematopoietic cells. These type II receptors have the ability to bind both Interleukin-4 and Interleukin-13, two cytokines with closely related biological functions.

Human Interleukin-4 (also known as IL-4; BSF-1) is present in a broad spectrum of tissues, including hematopoietic, endothelial, epithelial, muscle, fibroblast, hepatocyte, and brain tissues. Human IL-4 has been found to be a key regulator in humoral and adaptive immunity, and plays a role in for example, stimulation of activated B-cell, T-cell proliferation, differentiation of B cells into plasma cells, induction of differentiation of naïve CD4+ T cells into Th2 effector cells, up-regulation of, MHC class II production, CD23, and IL-4Rα on B cells and myeloid lineage cells, such as monocytic cells, decrease in production of Th1 cells, macrophages, IFN-gamma, and dendritic cell IL-12. (Hershey et al., N. Engl. J. Med. 1997, 337 (24): 1720-5).

Human Interleukin-13 (also known as IL-13; P600) plays an important role in for example goblet cell metaplasia, smooth cell muscle contraction, and mucus production in the airway epithelium, for example, in allergic asthma. Binding of IL-13 complex to IL-4Rα initiates the activation of multiple transduction pathways including tyrosine kinase 2 (Tyk-2) and Janus kinase 1 (JAK1). As such, both IL-4 and IL-13 cytokines activate STAT6 transcription factor, promote B-cell class switching to IgE and chemotaxis of eosinophils, and have also been found to play a potential role in tumor proliferation, cell survival, cell adhesion, and metastasis. (Suzuki, A., et al., Cytokine 2015; 75(1):79-88). IL-13 is expressed by multiple cell types including, B cells, basophils, eosinophils, mast cells, endothelial cells, fibroblasts, monocytes, macrophages, respiratory epithelial cells, and smooth muscle cells. (Hershey et al., N. Engl. J. Med. 1997, 337 (24): 1720-5).

Antibody therapeutics targeting Type 2 inflammatory diseases are known, and either approved or in clinical development. Such antibodies include, dupilumab which targets the IL-4Rα; pascolizumab that targets IL-4; lebrikizumab, anrukinzumab, and tralokinumab that target the IL-13 pathway. (Junttila, I., Frontiers in Immunology 2018, 9: 888). However, in spite of the development of these targeted therapies there remains a need for additional IL-4Rα antibodies, for use in patients having Type 2 inflammatory disorders such as, asthma, atopic dermatitis, and/or eosinophilic esophagitis (EoE), and for patients who remain resistant to treatment, or are non-durable responders of current therapies, such as dupilumab.

DETAILED DESCRIPTION

The present disclosure provides antibodies that specifically bind human IL-4Rα and inhibit IL-4R, IL-4 and/or IL-13 mediated responses (e.g., B cell proliferation, STAT-6 phosphorylation, CD23 expression), compositions comprising such IL-4Rα antibodies, and methods of using such IL-4Rα antibodies. Particularly, the present disclosure provides human IL-4Rα antibodies that bind a novel epitope spanning the n-terminal fibronectin type-III domains 1 and 2 of the human and/or cynomolgus monkey IL-4Rα, have desired binding affinities, block both IL-4 and IL-13 mediated IL-4R signaling, and/or have good developability properties such as viscosity and/or aggregation. Such human IL-4Rα antibodies can be used to treat Type 2 inflammatory disorders, associated with IL-4 or IL-13 mediated IL-4R signaling, including atopic dermatitis, eosinophilic esophagitis (EoE), nasal polyposis, asthma, chronic rhinosinusitis (CRS), allergic disease, chronic obstructive pulmonary disease (COPD), or chronic spontaneous urticaria (CSU). Such IL-4Rα antibodies can be further used to treat cancer. As such, the human IL-4Rα antibodies provided herein have one or more of the following properties: 1) bind a novel structural epitope spanning the n-terminal fibronectin type-III domains 1 and 2 of the human and/or cynomolgus monkey IL-4Rα, 2) bind a novel functional epitope on the human and/or cynomolgus monkey IL-4Rα, 3) bind human and/or cynomolgus monkey IL-4Rα with desirable binding affinities, 4) inhibit IL-4 mediated IL-4R signaling, 5) inhibit IL-13 mediated IL-4R signaling, 6) do not significantly induce effector function mediated killing, 7) do not significantly induce complement binding, 8) retains Fcγ receptor binding and/or 9) have low, viscosity, serum protein binding and/or aggregation.

In some embodiments, the antibodies of the present disclosure that specifically bind human IL-4Rα are fully human antibodies. In some embodiments, the antibodies of the present disclosure bind a novel structural epitope of the human IL-4Rα, wherein the epitope spans domain 1 and domain 2 of the n-terminal fibronectin type-III domain of the IL-4Rα. In some embodiments, the antibodies of the present disclosure bind a novel functional epitope of the human IL-4Rα. In some embodiments, the antibodies of the present disclosure specifically bind human IL-4Rα on B cells, T cells, and myeloid cells. In further embodiments, antibodies of the present disclosure bind human and/or cynomolgus monkey IL-4Rα and block IL-4 and IL-13 binding to IL-4Rα thereby preventing IL-4R mediated signaling. In some embodiments, the antibodies of the present disclosure inhibit IL-4 and IL-13 induced IL-4R STAT-6 phosphorylation, B cell proliferation, and CD23 expression. In yet further embodiments, the antibodies of the present disclosure do not significantly induce effector function mediated killing. In some embodiments, the anti-human IL-4Rα antibody having a human IgG4P or a human IgG1A backbone retains Fcγ receptor binding. In such embodiments, the anti-human IL-4Rα antibody having a human IgG4P or human IgG1A backbone has improved binding to B cells and myeloid cells, when compared to a human IL-4Rα antibody having an effector null backbone (e.g., IgG1AAA).

In some embodiments, the human IL-4Rα antibody or antigen binding fragment thereof of the present disclosure specifically binds to an epitope of human IL-4Rα, wherein the epitope comprises one or more amino acid residues selected from D12, M14, S15, I16, Y37, L39, F41, L42, L43, E45, H47, T48, C49, I50, E52, H62, L64, M65, D66, D67, V68, V69, D72, R99, P121, P123, P124, D125, P192 (the amino acid residue positions correspond to SEQ ID NO: 15). In some embodiments, the human IL-4Rα antibody or antigen binding fragment thereof of the present disclosure specifically binds to an epitope of human IL-4Rα, wherein the epitope comprises at least one, at least two, at least three, at least four, or at least five or more amino acid residues selected from D12, M14, S15, I16, Y37, L39, F41, L42, L43, E45, H47, T48, C49, I50, E52, H62, L64, M65, D66, D67, V68, V69, D72, R99, P121, P123, P124, D125, P192 (the amino acid residue positions correspond to SEQ ID NO: 15). In some embodiments, the human IL-4Rα antibody or antigen binding fragment thereof specifically binds to an epitope of human IL-4Rα comprising one or more amino acid residues selected from D12, M14, S15, I16, Y37, L39, F41, L43, E45, H47, T48, C49, I50, H62, L64, M65, D66, D67, V69, D72, R99, P121, P123, P124, D125 (the amino acid residue positions correspond to SEQ ID NO: 15). In some embodiments, the human IL-4Rα antibody or antigen binding fragment thereof of the present disclosure specifically binds to an epitope of human IL-4Rα, wherein the epitope comprises at least one, at least two, at least three, at least four, or at least five or more amino acid residues selected from D12, M14, S15, I16, Y37, L39, F41, L43, E45, H47, T48, C49, I50, H62, L64, M65, D66, D67, V69, D72, R99, P121, P123, P124, D125 (the amino acid residue positions correspond to SEQ ID NO: 15). In some embodiments, the human IL-4Rα antibody or antigen binding fragment thereof specifically binds to an epitope of human IL-4Rα comprising one or more amino acid residues selected from D12, M14, S15, I16, L39, F41, L42, T48, C49, I50, E52, H62, L64, M65, D66, D67, V68, V69, D72, R99, P121, P123, P124, D125, P192 (the amino acid residue positions correspond to SEQ ID NO: 15). In some embodiments, the human IL-4Rα antibody or antigen binding fragment thereof of the present disclosure specifically binds to an epitope of human IL-4Rα, wherein the epitope comprises at least one, at least two, at least three, at least four, or at least five or more amino acid residues selected from D12, M14, S15, I16, L39, F41, L42, T48, C49, I50, E52, H62, L64, M65, D66, D67, V68, V69, D72, R99, P121, P123, P124, D125, P192 (the amino acid residue positions correspond to SEQ ID NO: 15). In further embodiments, the human IL-4Rα antibody or antigen binding fragment thereof specifically binds to an epitope of human IL-4Rα comprising one or more amino acid residues selected from D12, M14, S15, I16, Y37, 10 L39, T48, C49, I50, E52, H62, M65, R99, P121, P123, P124, D125, P192 (the amino acid residue positions correspond to SEQ ID NO: 15). In further embodiments, the human IL-4Rα antibody or antigen binding fragment thereof of the present disclosure specifically binds to an epitope of human IL-4Rα, wherein the epitope comprises at least one, at least two, at least three, at least four, or at least five or more amino acid residues selected from D12, M14, S15, I16, Y37, L39, T48, C49, I50, E52, H62, M65, R99, P121, P123, P124, D125, P192 (the amino acid residue positions correspond to SEQ ID NO: 15). In further embodiments, the human IL-4Rα antibody or antigen binding fragment thereof specifically binds to an epitope of human IL-4Rα comprising one or more amino acid residue selected from R99, P121, P123, P124, D125, P192 (the amino acid residue positions correspond to SEQ ID NO: 15), wherein these residues are located in domain 2 of the N-terminal fibronectin type-III domains of the IL-4Rα. In yet further embodiments, the human IL-4Rα antibody or antigen binding fragment thereof specifically binds to an epitope of human IL-4Rα comprising at least one or more of amino acid residues D66, D67, and D125 (the amino acid residue positions correspond to SEQ ID NO: 15). In yet further embodiments, the human IL-4Rα antibody or antigen binding fragment thereof specifically binds to an epitope of human IL-4Rα comprising at least one of amino acid residues D66 and D67 (the amino acid residue positions correspond to SEQ ID NO: 15). In yet further embodiments, the human IL-4Rα antibody or antigen binding fragment thereof specifically binds to an epitope of human IL-4Rα comprising at least one of amino acid residues D66 and D125 (the amino acid residue positions correspond to SEQ ID NO: 15). In yet further embodiments, the human IL-4Rα antibody or antigen binding fragment thereof specifically binds to an epitope of human IL-4Rα comprising amino acid residue D66 (the amino acid residue positions correspond to SEQ ID NO: 15). In yet other embodiments, the human IL-4Rα antibody or antigen binding fragment thereof specifically binds a structural and/or functional epitope of the human IL-4Rα, wherein the epitope spans domain 1 and domain 2 of the n-terminal fibronectin type-III domains of the IL-4Rα. In particular embodiments, the human IL-4Rα antibody or antigen binding fragment thereof specifically binds to a novel structural and/or functional epitope of the human IL-4Rα, wherein the epitope overlaps with the IL-4 binding site to IL-4Rα. In such embodiments, the human IL-4Rα antibody or antigen binding fragment thereof blocks binding of IL-4 to the human IL-4Rα. In particular embodiments, the human IL-4Rα antibody or antigen binding fragment thereof binds a novel structural and/or functional epitope of the human IL-4Rα, wherein the epitope overlaps with the IL-13 binding site to IL-4Rα. In such embodiments, the human IL-4Rα antibody or antigen binding fragment thereof blocks binding of IL-13 to the human IL-4Rα. In particular embodiments, the human IL-4Rα antibody or antigen binding fragment thereof binds a novel structural and/or functional epitope of the human IL-4Rα, wherein the epitope overlaps with both the IL-4 and the IL-13 binding sites to IL-4Rα. In such embodiments, the human IL-4Rα antibody or antigen binding fragment thereof blocks binding of IL-4 and IL-13 to the human IL-4Rα. In some embodiments, the IL-4Rα epitope is determined by X-ray crystallography, alanine scanning mutagenesis, steric hindrance mutagenesis, and/or HDX-MS. In yet other embodiments, the IL-4Rα epitope is determined by site-directed mutagenesis.

In some embodiments, the present disclosure provides an antibody or antigen binding fragment thereof, that specifically binds human IL-4Rα, and comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 1, the HCDR2 comprises SEQ ID NO: 2, the HCDR3 comprises SEQ ID NO: 3, the LCDR1 comprises SEQ ID NO: 4, the LCDR2 comprises SEQ ID NO: 5, and the LCDR3 comprises SEQ ID NO: 6. In some embodiments, the antibody or antigen binding fragment thereof that specifically bind IL-4Rα comprise a VH comprising SEQ ID NO: 7 and a VL comprising SEQ ID NO: 8. In some embodiments, the antibody or antigen binding fragment thereof comprises a HC comprising SEQ ID NO: 33 and a LC comprising SEQ ID NO: 10. In some embodiments, the antibody or antigen binding fragment thereof comprises a HC comprising SEQ ID NO: 35 and a LC comprising SEQ ID NO: 10. In some embodiments, the antibody or antigen binding fragment thereof comprises a HC comprising SEQ ID NO: 9 and a LC comprising SEQ ID NO: 10. In some embodiments, the antibody or antigen binding fragment thereof comprises a HC comprising SEQ ID NO: 13 and a LC comprising SEQ ID NO: 10. In some embodiments, the antibody or antigen binding fragment thereof comprises a HC comprising SEQ ID NO: 37 and a LC comprising SEQ ID NO: 10. In some embodiments, the antibody or antigen binding fragment thereof comprises a HC comprising SEQ ID NO: 31 and a LC comprising SEQ ID NO: 10. In some embodiments, the antibody or antigen binding fragment thereof comprises a HC comprising SEQ ID NO: 50 and a LC comprising SEQ ID NO: 10. In some embodiments, the antibody or antigen binding fragment thereof comprises a HC comprising SEQ ID NO: 52 and a LC comprising SEQ ID NO: 10.

In some embodiments, the present disclosure provides an antibody or antigen binding fragment thereof, that specifically binds human IL-4Rα, wherein the antibody or antigen binding fragment thereof comprise a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 42, the HCDR2 comprises SEQ ID NO: 2, the HCDR3 comprises SEQ ID NO: 3, the LCDR1 comprises SEQ ID NO: 22, the LCDR2 comprises SEQ ID NO: 5, and the LCDR3 comprises SEQ ID NO: 6. In some embodiments, the antibody or antigen binding fragment thereof that specifically bind IL-4Rα comprise a VH comprising SEQ ID NO: 44 and a VL comprising SEQ ID NO: 45. In some embodiments, the antibody or antigen binding fragment thereof comprises a HC comprising SEQ ID NO: 46 and a LC comprising SEQ ID NO: 47.

In some embodiments, the present disclosure provides an antibody or antigen binding fragment thereof, that specifically binds human IL-4Rα, wherein the antibody or antigen binding fragment thereof comprise a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein the HCDR1 comprises SEQ ID NO: 19, the HCDR2 comprises SEQ ID NO: 20, the HCDR3 comprises SEQ ID NO: 3, the LCDR1 comprises SEQ ID NO: 22, the LCDR2 comprises SEQ ID NO: 5, and the LCDR3 comprises SEQ ID NO: 24. In some embodiments, the human IL-4Rα antibodies comprise a VH comprising SEQ ID NO: 25 and a VL comprising SEQ ID NO: 26. In some embodiments, the antibody or antigen binding fragment thereof, that specifically binds human IL-4Rα, comprises a heavy chain (HC) comprising SEQ ID NO: 27 and a light chain (LC) comprising SEQ ID NO: 28.

In some embodiments of the present disclosure, the antibody or antigen binding fragment thereof specifically binding human IL-4Rα has a human IgG1 or a human IgG4 isotype.

In some embodiments of the present disclosure, the antibody or antigen binding fragment thereof specifically binding human IL-4Rα has a human IgG1 isotype. In some embodiments, the human IL-4Rα antibody has a modified human IgG1 Fcγ region wherein the antibody comprises an alanine at amino acid residue 322 (K322A substitution) (EU numbering) also referred to as IgG1A. In such embodiments, the human IL-4Rα antibody or antigen binding fragment thereof of the present disclosure has reduced or eliminated complement activity. In some embodiments, the human IL-4Rα antibody or antigen binding fragment thereof has a modified human IgG1 Fcγ region comprising a L234A, an L235A and/or a P329A also referred to as IgG1AA or IgGIAAA respectively, which have reduced or eliminated binding to the Fcγ and C1q receptors (all residues numbered according to EU numbering). In some embodiments, the human IL-4Rα antibody or antigen binding fragment thereof having a human IgG1A backbone shows improved binding to B cells and myeloid cells, when compared to the human IL-4Rα antibody having a human IgG1AAA effector null backbone.

In some embodiments of the present disclosure, the antibody or antigen binding fragment thereof specifically binding human IL-4Rα has a human IgG4 isotype. In some embodiments, the human IL-4Rα antibody or antigen binding fragment thereof has a modified human IgG4 hinge region comprising a S228P substitution (EU Numbering), also referred to as IgG4P, which reduces the IgG4 Fab-arm exchange in vivo (see Labrijn, et al., Nat. Biotechnol. 2009, 27(8):767). In some embodiments, the human IL-4Rα antibody or antigen binding fragment thereof has a modified human IgG4 Fcγ region comprising a F234A and/or a L235A (EU numbering) also referred to as IgG4AA, which reduce binding to the Fc7 and C1q receptors. According to some embodiments of the present disclosure, the Fcγ region comprises S228P, F234A, and L235A (all residues numbered according to IMGT or EU numbering) also referred to as IgG4PAA. In some embodiments, the human IL-4Rα antibody or antigen binding fragment thereof having a human IgG4P backbone has improved binding to B cells and myeloid cells, when compared to a human IL-4Rα antibody having an effector null backbone.

In some embodiments, the human IL-4Rα antibody or antigen binding fragment thereof has a modified human IgG4 HC region which reduces viscosity of the antibody compared to the same antibody with a wild-type human IgG4 HC constant region. In such embodiments, the human IL-4Rα antibody or antigen binding fragment thereof has a modified human IgG4 HC constant region comprising an amino acid substitution at any one or more of the following amino acid residues compared to the wild-type human IgG4 HC constant region: Q274K, Q355R, E419Q (all positions numbered according to EU numbering).

In other embodiments, the human IL-4Rα antibody or antigen binding fragment thereof has a modified human IgG4 HC region comprising an amino acid substitution at any one or more of the following amino acid residues compared to the wild-type human IgG4 HC region: E137G, D203N, Q274K, Q355R, E419Q (all positions numbered according to EU numbering).

In some embodiments, the human IL-4Rα antibody or antigen binding fragment thereof has a modified human IgG4 HC constant region comprising an E137G substitution (EU Numbering). In some embodiments, the human IL-4Rα antibody or antigen binding fragment thereof has a modified human IgG4 HC constant region comprising a D203N substitution (EU numbering). In some embodiments, the human IL-4Rα antibody or antigen binding fragment thereof has a modified human IgG4 HC constant region comprising a Q274K substitution (according to EU numbering). In some embodiments, the human IL-4Rα antibody or antigen binding fragment thereof has a modified human IgG4 HC constant region comprising a Q355R substitution (according to EU numbering). In some embodiments, the human IL-4Rα antibody or antigen binding fragment thereof has a modified human IgG4 HC constant region comprising a E419Q substitution (according to EU Numbering). In some embodiments, the human IL-4Rα antibody or antigen binding fragment thereof has a modified human IgG4 HC constant region comprising Q274K and Q355R substitutions (all positions numbered according to EU numbering). In some embodiments, the human IL-4Rα antibody or antigen binding fragment thereof has a modified human IgG4 HC constant region comprising Q274K and E419Q substitutions (all positions numbered according to EU numbering). In some embodiments, the human IL-4Rα antibody or antigen binding fragment thereof has a modified human IgG4 HC constant region comprising Q355R and E419Q substitutions (all positions numbered according to EU numbering). In some embodiments, the human IL-4Rα antibody or antigen binding fragment thereof has a modified human IgG4 HC constant region comprising Q274K, Q355R, and E419Q substitutions (all positions numbered according to EU numbering). In some embodiments, the human IL-4Rα antibody or antigen binding fragment thereof has a modified human IgG4 HC constant region comprising S228P, Q274K, Q355R, E419Q substitutions (all positions numbered according to EU numbering). In some embodiments, the human IL-4Rα antibody or antigen binding fragment thereof has a modified human IgG4 HC region comprising S228P, E137G, D203N, Q274K, Q355R, E419Q substitutions (all positions numbered according to EU numbering).

In some embodiments, the antibody or antigen binding fragment thereof comprises one or more of the following: a glycine at amino acid residue 137 (EU numbering), an asparagine at amino acid residue 203 (EU numbering), a lysine at amino acid residue 274 (EU numbering), an arginine at amino acid residue 355 (EU numbering), or a glutamine at amino acid residue 419 (EU numbering).

In some embodiments, the antibody or antigen binding fragment thereof comprises: a lysine at amino acid residue 274 (EU numbering), an arginine at amino acid residue 355, and a glutamine at amino acid residue 419 (EU numbering).

In some embodiments, the antibody or antigen binding fragment thereof comprises: a glycine at amino acid residue 137 (EU numbering), an asparagine at amino acid residue 203 (EU numbering), a lysine at amino acid residue 274 (EU numbering), an arginine at amino acid residue 355, and a glutamine at amino acid residue 419 (EU numbering).

In further embodiments, the human IL-4Rα antibody or antigen binding fragment thereof has a modified human IgG1 or human IgG4 constant domain comprising engineered cysteine residues for use in the generation of antibody conjugate compounds (also referred to as bioconjugates) (see WO 2018/232088 A1). More particularly, in such embodiments of the present disclosure, the human IL-4Rα antibody or antigen binding fragment thereof comprises a cysteine at amino acid residue 124 (EU numbering), or a cysteine at amino acid residue 378 (EU numbering), or a cysteine at amino acid residue 124 (EU numbering) and cysteine at amino acid residue 378 (EU numbering).

In some embodiments, the antibody or antigen binding fragment thereof specifically binding human IL-4Rα has a modified human IgG1 or human IgG4 framework region. In some embodiments, the modifications are in the framework region of VH. In some embodiments, the modifications are in the framework region of VL. In some embodiments, the modifications are in the framework regions of VH and the VL. In further embodiments, the modified human IgG1 or human IgG4 framework region lowers the immunogenicity risk of the antibody.

In some embodiments of the present disclosure, the human IL-4Rα antibody or antigen binding fragment thereof of the present disclosure binds IL-4Rα and inhibits binding of human IL-4 and human IL-13 to human IL-4Rα. In such embodiments, the antibody or antigen binding fragment thereof of the present disclosure inhibits binding of human IL-4 to human IL-4Rα and thus inhibits human IL-4R activation, STAT-6 phosphorylation, B cell and/or T cell proliferation, and CD23 expression. In such embodiments, the antibody or antigen binding fragment thereof of the present disclosure binds human IL-4Rα and inhibits binding of human IL-4 to human IL-4Rα by about 10%, about 20%, about 30%, about 40%, about 50%, about 60%, about 70%, about 80%, about 90%, or about 100%. In further embodiments, the human IL-4Rα antibody or antigen binding fragment thereof of the present disclosure binds human IL-4Rα on B and T cells and inhibits IL-4 induced STAT-6 phosphorylation in B and T cells by about 10%, about 20%, about 30%, about 40%, about 50%, about 60%, about 70%, about 80%, about 90%, or about 100%. In further embodiments, the human IL-4Rα antibody or antigen binding fragment thereof of the present disclosure binds human IL-4Rα on B cells and inhibits IL-4 induced B cell proliferation by about 10%, about 20%, about 30%, about 40%, about 50%, about 60%, about 70%, about 80%, about 90%, or about 100%. In yet other embodiments, the human IL-4Rα antibody or antigen binding fragment thereof of the present disclosure binds human IL-4Rα on myeloid cells and inhibits IL-4 induced CD23 expression on human myeloid cells by about 10%, about 20%, about 30%, about 40%, about 50%, about 60%, about 70%, about 80%, about 90%, or about 100%.

In some embodiments, the human IL-4Rα antibody or antigen binding fragment thereof of the present disclosure inhibits the binding of human IL-13 to human IL-4Rα. In such embodiments, the antibody or antigen binding fragment thereof of the present disclosure inhibits binding of human IL-13 to human IL-4Rα and thus inhibits human IL-4R activation, STAT-6 phosphorylation, B and/or T cell proliferation and CD23 expression. In further embodiments, the antibody or antigen binding fragment thereof of the present disclosure binds human IL-4Rα and inhibits binding of human IL-13 to human IL-4Rα by about 10%, about 20%, about 30%, about 40%, about 50%, about 60%, about 70%, about 80%, about 90%, or about 100%. In yet further embodiments, the human IL-4Rα antibody or antigen binding fragment thereof of the present disclosure binds human IL-4Rα on B cells and inhibits IL-13 induced STAT-6 activation in B cells by about 10%, about 20%, about 30%, about 40%, about 50%, about 60%, about 70%, about 80%, about 90%, or about 100%. In further embodiments, the antibody or antigen binding fragment thereof of the present disclosure inhibits binding of human IL-13 to human IL-4Rα and inhibits B cell and/or T cell proliferation. In such embodiments, the human IL-4Rα antibody or antigen binding fragment thereof of the present disclosure binds human IL-4Rα on B cells and/or T cells and inhibits IL-13 induced B and/or T cell proliferation by about 10%, about 20%, about 30%, about 40%, about 50%, about 60%, about 70%, about 80%, about 90%, or about 100%. In yet other embodiments, the human IL-4Rα antibody or antigen binding fragment thereof of the present disclosure binds human IL-4Rα on myeloid cells and inhibits IL-13 induced CD23 expression on human myeloid cells by about 10%, about 20%, about 30%, about 40%, about 50%, about 60%, about 70%, about 80%, about 90%, or about 100%.

In some embodiments, the human IL-4Rα antibody or antigen binding fragment thereof of the present disclosure inhibits the binding of human IL-4 and human IL-13 to human IL-4Rα by binding to a novel epitope of human IL-4Rα, wherein the epitope comprises one or more amino acid residues selected from D12, M14, S15, I16, Y37, L39, F41, L42, L43, E45, H47, T48, C49, I50, E52, H62, L64, M65, D66, D67, V68, V69, D72, R99, P121, P123, P124, D125, P192 (the amino acid residue positions correspond to SEQ ID NO: 15). In some embodiments, the human IL-4Rα antibody or antigen binding fragment thereof inhibits the binding of human IL-4 and/or human IL-13 to human IL-4Rα by binding to an epitope of human IL-4Rα, wherein the epitope comprises one or more amino acid residues selected from D12, M14, S15, I16, Y37, L39, F41, L43, E45, H47, T48, C49, I50, H62, L64, M65, D66, D67, V69, D72, R99, P121, P123, P124, D125 (the amino acid residue positions correspond to SEQ ID NO: 15). In some embodiments, the human IL-4Rα antibody or antigen binding fragment thereof inhibits the binding of human IL-4 and/or human IL-13 to human IL-4Rα by binding to an epitope of human IL-4Rα, wherein the epitope comprises one or more amino acid residues selected from D12, M14, S15, I16, L39, F41, L42, T48, C49, I50, E52, H62, L64, M65, D66, D67, V68, V69, D72, R99, P121, P123, P124, D125, P192 (the amino acid residue positions correspond to SEQ ID NO: 15). In some embodiments, the human IL-4Rα antibody or antigen binding fragment thereof inhibits the binding of human IL-4 and/or human IL-13 to human IL-4Rα by binding to an epitope of human IL-4Rα, wherein the epitope comprises one or more amino acid residues selected from D12, M14, S15, I16, Y37, L39, T48, C49, I50, E52, H62, M65, R99, P121, P123, P124, D125, P192 (the amino acid residue positions correspond to SEQ ID NO: 15). In further embodiments, the human IL-4Rα antibody or antigen binding fragment thereof inhibits the binding of human IL-4 and/or human IL-13 to human IL-4Rα by binding to an epitope of human IL-4Rα, wherein the epitope comprises one or more amino acid residue selected from R99, P121, P123, P124, D125, P192 (the amino acid residue positions correspond to SEQ ID NO: 15), wherein these residues are located in domain 2 of the N-terminal fibronectin type-III domain of the IL-4Rα. In yet further embodiments, the human IL-4Rα antibody or antigen binding fragment thereof inhibits the binding of human IL-4 and/or human IL-13 to human IL-4Rα by binding to an epitope of human IL-4Rα, wherein the epitope comprises at least one of amino acid residues D66, D67, and D125 (the amino acid residue positions correspond to SEQ ID NO: 15). In yet further embodiments, the human IL-4Rα antibody or antigen binding fragment thereof inhibits the binding of human IL-4 and/or human IL-13 to human IL-4Rα by binding to an epitope of human IL-4Rα, wherein the epitope comprises at least one of amino acid residues D66 and D67 (the amino acid residue positions correspond to SEQ ID NO: 15). In yet further embodiments, the human IL-4Rα antibody or antigen binding fragment thereof inhibits the binding of human IL-4 and/or human IL-13 to human IL-4Rα by binding to an epitope of human IL-4Rα, wherein the epitope comprises at least one of amino acid residues D66 and D125 (the amino acid residue positions correspond to SEQ ID NO: 15). In yet further embodiments, the human IL-4Rα antibody or antigen binding fragment thereof inhibits the binding of human IL-4 and/or human IL-13 to human IL-4Rα by binding to an epitope of human IL-4Rα, wherein the epitope comprises amino acid residue D66 (the amino acid residue positions correspond to SEQ ID NO: 15).

Some embodiments of the present disclosure provide nucleic acids encoding a heavy chain or light chain, or a VH or VL, of the novel antibodies that specifically bind human IL-4Rα, or vectors comprising such nucleic acids.

In some embodiments, the present disclosure provides a nucleic acid comprising a sequence of SEQ ID NO: 11, 12, 14, 29, 30, 32, 34, 36, 38, 48, 49, 51, or 53.

In some embodiments, nucleic acids encoding a heavy chain or light chain of the antibodies specifically binding human IL-4Rα are provided. In some embodiments nucleic acids comprising a sequence encoding SEQ ID NO: 9, 10, 13, 27, 28, 31, 33, 35, 37, 46, 47, 50, or 52 are provided. In some embodiments, nucleic acids comprising a sequence encoding an antibody heavy chain that comprises SEQ ID NO: 9, 13, 27, 31, 33, 35, 37, 46, 50, or 52 are provided. For example, the nucleic acid can comprise a sequence selected from SEQ ID NO: 11, 14, 29, 32, 34, 36, 38, 48, 51, or 53. In some embodiments, nucleic acids comprising a sequence encoding an antibody light chain that comprises SEQ ID NO: 10, 28, or 47 is provided. For example, the nucleic acid can comprise a sequence selected from SEQ ID NO: 12, 30, or 49.

In some embodiments of the present disclosure, nucleic acids encoding a VH or VL of the antibodies specifically binding human IL-4Rα are provided. In some embodiments, nucleic acids comprising a sequence encoding SEQ ID NO: 7, 8, 25, 26, 44, or 45 are provided. In some embodiments, nucleic acids comprising a sequence encoding an antibody VH that comprises SEQ ID NO: 7, 25, or 44 are provided. In some embodiments, nucleic acids comprising a sequence encoding an antibody VL that comprises SEQ ID NO: 8, 26, or 45 are provided.

Some embodiments of the present disclosure provide vectors comprising a nucleic acid sequence encoding an antibody heavy chain or light chain. For example, such vectors can comprise a nucleic acid sequence encoding SEQ ID NO: 9, 13, 27, 31, 33, 35, 37, 46, 50, or 52. In some embodiments, the vector comprises a nucleic acid sequence encoding SEQ ID NO: 10, 28, or 47.

Provided herein are also vectors comprising a nucleic acid sequence encoding an antibody VH or VL. For example, such vectors can comprise a nucleic acid sequence encoding SEQ ID NO: 7, 25, or 44. In some embodiments, the vector comprises a nucleic acid sequence encoding SEQ ID NO: 8, 26, or 45.

Provided herein are also vectors comprising a first nucleic acid sequence encoding an antibody heavy chain and a second nucleic acid sequence encoding an antibody light chain. In some embodiments, the vector comprises a first nucleic acid sequence encoding SEQ ID NO: 9, 13, 27, 31, 33, 35, 37, 46, 50, or 52 and a second nucleic acid sequence encoding SEQ ID NO: 10, 28, or 47.

In some embodiments, the vector comprises a first nucleic acid sequence encoding SEQ ID NO: 9 and a second nucleic acid sequence encoding SEQ ID NO: 10. In some embodiments, the vector comprises a first nucleic acid sequence encoding SEQ ID NO: 13 and a second nucleic acid sequence encoding SEQ ID NO: 10. In some embodiments, the vector comprises a first nucleic acid sequence encoding SEQ ID NO: 27 and a second nucleic acid sequence encoding SEQ ID NO: 28. In some embodiments, the vector comprises a first nucleic acid sequence encoding SEQ ID NO: 31 and a second nucleic acid sequence encoding SEQ ID NO: 10. In some embodiments, the vector comprises a first nucleic acid sequence encoding SEQ ID NO: 33 and a second nucleic acid sequence encoding SEQ ID NO: 10. In some embodiments, the vector comprises a first nucleic acid sequence encoding SEQ ID NO: 35 and a second nucleic acid sequence encoding SEQ ID NO: 10. In some embodiments, the vector comprises a first nucleic acid sequence encoding SEQ ID NO: 37 and a second nucleic acid sequence encoding SEQ ID NO: 10. In some embodiments, the vector comprises a first nucleic acid sequence encoding SEQ ID NO: 50 and a second nucleic acid sequence encoding SEQ ID NO: 10.

In some embodiments, the vector comprises a first nucleic acid sequence encoding SEQ ID NO: 52 and a second nucleic acid sequence encoding SEQ ID NO: 10. In some embodiments, the vector comprises a first nucleic acid sequence encoding SEQ ID NO: 46 and a second nucleic acid sequence encoding SEQ ID NO: 47.

Also provided are compositions comprising a first vector comprising a nucleic acid sequence encoding an antibody heavy chain, and a second vector comprising a nucleic acid sequence encoding an antibody light chain. In some embodiments, the composition comprises a first vector comprising a nucleic acid sequence encoding SEQ ID NO: 9, 13, 27, 31, 33, 35, 37, 46, 50 or 52 and a second nucleic acid sequence encoding SEQ ID NO: 10, 28, or 47.

In some embodiments, the composition comprises a first vector comprising a nucleic acid sequence encoding SEQ ID NO: 9 and a second vector comprising a nucleic acid sequence encoding SEQ ID NO: 10. In some embodiments, the composition comprises a first vector comprising a nucleic acid sequence encoding SEQ ID NO: 13 and a second vector comprising a nucleic acid sequence encoding SEQ ID NO: 10. In some embodiments, the composition comprises a first vector comprising a nucleic acid sequence encoding SEQ ID NO: 27 and a second vector comprising a nucleic acid sequence encoding SEQ ID NO: 28. In some embodiments, the composition comprises a first vector comprising a nucleic acid sequence encoding SEQ ID NO: 31 and a second vector comprising a nucleic acid sequence encoding SEQ ID NO: 10. In some embodiments, the composition comprises a first vector comprising a nucleic acid sequence encoding SEQ ID NO: 33 and a second vector comprising a nucleic acid sequence encoding SEQ ID NO: 10. In some embodiments, the composition comprises a first vector comprising a nucleic acid sequence encoding SEQ ID NO: 35 and a second vector comprising a nucleic acid sequence encoding SEQ ID NO: 10. In some embodiments, the composition comprises a first vector comprising a nucleic acid sequence encoding SEQ ID NO: 37 and a second vector comprising a nucleic acid sequence encoding SEQ ID NO: 10. In some embodiments, the composition comprises a first vector comprising a nucleic acid sequence encoding SEQ ID NO: 50 and a second vector comprising a nucleic acid sequence encoding SEQ ID NO: 10. In some embodiments, the composition comprises a first vector comprising a nucleic acid sequence encoding SEQ ID NO: 52 and a second vector comprising a nucleic acid sequence encoding SEQ ID NO: 10. In some embodiments, the composition comprises a first vector comprising a nucleic acid sequence encoding SEQ ID NO: 46 and a second vector comprising a nucleic acid sequence encoding SEQ ID NO: 47.

Nucleic acids of the present disclosure may be expressed in a host cell, for example, after the nucleic acids have been operably linked to an expression control sequence. Expression control sequences capable of expression of nucleic acids to which they are operably linked are well known in the art. An expression vector may include a sequence that encodes one or more signal peptides that facilitate secretion of the polypeptide(s) from a host cell. Expression vectors containing a nucleic acid of interest (e.g., a nucleic acid encoding a heavy chain or light chain of an antibody) may be transferred into a host cell by well-known methods, e.g., stable or transient transfection, transformation, transduction or infection. Additionally, expression vectors may contain one or more selection markers, e.g., tetracycline, neomycin, and dihydrofolate reductase, to aide in detection of host cells transformed with the desired nucleic acid sequences.

In another aspect, provided herein are cells, e.g., host cells, comprising the nucleic acids, vectors, or nucleic acid compositions described herein. A host cell may be a cell stably or transiently transfected, transformed, transduced or infected with one or more expression vectors expressing all or a portion of an antibody described herein. In some embodiments, a host cell may be stably or transiently transfected, transformed, transduced or infected with an expression vector expressing HC and LC polypeptides of an antibody of the present disclosure. In some embodiments, a host cell may be stably or transiently transfected, transformed, transduced, or infected with a first vector expressing HC polypeptides and a second vector expressing LC polypeptides of an antibody described herein. Such host cells, e.g., mammalian host cells, can express the antibodies that specifically bind human IL-4Rα as described herein. Mammalian host cells known to be capable of expressing antibodies include CHO cells, HEK293 cells, COS cells, and NS0 cells.

In some embodiments, the cell, e.g., host cell, comprises a vector comprising a first nucleic acid sequence encoding SEQ ID NO: 9, 13, 27, 31, 33, 35, 37, 46, 50, or 52 and a second nucleic acid sequence encoding SEQ ID NO: 10, 28, or 47.

In some embodiments, the cell, e.g., host cell, comprises a first vector comprising a nucleic acid sequence encoding SEQ ID NO: 9, 13, 27, 31, 33, 35, 37, 46, 50, or 52 and a second vector comprising a nucleic acid sequence encoding SEQ ID NO: 10, 28, or 47.

The present disclosure further provides a process for producing an antibody or antigen binding fragments thereof that specifically binds human IL-4Rα described herein by culturing the host cell described above, e.g., a mammalian host cell, under conditions such that the antibody is expressed and recovering the expressed antibody from the culture medium. The culture medium, into which an antibody has been secreted, may be purified by conventional techniques. Various methods of protein purification may be employed, and such methods are known in the art and described, for example, in Deutscher, Methods in Enzymology 182: 83-89 (1990) and Scopes, Protein Purification: Principles and Practice, 3rd Edition, Springer, NY (1994).

The present disclosure further provides antibodies or antigen binding fragments thereof produced by any of the processes described herein.

In another aspect, provided herein are pharmaceutical compositions comprising an antibody, nucleic acid, or vector described herein. Such pharmaceutical compositions can also comprise one or more pharmaceutically acceptable excipient, diluent, or carrier. Pharmaceutical compositions can be prepared by methods well known in the art (e.g., *Remington: The Science and Practice of Pharmacy,* 22nd ed. (2012), A. Loyd et al., Pharmaceutical Press).

The antibodies or antigen binding fragments thereof that specifically bind human IL-4Rα, nucleic acids, vectors, or pharmaceutical compositions described herein can be used for treating an IL-4R associated disorder such as immune inflammatory disorders, such as Type 2 inflammatory disorders, including but not limited to atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU). As such, the antibodies of the disclosure can be further used for treating cancer, e.g., B cell associated cancer, such as CLL, or other cancers such as malignant glioma, ovarian, lung, breast, squamous cell carcinoma of head and neck (SCCHN), pancreatic, renal, colon, prostate, and bladder cancer. Such methods can further include administering one or more chemotherapeutic agents to the subject. In some embodiments, the chemotherapeutic agent is administered in simultaneous, separate, or sequential combination with an antibody or antigen binding fragment thereof that specifically binds human IL-4Rα described herein or pharmaceutical composition thereof. Embodiments of the present disclosure further provide methods of treating cancer with an antibody or antigen binding fragment thereof that specifically binds human IL-4Rα or pharmaceutical composition thereof, in simultaneous, separate, or sequential combination with ionizing radiation.

In some embodiments, provided herein are methods of treating an IL-4R associated disorder, e.g., an immune inflammatory disorder such as a Type 2 immune inflammatory disorder, or cancer, in a subject (e.g., a human patient) in need thereof, by administering to the subject a therapeutically effective amount of an antibody or antigen binding fragment thereof that specifically binds human IL-4Rα, a nucleic acid encoding such an antibody that specifically binds human IL-4Rα, a vector comprising such a nucleic acid, or a pharmaceutical composition comprising such an antibody that specifically binds human IL-4Rα, nucleic acid or vector, as described herein. The antibodies, nucleic acids, vectors, or pharmaceutical compositions described herein may be administered by parenteral routes (e.g., subcutaneous, and intravenous). In embodiments, the IL-4Rα/IL-4 and/or IL-4Rα/IL-13 associated immune inflammatory disorder is a Type 2 inflammatory disorder. Such Type 2 inflammatory disorders include, but are not limited to, atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU). In some embodiments, the IL-4R order is cancer, e.g., B cell associated cancer, such as CLL, or other cancers such as malignant glioma, ovarian, lung, breast, squamous cell carcinoma of head and neck (SCCHN), pancreatic, renal, colon, prostate, and bladder cancer.

Also provided herein are, antibodies or antigen binding fragments thereof that specifically bind human IL-4Rα, nucleic acids, vectors, or pharmaceutical compositions described herein for use in therapy. Furthermore, the present disclosure also provides, antibodies or antigen binding fragments thereof that specifically bind human IL-4Rα, nucleic acids, vectors, or pharmaceutical compositions described herein for use in the treatment of an IL-4R disorder, e.g., immune inflammatory disorders such as a Type 2 inflammatory disorder, or cancer. Such Type 2 inflammatory disorders include, but are not limited to, atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU). In some embodiments, the IL-4R associated disorder is cancer, e.g., B cell associated cancer, such as CLL, or other cancers such as malignant glioma, ovarian, lung, breast, squamous cell carcinoma of head and neck (SCCHN), pancreatic, renal, colon, prostate, and bladder cancer.

Provided herein are use of the antibodies or antigen binding fragments thereof that specifically bind human IL-4Rα, nucleic acids, vectors, or pharmaceutical compositions described herein in the manufacture of a medicament for the treatment of an IL-4R associated disorder, e.g., immune inflammatory disorders such as a Type 2 inflammatory disorder or cancer. Such Type 2 inflammatory disorders include, but are not limited to, atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU). In some embodiments, the IL-4R associated disorder is cancer, e.g., B cell associated cancer, such as CLL, or other cancers such as malignant glioma, ovarian, lung, breast, squamous cell carcinoma of head and neck (SCCHN), pancreatic, renal, colon, prostate, and bladder cancer.

The term "IL-4Rα" as used herein, unless stated otherwise, refers to any native, mature IL-4Rα that results from processing of an IL-4Rα precursor protein in a cell. The term includes IL-4Rα from any vertebrate source, including mammals such as primates (e.g., humans and cynomolgus or rhesus monkeys) and rodents (e.g., mice and rats), unless otherwise indicated. The term also includes naturally occurring variants of IL-4Rα, e.g., splice variants or allelic variants. The amino acid sequence of an example of human IL-4Rα is known in the art, e.g., UniProt reference sequence P24394 (SEQ ID NO: 39). The amino acid sequence of an example of cynomolgus monkey IL-4Rα is also known in the art, e.g., NCBI reference sequence XP_005591572.2 (SEQ ID NO: 40). The term "IL-4Rα" is used herein to refer collectively to all known human IL-4Rα isoforms and polymorphic forms. Sequence numbering used herein is based on the mature protein without the signal peptide.

The term "IL-4R" as used herein, unless stated otherwise, refers to a complex of the IL-4Rα subunit with a common γ chain (Type I receptor) or a complex of the IL-4Rα subunit with an IL-13Rα1 (Type II receptor).

The term "IL-4" as used herein, unless stated otherwise, refers to any native, mature IL-4 that results from processing of an IL-4 precursor protein in a cell. The term includes IL-4 from any vertebrate source, including mammals such as primates (e.g., humans and cynomolgus or rhesus monkeys) and rodents (e.g., mice and rats), unless otherwise indicated. The term also includes naturally occurring variants of IL-4, e.g., splice variants or allelic variants. The amino acid sequence of an example of human IL-4 is known in the art, e.g., UniProt reference sequence P05112 (SEQ ID NO: 17). The term "IL-4" is used herein to refer collectively to all known human IL-4 isoforms and polymorphic forms.

The term "IL-13" as used herein, unless stated otherwise, refers to any native, mature IL-13 that results from processing of an IL-13 precursor protein in a cell. The term includes IL-13 from any vertebrate source, including mammals such as primates (e.g., humans and cynomolgus or rhesus monkeys) and rodents (e.g., mice and rats), unless otherwise indicated. The term also includes naturally occurring variants of IL-13, e.g., splice variants or allelic variants. The amino acid sequence of an example of human IL-13 is known in the art, e.g., UniProt reference sequence P35225 (SEQ ID NO: 18). The term "IL-13" is used herein to refer collectively to all known human IL-13 isoforms and polymorphic forms.

The term "CD23" as used herein, unless stated otherwise, refers to any native, mature CD23 that results from processing of a CD23 precursor protein in a cell. The term includes CD23 from any vertebrate source, including mammals such as primates (e.g., humans and cynomolgus or rhesus monkeys) and rodents (e.g., mice and rats), unless otherwise indicated. The term also includes naturally occurring variants of CD23, e.g., splice variants or allelic variants. The amino acid sequence of an example of human CD23 is known in the art, e.g., UniProt reference sequence P06734 (SEQ ID NO: 41). The term "CD23" is used herein to refer collectively to all known human CD23 isoforms and polymorphic forms.

The term "IL-4R associated disorder" as used herein refers to a disorder associated with IL-4R mediated signaling, such as for example disorders associated with IL-4R Type 1 and IL-4R Type II signaling. Such an IL-4R associated disorder may for example include immune inflammatory disorders. Such immune inflammatory disorders may include Type 2 inflammatory disorders, as disclosed herein. IL-4R associated disorder may further include cancer.

The term "antibody," as used herein, refers to an immunoglobulin molecule that binds an antigen. Embodiments of an antibody include a monoclonal antibody, polyclonal antibody, human antibody, humanized antibody, chimeric antibody, bispecific or multispecific antibody, or conjugated antibody. The antibodies can be of any class (e.g., IgG, IgE, IgM, IgD, IgA), and any subclass (e.g., IgG1, IgG2, IgG3, IgG4).

An exemplary antibody is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. The heavy chain constant region refers to a region of an antibody, which comprises the Fcγ region and CH1 domain of the antibody heavy chain. Each light chain is comprised of a light chain variable region (VL) and a light chain constant region. The IgG isotype may be further divided into subclasses (e.g., IgG1, IgG2, IgG3, and IgG4). The numbering of the amino acid residues in the constant region is based on the EU index as in Kabat. Kabat et al, *Sequences of Proteins of Immunological Interest,* 5th edition, Bethesda, MD: U.S. Dept. of Health and Human Services, Public Health Service, National Institutes of Health (1991). The term EU Index numbering or EU numbering is used interchangeably herein.

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212). The North CDR definitions are used for the antibodies that specifically bind human IL-4Rα described herein.

Embodiments of the present disclosure also include antibody fragments or antigen binding fragments, which comprise at least a portion of an antibody retaining the ability to specifically interact with an antigen such as Fab, Fab', F(ab')2, Fv fragments, scFv, scFab, disulfide-linked Fvs (sdFv), a Fd fragment or linear antibodies, which may be for example, fused to an Fcγ region or an IgG heavy chain constant region.

fused to an Fcγ region or an IgG heavy chain constant region.

The term "Fcγ region" as used herein, refers to a region of an antibody, which comprises the CH2 and CH3 domains of the antibody heavy chain. Optionally, the Fc region may include a portion of the hinge region or the entire hinge region of the antibody heavy chain. Biological activities such as effector function are attributable to the Fc region, which vary with the antibody isotype. Examples of antibody effector functions include, Fcγ receptor binding, antibody-dependent cell mediated cytotoxicity (ADCC), antibody-dependent cell mediated phagocytosis (ADCP), C1q binding, complement dependent cytotoxicity (CDC), phagocytosis, down regulation of cell surface receptors (e.g. B cell receptor); and B cell activation.

The term "epitope" as used herein, refers to the amino acid residues of an antigen, that are bound by an antibody. An epitope can be a linear epitope, a conformational epitope, or a hybrid epitope. The term "epitope" may be used in reference to a structural epitope. A structural epitope, according to some embodiments, may be used to describe the region of an antigen which is covered by an antibody (e.g., an antibody's footprint when bound to the antigen). In some embodiments, a structural epitope may describe the amino acid residues of the antigen that are within a specified proximity (e.g., within a specified number of Angstroms) of an amino acid residue of the antibody. The term "epitope" may also be used in reference to a functional epitope. A functional epitope, according to some embodiments, may be used to describe amino acid residues of the antigen that interact with amino acid residues of the antibody in a manner contributing to the binding energy between the antigen and the antibody. An epitope can be determined according to different experimental techniques, also called "epitope mapping techniques." It is understood that the determination of an epitope may vary based on the different epitope mapping techniques used and may also vary with the different experimental conditions used, e.g., due to the conformational changes or cleavages of the antigen induced by specific experimental conditions. Epitope mapping techniques are known in the art (e.g., Rockberg and Nilvebrant, *Epitope Mapping Protocols: Methods in Molecular Biology*, Humana Press, 3$^{rd}$ ed. 2018; Holst et al., *Molecular Pharmacology* 1998, 53(1): 166-175), including but not limited to, X-ray crystallography, nuclear magnetic resonance (NMR) spectroscopy, site-directed mutagenesis, species swap mutagenesis, alanine-scanning mutagenesis, steric hindrance mutagenesis, hydrogen-deuterium exchange (HDX), and cross-blocking assays.

The terms "bind" and "binds" as used herein, are intended to mean, unless indicated otherwise, the ability of a protein or molecule to form a chemical bond or attractive interaction with another protein or molecule, which results in proximity of the two proteins or molecules as determined by common methods known in the art.

The terms "nucleic acid" as used herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction.

The term "subject" as used herein, refers to a mammal, including, but are not limited to, a human, chimpanzee, ape, monkey, cattle, horse, sheep, goat, swine, rabbit, dog, cat, rat, mouse, guinea pig, and the like. Preferably, the subject is a human.

The term "therapeutically effective amount", as used herein, refers to an amount of a protein or nucleic acid or vector or composition which, upon single or multiple dose administration to the subject, provides the desired effect in the subject under diagnosis or treatment. The term "therapeutically effective amount", as used herein, further refers to an amount or dose of a protein or nucleic acid or vector or composition of the disclosure, that will elicit the biological or medical response of a subject, for example, reduction or inhibition of an enzyme or a protein activity, or ameliorate symptoms, alleviate conditions, slow or delay disease progression, or prevent a disease, etc. In a non-limiting embodiment, the term "a therapeutically effective amount" refers to the amount (at dosages and for periods of time and for the means of administration) of a protein or nucleic acid or vector or composition that, when administered to a subject, is effective to at least partially alleviate, inhibit, prevent and/or ameliorate a condition, or a disorder or a disease. An effective amount of the protein or nucleic acid or vector or composition may vary according to factors such as the disease state, age, sex, and weight of the individual, and the ability of the protein or nucleic acid or vector or composition to elicit a desired response in the individual. An effective amount is also one in which any toxic or detrimental effects of the protein or nucleic acid or vector or composition of the present invention are outweighed by the therapeutically beneficial effects.

The term "inhibits" as used herein, refers to for example, a reduction, lowering, slowing, decreasing, stopping, disrupting, abrogating, antagonizing, or blocking of a biological response or activity, but does not necessarily indicate a total elimination of a biological response.

The term "treatment" or "treating" as used herein, refers to all processes wherein there may be a slowing, controlling, delaying or stopping of the progression of the disorders or disease disclosed herein, or ameliorating disorder or disease symptoms, but does not necessarily indicate a total elimination of all disorder or disease symptoms. Treatment includes administration of a protein or nucleic acid or vector or composition for treatment of a disease or condition in a patient, particularly in a human.

The term "about" as used herein, means within 5%.

As used herein, the term "a", "an", "the", and similar terms used in the context of the present disclosure (especially in the context of the claims) are to be construed to cover both the singular and plural unless otherwise indicated herein or clearly contradicted by the context.

"Chemotherapeutic agent" or "chemotherapeutic" as used interchangeably herein, is a chemical agent or drug that is selectively destructive to cancer cells and tissues. Chemotherapeutic agent may include but is not limited to compounds such as, taxane compounds, compounds that act via taxane mechanisms, platinum compounds, anthracycline compounds, antimetabolites, alkylating agents, epipodophyllotoxin compounds, camptothecin compounds, topoisomerase inhibitors, mitotic inhibitors, or any combination thereof. Chemotherapeutic agents can be administered alone or in combination with other therapeutic agents.

The term "ionizing radiation" as used herein, is radiation of certain wavelengths used to destroy or damage cancer cells. Ionizing radiation includes radon, x-rays, gamma rays, and other forms of high-energy radiation. Ionizing radiation may include external radiation (or external beam radiation), internal radiation (or brachytherapy) or systemic radiation.

EXAMPLES

Figure 1:
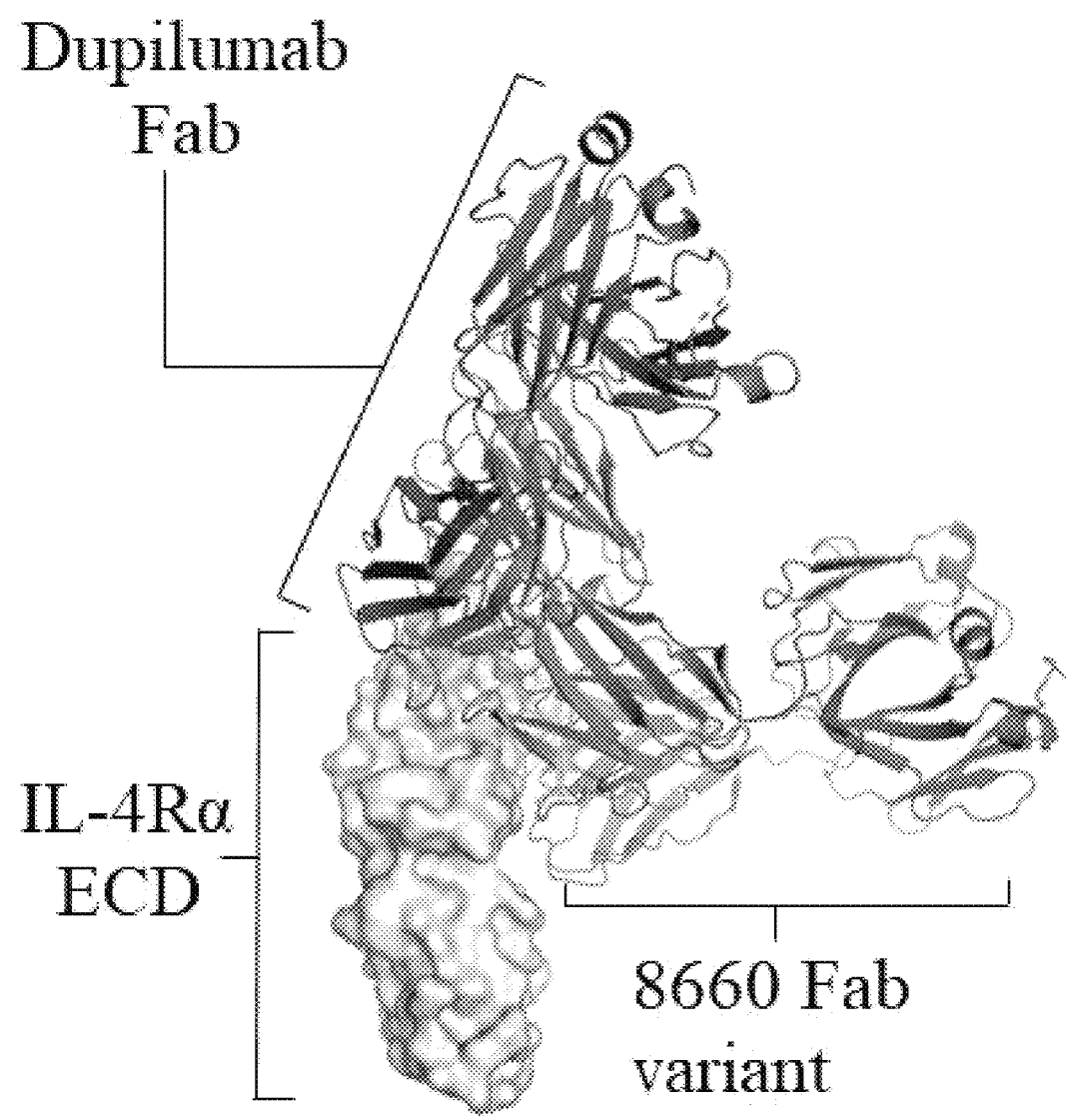
FIG. 1 shows X-ray crystal structure overlay of a Fab portion of the 8660 human IL-4Rα antibody bound to IL-4Rα ECD with the crystal structure of a dupilumab Fab portion with Crystal Kappa design complexed with human IL-4Rα (pdb accession code 6WGL).

Example 1: Generation and Enineering of Antibodies that Bind Human IL-4Rα (Anti-Human IL-4Rα Antibodies)

Antibody generation: To develop antibodies specific to human IL-4Rα, transgenic mice with human immunoglobulin variable regions were immunized with Fc-tagged extracellular domain (ECD) of human IL-4Rα and boosted, alternately, with human and cynomolgus monkey Fc-tagged IL-4Rα ECD proteins. Screening was done with histidine-tagged human and cynomolgus monkey IL-4Rα ECD to identify cross reactivity and in the absence or presence of excess soluble IL-4 to identify IL-4 blocking antibodies. Cross reactive antibodies were cloned as Fabs, expressed, and purified by standard procedures, and tested in a reporter cell line, Human Embryonic Kidney (HEK)-Blue IL-4/IL-13 (InvivoGen) for blocking activity to IL-4 and IL-13. Antibodies were selected and engineered in their CDRs, variable domain framework regions, and IgG isotype to improve characteristics such as, affinity, stability, solubility, viscosity, hydrophobicity, as well as reduced aggregation.

The amino acid sequence of human IL-4Rα ECD is provided by SEQ ID NO: 15, the amino acid sequence of cynomolgus monkey IL-4Rα ECD is provided by SEQ ID NO: 16, the amino acid sequence of human IL-4 is provided by SEQ ID NO: 17, and the amino acid sequence of human IL-13 is provided by SEQ ID NO:18.

The antibodies of the invention can be synthesized and purified by well-known methods. An appropriate host cell, such as Chinese hamster ovarian cells (CHO), can be either transiently or stably transfected with an expression system for secreting antibodies using a predetermined HC:LC vector ratio if two vectors are used, or a single vector system encoding both heavy chain and light chain. Clarified media, into which the antibody has been secreted, can be purified using the commonly used techniques.

Antibody engineering of the IL-4Rα antibodies: IL-4Rα antibody 5F3 IgG4PAA was engineered as a Fab in mammalian cell expression vectors using a high-throughput, site-specific, saturation mutagenesis protocol to find mutations that improve affinity and/or biophysical properties (such as, thermal, chemical stability, or solubility, reduce aggregation or hydrophobicity). The 5F3 IgG4PAA comprises amino acid residue substitutions F234A and L235A in the IgG4 Fcγ region, which reduce binding to the FcγR, and an amino acid substitution S228P, which stabilizes the hinge and prevents arm exchange.

Briefly for the engineering, every amino acid in the CDRs of both the VL and VH chains of the 5F3 IgG4PAA was mutated in individual mutagenesis reactions generating a total of 18 variants (excepting cysteine), as well as back to the original amino acid residue (constituting an embedded wild-type control, WT), using a series of forward and reverse oligo's arrayed in a 384-microtiter plate. Site-directed mutagenesis reactions were carried out according to established procedures and digestion of the WT plasmid was accomplished by incubation with the DpnI restriction enzyme. Digestion products were transformed into *E. coli* and DNA isolated from the bulk transformants following incubation overnight at 37° C. DNA from each individual VL and VH mutagenesis reaction was mixed with the appropriate WT antibody variable region and expressed in CHO cells in a 96-deep well plate. Secreted antibodies were quantified and normalized to a consistent titer prior to screening for binding to IL4Rα in an ELISA format with or without a thermal challenge step. In addition to assessing the CDR mutants, mutants that convert atypical germline residues in the framework regions to the more typical amino acids were similarly assessed.

Hits were confirmed by ELISA titrations, Octet, or Biacore8K and then guided by structure-based considerations were selected, combined, and introduced into a full-length antibody format and assessed for affinity and biophysical properties using butyl-HIC, heparin, column interaction and size exclusion chromatography, differential scanning calorimetry, and serum protein binding by mass spectrometry.

Affinity binding analysis showed that the 5F3 IgG4PAA antibody has a moderate affinity for human and cynomolgus monkey IL-4Rα, with a $K_D$ in the $10^{-9}$ M range. Mutagenesis of the CDR amino acid residues in the 5F3 IgG4PAA identified CDR substitutions: LCDR3 H91W, N92S, which significantly improved affinity of the resulting antibody to the $10^{-11}$ M range.

Furthermore, amino acid residue substitutions leading to improved thermal stability in the thermal challenge ELISA were also identified: VH: A23V, N92S, 131H; VL: G28D. Additionally, amino acid residue substitutions: VH: A23V, I58V; VL: G28D were found to reduce self-association and hydrophobicity while maintaining affinity. Amino acid residue substitution: VH: 131H was found to reduce serum protein binding.

Additionally, the 5F3 IgG4PAA antibody contains an asparagine in the HC Framework 3 (N72) that deamidates under stressful conditions. The N72 amino acid residue was substituted for the more germline Asp (N72D) which resulted in eliminating deamidation.

The mutagenesis analysis of the 5F3 IgG4PAA identified 7 amino acid residues for engineering. These 7 amino acid residues were substituted as follows: 131H, I58V, N72D in the VH region and H91W and N92S in the VL region combined to generate the 8660 antibody variant; and in addition to these 5 substitutions, A23V in the VH region and G28D in the VL region were added to generate the 5559 antibody variants. Table 1 shows the CDR amino acid sequences of the exemplified antibodies.

Several versions of the 5559 and 8660 antibodies with different IgG backbones were generated including those as provided in Tables 2. The engineering of the 7 amino acid residues resulted in the 5559 antibody variants having significantly improved affinity, and other biophysical properties such as, thermal stability, reduced self-association, hydrophobicity, and/or serum protein binding, whilst maintaining affinity.

Antibody constant region engineering to improve viscosity: The 5559 IgG4 human IL-4Rα antibody heavy chain constant region was engineered through charge balancing to improve viscosity and mitigate potential electrostatic interaction between the Fab and constant domains of the antibody. The CH1, CH2, and CH3 domains in the HC constant region of human IgG4 antibodies when compared to the human IgG1 HC constant region, have lower isoelectric points (pI), due to an uneven charge distribution. Accordingly, five key amino acid residues in the CH1, CH2, and CH3 domains impacting the viscosity of the 5559 IgG4 antibodies were identified: 1) E137 (CH1 domain), 2) D203 (CH1 domain), 3) Q274 (CH2 domain), 4) Q355 (CH3 domain), and 5) E419 (CH3 domain). The analogous position in a hIgG1 constant region for these 5 amino acids are different and were found to impact the overall pI of each domain.

To match the pI for the CH2 and CH3 domains of an IgG4 antibody to an IgG1 antibody and to minimize the potential introduction of an immunogenic peptide, the residues at three of the five identified positions in the IgG4 constant region were converted to the corresponding residue found in an IgG1 constant region. The amino acid residue substitutions included: a positively charged lysine substituted for the neutrally charged glutamine at position 274 (Q274K), a positively charged arginine substituted for the neutrally charged glutamine at position 355 (Q355R) and a neutrally charged glutamine substituted for the negatively charged glutamic acid at position 419 (E419Q). The resulting IgG4 Fcγ was termed "KRQ".

An IgG4 constant region comprising substitutions at all 5 identified amino acid residues with those found in the IgG1 (E137G, D203N, Q274K, Q355R, and E419Q) was also constructed, termed "GNKRQ".

The IgG4 KRQ and IgG4 GNKRQ antibody also included the S228P mutation, which stabilizes the hinge and prevents arm exchange, termed IgG4P. A wild type IgG4 CH1 domain along with a human kappa constant domain were used to complete the construct. The antibodies were synthesized, expressed, and purified essentially as described above.

Selection of the IgG4P or IgG1A backbone: The human IgG1A and/or human IgG4P backbone were selected for the exemplified 5559 antibodies because of an unexpected binding property to B cells and myeloid cells. As demonstrated in Table 5B and FIG. 4C, the exemplified 5559 IgG4P and 5559 IgG1A IL-4Rα antibodies were found to have greater binding affinity to B cells, when compared to the 5559 IgG1AAA effector null antibody, thus indicating that the Fcγ portion of the 5559 antibody that is not engineered to be effector null positively impacted on B cell binding.

TABLE 1

CDR amino acid sequences of exemplified human IL-4Rα antibodies

| IL-4Rα Antibody | CDR Sequence | | | | | |
|---|---|---|---|---|---|---|
| | HCDR1 | HCDR2 | HCDR3 | LCDR1 | LCDR2 | LCDR3 |
| 5F3 IgG4PAA | SEQ ID NO: 19 | SEQ ID NO: 20 | SEQ ID NO: 3 | SEQ ID NO: 22 | SEQ ID NO: 5 | SEQ ID NO: 24 |
| 5559 (all variants) | SEQ ID NO: 1 | SEQ ID NO: 2 | SEQ ID NO: 3 | SEQ ID NO: 4 | SEQ ID NO: 5 | SEQ ID NO: 6 |
| 8660 (all variants) | SEQ ID NO: 42 | SEQ ID NO: 2 | SEQ ID NO: 3 | SEQ ID NO: 22 | SEQ ID NO: 5 | SEQ ID NO: 6 |

TABLE 2

Amino Acid sequences of exemplified human IL-4Rα antibodies

| IL-4Rα Antibody | HC | LC | VH | VL |
|---|---|---|---|---|
| 5F3 IgG4PAA | SEQ ID NO: 27 | SEQ ID NO: 28 | SEQ ID NO: 25 | SEQ ID NO: 26 |
| 5559 IgG1A | SEQ ID NO: 33 | SEQ ID NO: 10 | SEQ ID NO: 7 | SEQ ID NO: 8 |
| 5559 IgG1A 124C/378C | SEQ ID NO: 9 | SEQ ID NO: 10 | SEQ ID NO: 7 | SEQ ID NO: 8 |
| 5559 IgG4P | SEQ ID NO: 37 | SEQ ID NO: 10 | SEQ ID NO: 7 | SEQ ID NO: 8 |
| 5559 IgG4P 124C/378C | SEQ ID NO: 31 | SEQ ID NO: 10 | SEQ ID NO: 7 | SEQ ID NO: 8 |
| 5559 IgG4P KRQ | SEQ ID NO: 35 | SEQ ID NO: 10 | SEQ ID NO: 7 | SEQ ID NO: 8 |
| 5559 IgG4P KRQ 124C/378C | SEQ ID NO: 13 | SEQ ID NO: 10 | SEQ ID NO: 7 | SEQ ID NO: 8 |
| 5559 IgG4P GNKRQ 124C/378C | SEQ ID NO: 50 | SEQ ID NO: 10 | SEQ ID NO: 7 | SEQ ID NO: 8 |
| 5559 IgG1AAA 124C/378C | SEQ ID NO: 52 | SEQ ID NO: 10 | SEQ ID NO: 7 | SEQ ID NO: 8 |
| 8660 IgG4P 124C/378C | SEQ ID NO: 46 | SEQ ID NO: 47 | SEQ ID NO: 44 | SEQ ID NO: 45 |

Example 2: Structural and Functional Epitope of the Human IL-4Rα Antibodies

The structural epitope of the exemplified anti-IL-4Rα antibodies was determined by X-ray crystallography and the functional epitope of the exemplified anti-IL-4Rα antibodies was determined by ELISA.

Example 2a. Structural Epitope Determination of the 8660 Fab by X-Ray Crystallography The physical epitope of the Fab of the 8660 anti-IL-4Rα antibody on human IL-4Rα was determined by identifying the interacting interfaces between human IL-4Rα and the exemplified antibodies. Briefly, to determine the structural epitope, human IL-4Rα ECD was co-crystallized with a Fab portion of 8660. The structure of the 8660 Fab complexed with IL-4Rα was determined by creating a hexahistidine tagged IgG1 variant of the heavy chain truncated after the CH1 domain and the "Crystal Kappa" version of the light chain of the 8660 Fab (see, Lieu et al., "Rapid and Robust Antibody Fab Fragment Crystallization Utilizing Edge-to-edge Beta-sheet Packing," *PLoS One*, 15(9) (2020), which is herein incorporated by reference in its entirety). The 8660 variant was co-expressed with a hexahistidine tagged version of human IL-4Rα ECD containing a C182L mutation, the complex was then purified by immobilized metal affinity chromatography and screened using standard commercially available screens for crystallization. Crystals were obtained and x-ray diffraction data was collected at the Advanced Photon Source. The diffraction data was reduced and solved by molecular replacement and refined to yield a 2.8 Å structure of the exemplified 8660 Fab and IL-4Rα ECD complex. From the resulting crystal structure, any IL-4Rα amino acid residues within 4.5 Å of an atom of the co-crystallized 8660 Fab was counted as part of the epitope (using PyMOL visualization software [Schrödinger®]).

The PyMOL analysis demonstrated that the IL-4Rα amino acid residues (with respect to SEQ ID NO: 15) that are within 4.5 Å of the 8660 Fab in the crystal structure complex comprise of the structural epitope for the exemplified antibodies. Specifically, the analysis determined the structural epitope comprises the following amino acid residues: Asp at position 12, Met at position 14, Ser at position 15, Ile at position 16, Tyr at position 37, Leu at position 39, Phe at position 41, Leu at position 43, Glu at position 45, His at position 47, Thr at position 48, Cys at position 49, Ile at position 50, His at position 62, Leu at position 64, Met at position 65, Asp at position 66, Asp at position 67, Val at position 69, Asp at position 72, Arg at position 99, Pro at position 121, Pro at position 123, Pro at position 124, Asp at position 125. The analysis further determined that the structural epitope spans domains 1 and 2 of the N-terminus fibronectin type-III domain of the IL-4Rα. Furthermore, the analysis determined that the following amino acid residues of the structural epitope are located in domain 2 of the N-terminal fibronectin type-III domains of the IL-4Rα: R99, P121, P123, P124, D125.

In addition, overlay of the exemplified 8660 Fab and the crystal structure of a dupilumab Fab with the crystal kappa design complexed with human IL-4Rα (pdb accession code 6WGL) indicated that the 8660 Fab bound to a novel epitope on IL-4Rα when compared to dupilumab (FIG. 1).

Furthermore, an alignment of the exemplified IL-4Rα 8660 Fab:IL-4Rα complex crystal structure with published complexes of IL-4 and IL-13 and their respective receptors (pdb accession codes 3BPN and 3BPO) on the IL-4Rα component in each structure (using PyMOL visualization software) showed that the exemplified 8660 Fab antibody epitope overlapped with both the IL-4 and the IL-13 binding sites to IL-4Rα, thus indicating that binding of the exemplified antibodies to IL-4Rα would physically block the IL-4 and IL-13 cytokines from binding to IL-4Rα when the Fab variant portion of the exemplified antibodies is bound to IL-4Rα.

Example 2b. Functional Epitope Determination of the 5F3 IgG4PAA

The functional epitope of the exemplified human IL-4Rα antibody 5F3 IgG4PAA was determined by ELISA. Briefly, thirty surface amino acid residue substitutions were introduced individually into hexahistidine tagged human IL-4Rα extra cellular domain (ECD) as follows: K2D, E6R, K22D, P26R, T31R, F41A, L42G, L43G, E45R, G56R, D66R, A71R, Q82G, K87D, E94R, H107A, D108R, P124R, D125R, D143R, R148D, L155R, R160D, S164R, S168R, Q181R, P192R, K195D, or H197G. Each mutant protein having a single amino acid residue substitution as described above was transiently expressed in CHO cells and purified using standard immobilized metal affinity chromatography techniques. ELISA plates were coated with 1 µg/mL goat anti-human kappa antibody (Southern Biotech, Cat #2060-01) in PBS at 4° C. overnight, then washed 3 times in PBST and blocked with PBS casein for 30 min at room temperature. The plates were then washed 3 times with PBST and the exemplified human IL-4Rα antibody 5F3 IgG4PAA was added to the wells at a final concentration of 1 µg/mL in PBS-casein and incubated for 1 hour. The plates were washed 3 times with PBST, the IL-4Rα mutant proteins were serially diluted 3-fold from 1 µg/mL in PBS-casein and added to the plate at 50 µL/well and incubated for 1 hour at room temperature. The plates were washed 3 times with PBST and a 5000-fold dilution of anti-histidine tag antibody HRP conjugate (R&D Systems, Cat. # MAB050H) in PBS-casein was added and incubated for 1 hour at room temperature. The plates were washed 3 times, TMB substrate (Pierce, Cat. #34021) was added per manufacturer instructions, the reaction was quenched with $H_2SO_4$, and absorbance was read at 450 nm on an ELISA plate reader. The functional epitope of the antibody was determined as the mutated amino acid residues corresponding to the wells that showed no binding signal or showed a significantly reduced binding signal when compared to the control antibodies.

Figure 2:
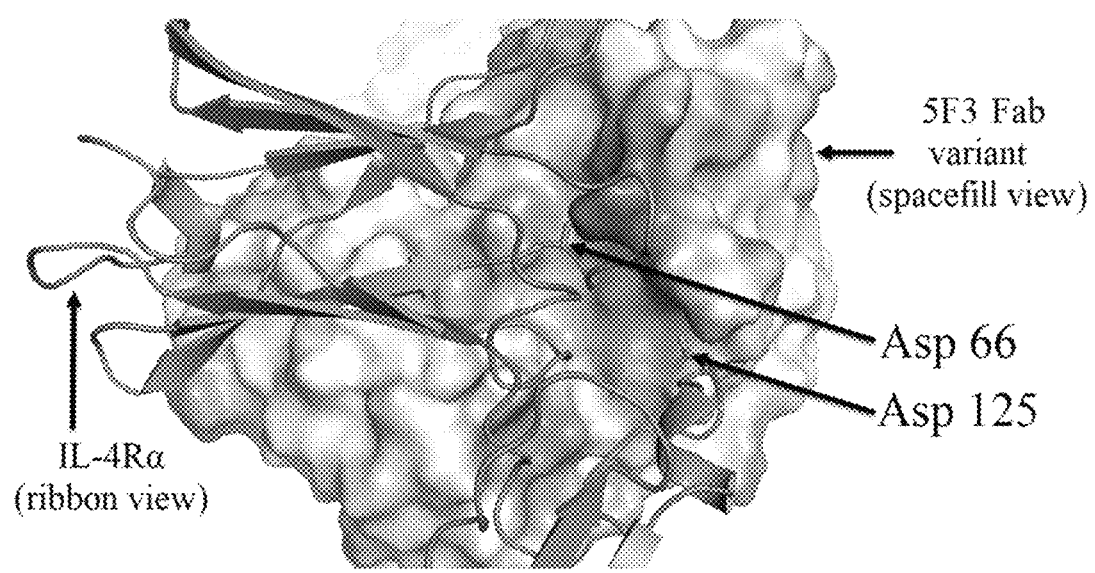
FIG. 2 shows the functional epitope amino acid residue locations (human IL-4Rα residues Asp66 and Asp125) in the crystal structure of 5F3 Fab portion with Crystal Kappa design complexed with human IL-4Rα ECD.
Figure 3A:
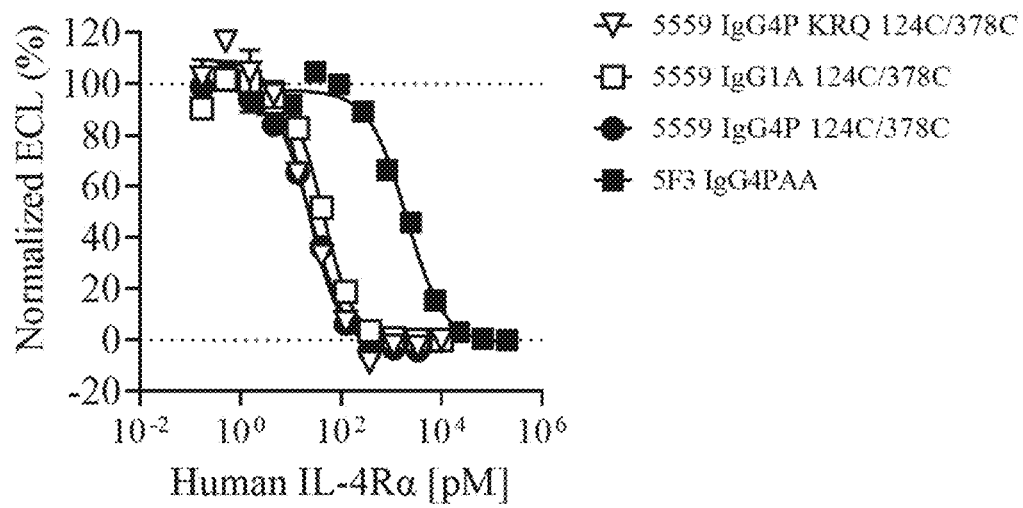
FIGS. 3A-3B show the binding specificity of the 5F3 and 5559 human IL-4Rα antibodies to human IL-4Rα (3A) and Cynomolgus monkey IL-4Rα (3B) as measured by MSD ELISA assay.
Figure 3B:
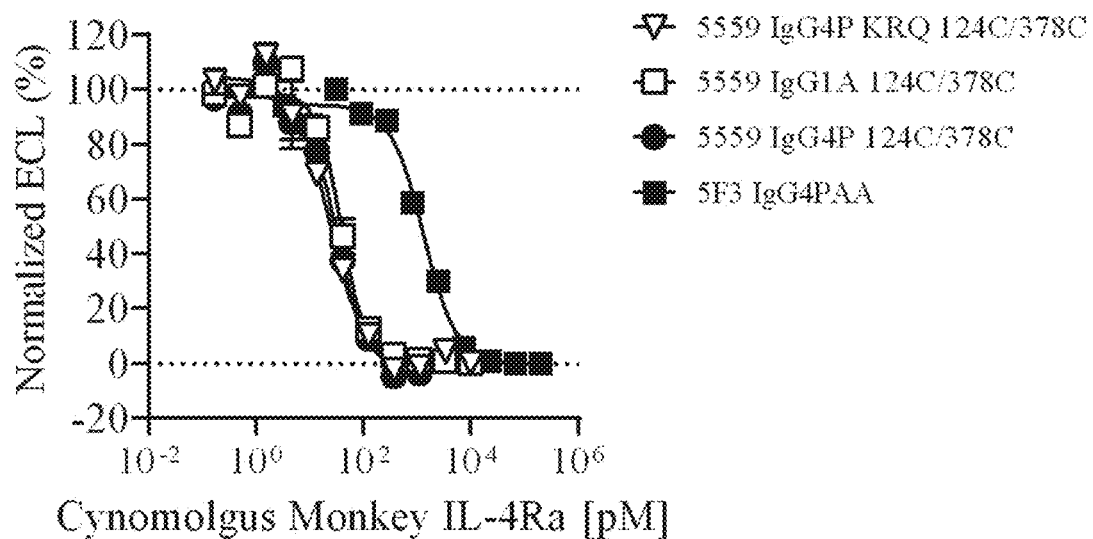

The results as demonstrated in Table 3, show that the functional epitope for the exemplified 5F3 IgG4PAA antibody comprises amino acid residues D66 and D125. Among the amino acid residues identified in the structural epitope, amino acid residue substitutions of D66R and D125R on the IL-4Rα displayed a significantly negative impact on binding of the exemplified 5F3 IgG4PAA to the mutated IL-4Rα respectively. Specifically, substitution of amino acid residue D66 of the IL-4Rα to Arginine reduced binding of the 5F3 IgG4PAA to the mutated IL-4Rα to below that of the control (0.04 $OD_{450}$ and 0.14 $OD_{450}$, respectively). Furthermore, substitution of amino acid residue D125 to Arginine, which is located near amino acid residue D66 on the crystal structure of the IL-4Rα (see FIG. 2), also showed significantly reduced binding of 0.59 $OD_{450}$.

The remaining amino acid substitutions were either within the range of positive binding or outside of the determined structural epitope.

TABLE 3a

| Functional epitope determination of exemplified human IL-4Rα antibodies | |
|---|---|
| Amino acid substitution | ELISA ($OD_{450}$) |
| K2D | 1.48 |
| E6R | 1.08 |
| K22D | 0.64 |
| P26R | 1.40 |
| T31R | 1.61 |
| F41A | 1.53 |
| L42G | 1.20 |
| L43G | 1.69 |
| E45R | 1.15 |
| G56R | 1.43 |
| D66R | 0.04 |
| A71R | 1.35 |
| Q82G | 1.59 |
| K87D | 1.16 |
| E94R | 1.46 |
| H107A | 1.54 |
| T108R | 1.21 |
| V110R | 1.47 |
| P124R | 1.35 |
| D125R | 0.59 |
| D143R | 1.51 |
| R148D | 1.39 |
| L155R | 1.53 |
| R160D | 1.54 |
| S164R | 1.56 |
| S168R | 1.53 |
| Q181R | 1.30 |
| P192R | 1.33 |
| K195D | 1.06 |
| H197G | 1.02 |
| Buffer Control (no receptor) | 0.14 |

Example 2c: Structural Epitope of the Human IL-4Rα 5559 Antibodies

Structural epitope determination of the 5559 Fab by X-ray crystallography. The physical epitope of the Fab of the 5559 antibody on human IL-4Rα was determined by essentially as described above. Crystals were obtained and x-ray diffraction data was collected at the Advanced Photon Source. The diffraction data was reduced and solved by molecular replacement and refined to yield a 2.49 Å structure of the exemplified 5559 Fab and IL-4Rα ECD complex. From the resulting crystal structure, any IL-4Rα amino acid residues within 4.5 Å of an atom of the co-crystallized 5559 Fab was counted as part of the epitope (using Molecular Operating Environment (MOE) visualization, modeling and simulations software [Chemical Computing Group], Coot (General Public License) and PyMOL visualization software [Schrödinger®]).

The MOE, Coot, and PyMOL analysis demonstrated that the IL-4Rα amino acid residues (with respect to SEQ ID NO: 15) that are within 4.5 Å of the 5559 Fab in the crystal structure complex comprise of the structural epitope. Specifically, the analysis determined the structural epitope comprises the following amino acid residues: Asp at position 12, Met at position 14, Ser at position 15, Ile at position 16, Leu at position 39, Phe at position 41, Leu at position 42, Thr at position 48, Cys at position 49, Ile at position 50, Glu at position 52, His at position 62, Leu at position 64, Met at position 65, Asp at position 66, Asp at position 67, Val at position 68, Val at position 69, Asp at position 72, Arg at position 99, Pro at position 121, Pro at position 123, Pro at position 124, Asp at position 125, Pro at position 192. Asp at position 66 was well coordinated having interactions between 2.6-2.9 Å with the heavy chain of the 5559 Fab. Asp at position 67 had longer range interactions between 3.1-3.5 Å and demonstrated flexibility in its binding position, as evidenced by the observance of excess density around its sidechain. The analysis determined that the structural epitope spans domains 1 and 2 of the N-terminus fibronectin type-III domain of the IL-4Rα. Furthermore, the analysis determined that the following amino acid residues of the structural epitope are located in domain 2 of the N-terminal fibronectin type-III domains of the IL-4Rα: R99, P121, P123, P124, D125, P192.

Overlay of the exemplified 5559 Fab and the crystal structure of a dupilumab Fab with the crystal kappa design complexed with human IL-4Rα (pdb accession code 6WGL) showed that the 5559 Fab bound to a novel epitope on IL-4Rα when compared to dupilumab (FIG. 13).

Alignment of the exemplified IL-4Rα 5559 Fab:IL-4Rα complex crystal structure with published complexes of IL-4 and IL-13 and their respective receptors (pdb accession codes 3BPN and 3BPO) on the IL-4Rα in each structure (using PyMOL visualization software) showed that the exemplified 5559 Fab antibody epitope overlapped with both the IL-4 and the IL-13 binding sites to IL-4Rα. This indicated that binding of the exemplified 5559 antibodies would physically block the IL-4 and IL-13 cytokines from binding to IL-4Rα.

Example 2d. Functional Epitope Determination of the Human IL-4Rα 5559 Antibodies The functional epitope of the exemplified human IL-4Rα antibody 5559 IgG4P KRQ was determined by ELISA. Briefly, thirty surface amino acid residue substitutions were introduced individually into hexahistidine tagged human IL-4Rα extra cellular domain (ECD) as follows: K2D, E6R, K22D, P26R, T31R, F41A, L42G, L43G, E45R, E52R, G56R, D66R, A71R, Q82G, K87D, E94R, H107A, D108R, P124R, D125R, D143R, R148D, L155R, R160D, S164R, S168R, Q181R, P192R, K195D, or H197G. Each mutant protein having a single amino acid residue substitution as described above was transiently expressed in CHO cells and purified using standard immobilized metal affinity chromatography techniques. ELISA plates were coated with 1 μg/mL goat anti-human IgG Fc antibody (Jackson ImmunoResearch Laboratories, Cat #109-005-098) in PBS at 4° C. overnight, then washed 3 times in PBST and blocked with PBS casein for 1 hour at room temperature. The plates were then washed 3 times with PBST and the exemplified human IL-4Rα antibody 5559 IgG4P KRQ was added to the wells at a final concentration of 1 μg/mL in PBS-casein and incubated for 1 hour at room temperature. The plates were washed 3 times with PBST, the IL-4Rα mutant proteins were serially diluted 5-fold from 1 μg/mL for 3 points. in PBS-casein and added to the plate at 50 L/well and incubated for 1 hour at room temperature. The plates were washed 3 times with PBST and a 1000-fold dilution of anti-histidine tag antibody HRP conjugate (R&D Systems, Cat. # MAB050H) in PBS-casein was added and incubated for 45 minutes at room temperature. The plates were washed 3 times, TMB substrate (Pierce, Cat. #34028) was added per manufacturer instructions, the reaction was quenched with $H_2SO_4$, and absorbance was read at 450 nm on an ELISA plate reader. The functional epitope of the antibody was determined as the mutated amino acid residues corresponding to the wells that showed no binding signal or showed a significantly reduced binding signal when compared to the wild type control.

The results as demonstrated in Table 4, show that the functional epitope for the exemplified 5559 IgG4P KRQ antibody comprises amino acid residues D66. Amino acid residue substitution of D66 to D66R on the IL-4Rα reduced binding of the 5559 IgG4P KRQ to the D66R IL-4Rα to below that of the negative control (0.047 $OD_{450}$ and 0.063 $OD_{450}$, respectively). Amino acid residue D66 is located near structural epitope residues D67 and D125 in the crystal structure of the IL-4Rα (FIG. 14). The remaining amino acid substitutions were either within the range of positive binding or outside of the determined structural epitope.

TABLE 3b

Functional epitope determination of exemplified human IL-4Rα 5559 antibodies

| Amino Acid Substitution | 1 μg/mL ELISA ($OD_{450}$) | 0.2 μg/mL ELISA ($OD_{450}$) | 0.04 μg/mL ELISA ($OD_{450}$) |
|---|---|---|---|
| K2D | 2.049 | 1.6064 | 1.0949 |
| E6R | 2.245 | 1.5049 | 0.9155 |
| K22D | 1.668 | 1.2977 | 0.5927 |
| P26R | 1.663 | 1.5241 | 0.8826 |
| T31R | 1.638 | 1.4901 | 0.9938 |
| F41A | 1.765 | 1.5448 | 1.1513 |
| L42G | 1.708 | 1.4848 | 0.9646 |
| L43G | 1.703 | 1.6986 | 1.3486 |
| E45R | 1.699 | 1.8614 | 1.5755 |
| E52R | 1.731 | 1.7126 | 1.0989 |
| G56R | 1.728 | 1.7032 | 1.1731 |
| D66R | 0.047 | 0.0425 | 0.0529 |
| A71R | 1.698 | 1.5651 | 0.9069 |
| Q82G | 1.742 | 1.5318 | 1.1029 |
| K87D | 1.748 | 1.5643 | 0.9115 |
| E94R | 1.733 | 1.6389 | 1.0337 |
| H107A | 1.889 | 1.8353 | 1.422 |
| T108R | 1.883 | 1.8157 | 1.4055 |
| P124R | 1.845 | 1.6964 | 1.1568 |
| D125R | 1.792 | 1.6089 | 1.0142 |
| D143R | 1.754 | 1.6923 | 1.2744 |
| R148D | 1.756 | 1.6005 | 1.0356 |
| L155R | 1.785 | 1.6802 | 1.1405 |
| R160D | 1.905 | 1.6992 | 1.2009 |
| S164R | 1.920 | 1.7747 | 1.4032 |
| S168R | 1.882 | 1.7138 | 1.1808 |
| Q181R | 1.909 | 1.7146 | 1.1669 |
| P192R | 1.939 | 1.749 | 1.2217 |
| K195D | 1.913 | 1.6531 | 0.992 |
| H197G | 1.851 | 1.6017 | 0.9666 |
| Wild type receptor | 1.910 | 1.8555 | 1.6475 |
| Buffer Control (no receptor) | 0.063 | 0.0625 | 0.0625 |

Example 3. Binding Affinity and Functional Activity of the Human IL-4Rα Antibodies Binding affinity: The binding affinity of the exemplified anti-IL-4Rα antibodies to human and cynomolgus monkey IL-4Rα were measured using a competition Meso Scale Discovery (MSD) ELISA binding assay. A constant concentration of each antibody was mixed with a 3-fold dilution series of IL-4Rα to give a final concentration of 10 pM for each 5559 antibody and 100 pM for 5F3 and dilutions starting with 10 nM IL-4Rα for 5559 antibodies and 200 nM IL-4Rα for 5F3 and the mix was incubated at 37° C. for 4 days. A 96-well multi-array plate (Meso Scale Diagnostics, Cat. # L15XA-3) was coated at 4° C. overnight with 0.5 μg/mL hexahistidine-tagged human or cynomolgus monkey IL-4Rα ECD in phosphate buffered saline (PBS). Following coating, plates were washed 10 times with 200 μL PBST (PBS with 0.05% Tween®20) and blocked with 150 μL/well of PBS casein blocking buffer (Pierce, Cat. #37528) at 37° C. for 1 hour. Plates were then washed 10 times as above, and 50 μL of the preincubated antibody:IL-4Rα dilution series was transferred to the wells and incubated at 37° C. with 300 rpm shaking for 150 seconds. Plates were washed 10 times with PBST, 50 μL of 1 μg/mL anti-human antibody sulfo-tag 20 (Meso Scale Diagnostics, Cat. #R32AJ-1) was added, and plates were incubated at 37° C. with 300 rpm shaking for 30 minutes. Plates were washed 10 times with PBST, 150 μL/well of 1× Read Buffer T was added to the wells and analyzed on a SECTOR® Imager 6000 (Meso Scale Diagnostics) 15 min after buffer addition. The apparent KD is determined by fitting a sigmoidal curve to the electrochemiluminescence (ECL) response vs. log(soluble IL-4Rα concentration) using GraphPad Prism 9. Data is graphed with normalized ECL values.

The results as demonstrated in Table 4, and FIGS. 3A and 3B, show that the exemplified 5559 anti-IL-4Rα antibody variants had a significant increase in binding affinity to both human and cynomolgus monkey IL4-Ra when compared to the 5F3 IgG4PAA antibody. Specifically, binding affinity to human IL4-Ra of the respective 5559 antibody variants were 5559 IgG1A 124C/378C (45.08 pM), 5559 IgG4P KRQ 124C/378C (20.82 pM), and 5559 IgG4P 124C/378C (24.63 pM) when compared to the 5F3 IgG4PAA (1993 pM).

TABLE 4

Binding affinities of exemplified human IL-4Rα antibodies to human and cynomolgus monkey IL-4Rα

| IL-4Rα Antibody | IL4-Rα Species | $K_D$ (pM) |
|---|---|---|
| 5F3 IgG4PAA | Human | 1993 |
| | Cynomolgus monkey | 1326 |
| 5559 IgG1A 124C/378C | Human | 45.08 |
| | Cynomolgus monkey | 38.88 |
| 5559 IgG4P KRQ 124C/378C | Human | 20.82 |
| | Cynomolgus monkey | 23.32 |
| 5559 IgG4P 124C/378C | Human | 24.63 |
| | Cynomolgus monkey | 31.52 |

Binding to B cells and T cells: Binding of the exemplified human IL-4Rα antibodies to B cells and T cells was tested in a Fluorescence Activated Cell Sorting (FACS) assay. Human PBMCs were isolated from human blood samples by standard Ficoll-Paque™ plus (GE HEALTHCARE) density gradient centrifugation methods. Freshly isolated cells PBMCs were resuspended at $2\times10^6$ cells/mL and allowed to rest for 15 minutes at room temperature, then plated at 100 μL/well into a round bottom 96-well plate (COSTAR®) and washed with FACS buffer (PBS containing 2% fetal bovine serum from Corning®). Exemplified human IL-4Rα antibodies and the respective control IgG antibodies conjugated to Alexa Fluor© 647 according to manufacturer's protocol (Thermo Fisher Scientific) were added to the wells at 66.67 nM and diluted 4-fold in duplicate. Equivalent volume of 2× antibody cocktail containing: Human TruStain FcX™, FITC anti-human CD3 Antibody, Alexa Fluor® 700 anti-human CD4 Antibody (all from Biolegend®) and CD20 Monoclonal Antibody (2H7), PerCP-Cyanine5.5 (Thermo Fisher Scientific) was then added to the wells. Cells were incubated at 4° C. for 30 minutes, washed twice with FACS buffer and resuspended in a final volume of 100 μL FACS buffer. Viability dye, Sytox™ blue (Thermo Fisher Scientific), was added and the samples were analyzed via a flow cytometer (LSRFortessa™ X-20; BD BIOSCIENCES). Data analysis was performed using FlowJo software and statistical analysis was performed using GraphPad Prism 9. Data represents the mean±SEM of the percentage of IL-4Rα expressing cells from the CD20 B cell and CD4-positive T cell populations from six donors. Curves were generated by fitting a sigmoidal curve of the log(Ab concentration) vs. the percent of positive IL-4Rα expressing cells from the individual cell populations.

Figure 4A:
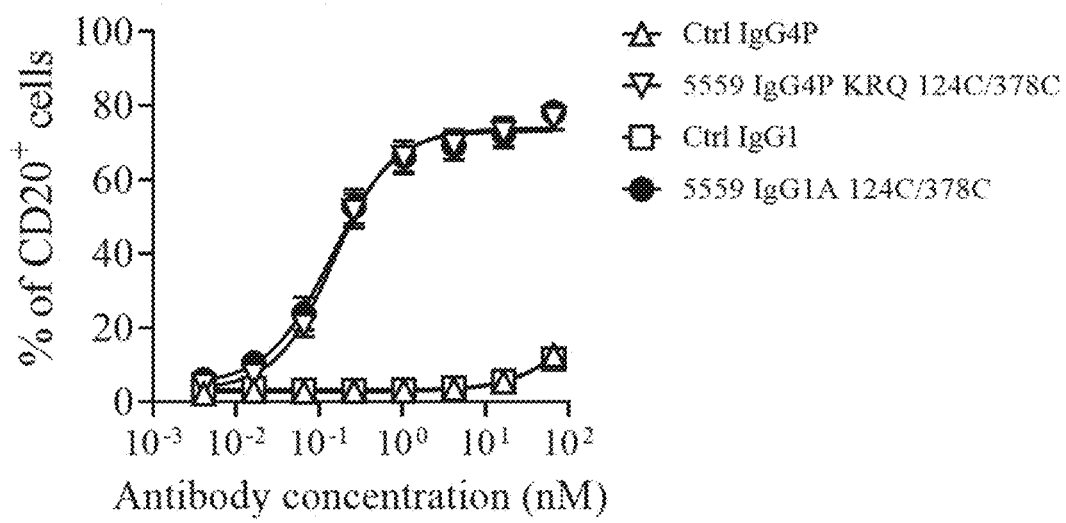
FIGS. 4A-4C show the binding specificity of 5559 human IL-4Rα antibodies to IL-4Rα on human B cells (4A and 4C) and T cells (4B).
Figure 4B:
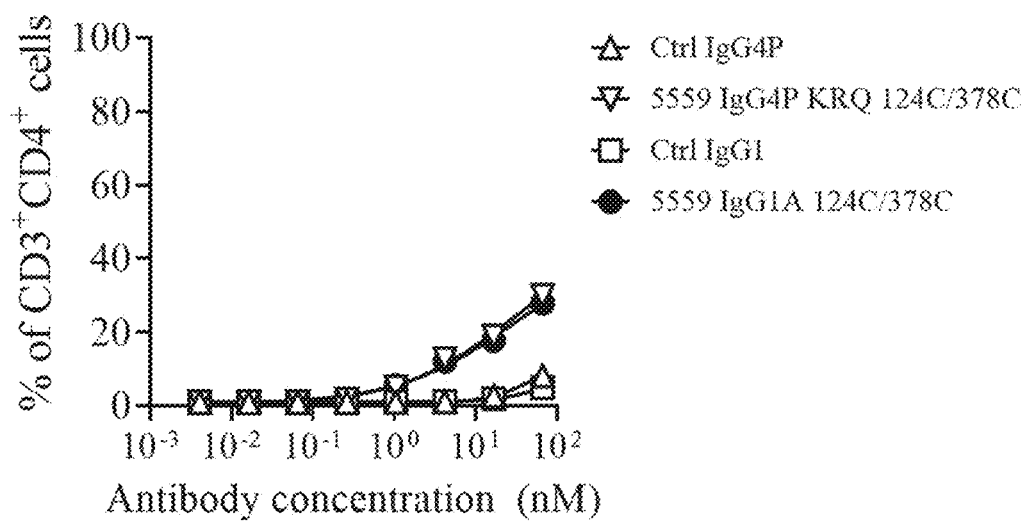

The results as demonstrated in Table 5A, and FIGS. 4A and 4B, show that the exemplified IL-4Rα antibodies 5559 IgG1A 124C/378C and 5559 IgG4P KRQ 124C/378C bound with comparable affinity to the human PBMC isolated B cells ($EC_{50}$ of 0.14 nM and 0.15 nM, respectively) and CD4 T cells ($EC_{50}$ of 28.7 nM and 26.3 nM, respectively). In addition, the results showed that the KRQ amino acid residue substitutions and the 124C/378C amino acid residue substitutions did not impact binding of the exemplified anti-IL-4Rα 5559 antibodies to the B or T cells.

Figure 4C:
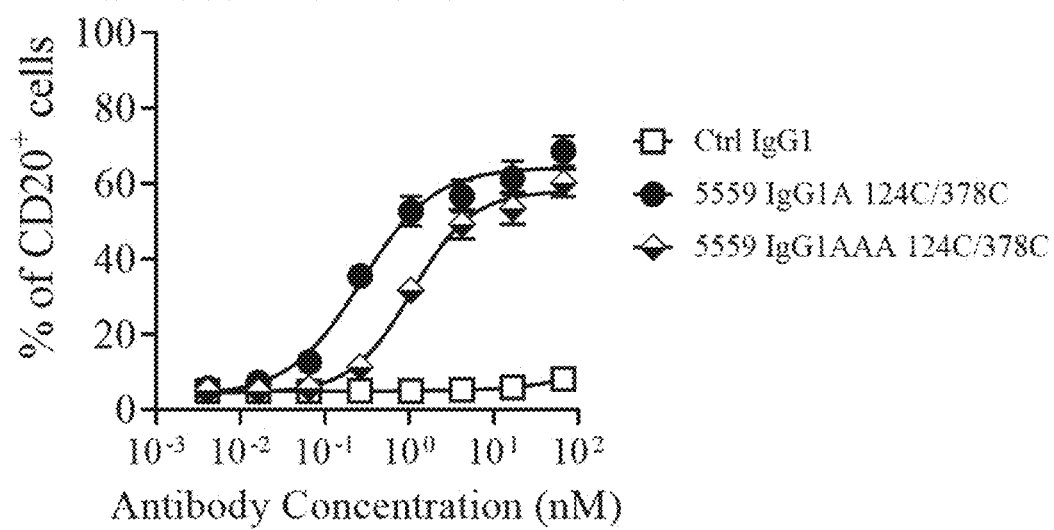

Furthermore, as demonstrated in Table 5B and FIG. 4C, the 5559 IgG1AAA 124C/378C effector null antibody showed unexpectedly reduced affinity to B cells ($EC_{50}$ of 1.07 nM) when compared to the 5559 IgG1A 124C/378C antibody ($EC_{50}$ of 0.27 nM), indicating that the Fc portion of the antibody may impact binding of the exemplified IL-4Rα antibody to B cells.

TABLE 5A

Binding of exemplified human IL-4Rα antibodies to B and T cells

| IL-4Rα Antibody | B Cells $EC_{50}$ (nM) | T Cells $EC_{50}$ (nM) |
|---|---|---|
| 5559 IgG1A 124C/378C | 0.14 | 28.7 |
| 5559 IgG4P KRQ 124C/378C | 0.15 | 26.3 |

TABLE 5B

Binding of exemplified human IL-4Rα antibodies to B cells

| Antibody | B Cells $EC_{50}$ (nM) |
|---|---|
| 5559 IgG1A 124C/378C | 0.27 |
| 5559 IgG1AAA 124C/378C | 1.07 |

Cell based IL-4 and IL-13 cytokine blocking activity: Antagonist activity of the exemplified anti-IL-4Rα antibodies towards IL-4 and IL-13 was conducted with HEK-Blue IL-4R and IL-13R expressing cell line (InvivoGen) by measuring secreted embryonic alkaline phosphatase (SEAP) activity. HEK-Blue cells were plated overnight at $5 \times 10^4$ cells/well in 50 μL of growth media in a poly-lysine coated plate. Exemplified IL-4Rα antibodies (5F3 IgG4PAA, 5559 IgG4P 124C/378C, 5559 IgG4P KRQ 124C/378C, 5559 IgG1A 124C/378C and 8660 IgG4P 124C/378C) were prepared in a Greiner 96-well low protein binding plate at 4-fold dilutions starting from 20 μg/mL in growth media. The dilution series was mixed with an equal volume of either recombinant human IL-4 or IL-13 (Eli Lilly) in growth media. 50 μL of the mixture was then added to the plates with the HEK-Blue cells to a final concentration of 100 pg/mL human IL-4 or 10 ng/mL human IL-13, and plates were then incubated overnight in a tissue culture incubator at 37° C. 20 μL of supernatant from the overnight incubated plates was transferred to a 96-well tissue culture treated plate and 180 μL per well of QUANTI-Blue™ (InvivoGen) is added, and the mixture is incubated for 45 min at 37° C. Secreted embryonic alkaline phosphatase (SEAP) activity was measured by at 650 nm on a SpectraMax microplate reader (Molecular Devices). Results were reported as optical density (OD) at 650 nm and statistical analysis was performed using GraphPad Prism 9. $IC_{50}$, and curves were generated by fitting a sigmoidal curve of the log (Ab concentration) vs. OD at 650 nm for each exemplified antibody.

Figure 5A:
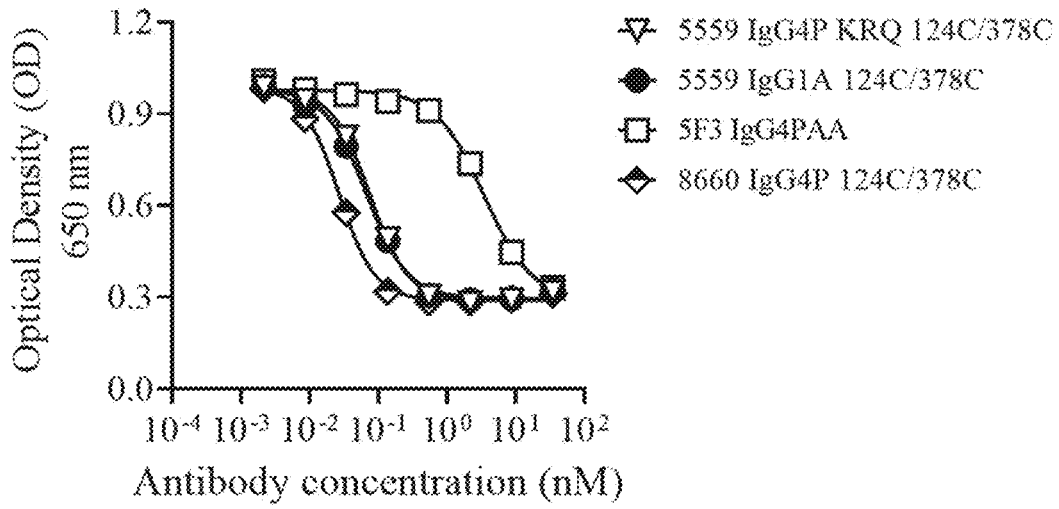
FIGS. 5A-5B show the 5F3, 8660, and 5559 human IL-4Rα antibodies block binding of IL-4 (5A) and IL-13 (5B) to IL-4Rα in a cell-based assay.
Figure 5B:
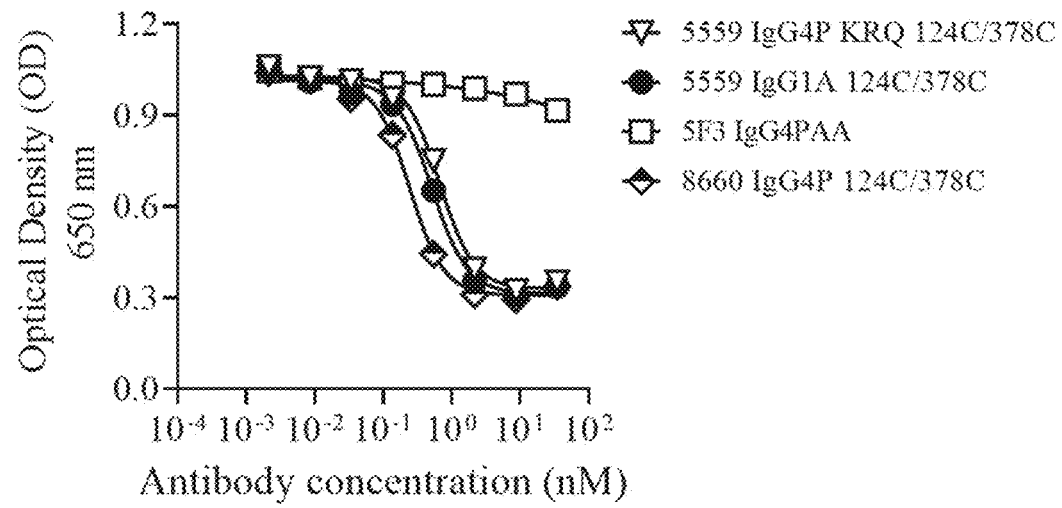

The results as demonstrated in Table 6, and FIGS. 5A and 5B, show that the exemplified IL-4Rα antibodies 5559 IgG1A 124C/378C, 5559 IgG4P KRQ 124C/378C and 8660 IgG4P 124C/378C inhibited both IL-4 (FIG. 5A) and IL-13 (FIG. 5B) induced SEAP activity in a dose dependent manner. Specifically, as shown in Table 6 and FIG. 5A, inhibition of IL-4 induced SEAP activity for the 5559 IgG1A 124C/378C, 5559 IgG4P KRQ 124C/378C, and 8660 IgG4P 124C/378C antibodies resulted in $IC_{50}$ values of 0.07, 0.08 and 0.03 nM, respectively. Furthermore, as shown in Table 6 and FIG. 5B, inhibition of IL-13 induced SEAP activity for the 5559 IgG1A 124C/378C, 5559 IgG4P KRQ 124C/378C and 8660 IgG4P 124C/378C antibodies resulted in comparable $IC_{50}$ values of 0.51, 0.67 and 0.24 nM, respectively.

TABLE 6

Cell based IL-4 and IL-13 blocking activity by exemplified human IL-4Rα antibodies

| IL-4Rα Antibody | IL-4 $IC_{50}$ (nM) | IL-13 $IC_{50}$ (nM) |
|---|---|---|
| 5F3 IgG4PAA | 3.45 | >35 |
| 5559 IgG1A 124C/378C | 0.07 | 0.51 |
| 5559 IgG4P KRQ 124C/378C | 0.08 | 0.67 |
| 8660 IgG4P 124C/378C | 0.03 | 0.24 |

Inhibition of IL-4 and IL-13 induced pSTAT6 phosphorylation in human PBMCs: Inhibition of IL-4 and IL-13 mediated IL-4R pSTAT6 phosphorylation by the exemplified anti-IL-4Rα antibodies was assessed in primary B and/or T cells. Human PBMCs were isolated from human blood samples by standard Ficoll-Paque™ plus (GE HEALTHCARE) density gradient centrifugation methods. Isolated cells were resuspended at 100-300 million cells in 100 mL of complete media (RPMI-1640 with 10% FBS, 1% penicillin-streptomycin solution, from Corning®, and 1% GlutaMAX™ and 0.1% β-mercaptoethanol from Gibco™) in a T175 flask (FALCON) and stimulated with 2 μg/mL PHA (SIGMA), 0.5 μg/mL LPS (SIGMA) and 100 ng/mL recombinant human IL-6 overnight. Cells were washed with fresh media and plated at $5 \times 10^4$ to $2 \times 10^5$ cells/well in 96 well round bottom plates (Corning®) in 100 μL complete media containing the exemplified antibodies at 10 μg/mL diluted down in a 4-fold dilution and 11-point titration. The cells were incubated with the antibodies for 30 minutes at room temperature and then stimulated with 120 ng/mL (6× concentration) of human recombinant IL-4 or human recombinant IL-13 (R&D SYSTEMS) in 20 μL complete media for 12 minutes at room temperature. Stimulation was stopped by the addition of 120 μL of 1× Lyse/Fix Buffer (BD BIOSCIENCES) for 5 minutes, the plates were then centrifuged at 2000 rpm for 2 minutes and the supernatant was aspirated. The cell pellets were resuspended in 100 μL ice-cold methanol (SIGMA) and placed on ice for 20 minutes and washed with DPBS containing 2% FBS (Corning®). The cells were resuspended in 50 μL of antibody cocktail against the following proteins: CD4, CD33, CD8, and CD3 (Thermo Fisher Scientific), phosphorylated STAT6 (Biolegend®) and CD20 (BD BIOSCIENCES) and incubated for 30 minutes at room temperature and then washed with DPBS containing 2% FBS. The cell samples were analyzed using a flow cytometer. Analysis was performed using FlowJo software and statistical analysis is performed using GraphPad Prism 9. Curves were generated by fitting a sigmoidal curve of the log (Ab concentration) vs. the percent inhibition of phosphorylated STAT6 from the individual cell populations from two donors.

Figure 6A:
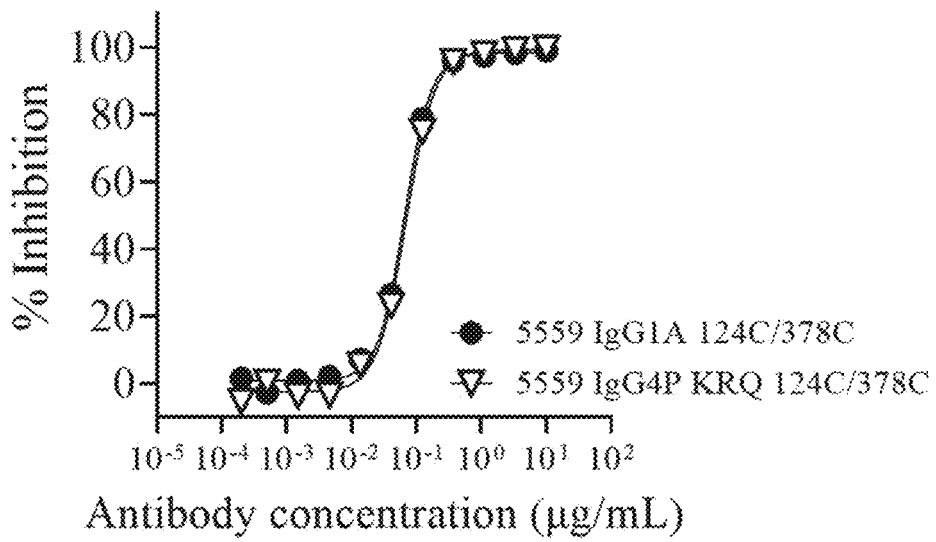
FIGS. 6A-6B show the 5559 human IL-4Rα antibodies inhibit IL-4 induced pSTAT6 phosphorylation in primary human B cells (6B) and T cells (6A).
Figure 6B:
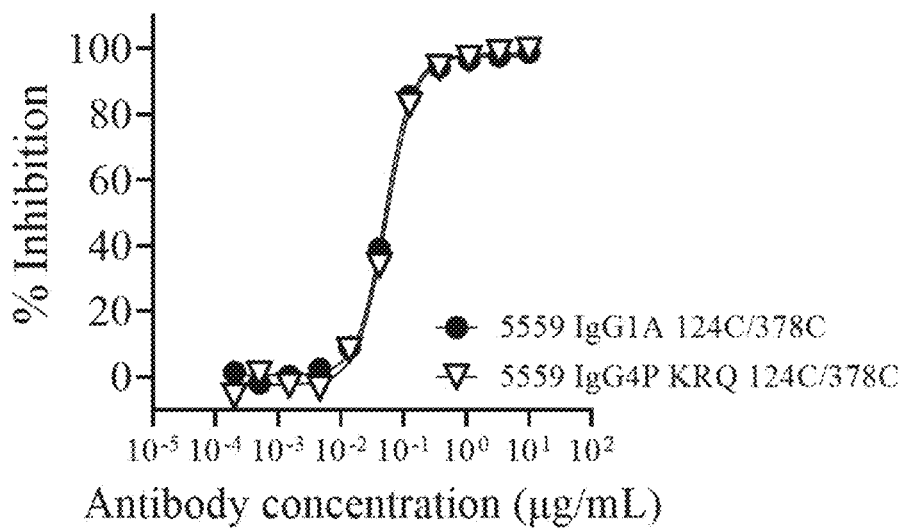

The results as demonstrated in Table 7, and FIGS. 6A and 6B, show that the exemplified IL-4Rα antibodies inhibited IL-4 induced STAT6 phosphorylation in both CD4+ T cells (FIG. 6A) and B cells (FIG. 6B) in a dose dependent manner. Specifically, the $IC_{50}$ values for inhibition of IL-4 induced pSTAT6 phosphorylation by the exemplified 5559 IgG1A 124C/378C and 5559 IgG4P KRQ 124C/378C antibodies was 0.07 μg/mL in the CD4 T cells, and 0.05 μg/mL in the B cells for both antibodies.

Figure 6C:
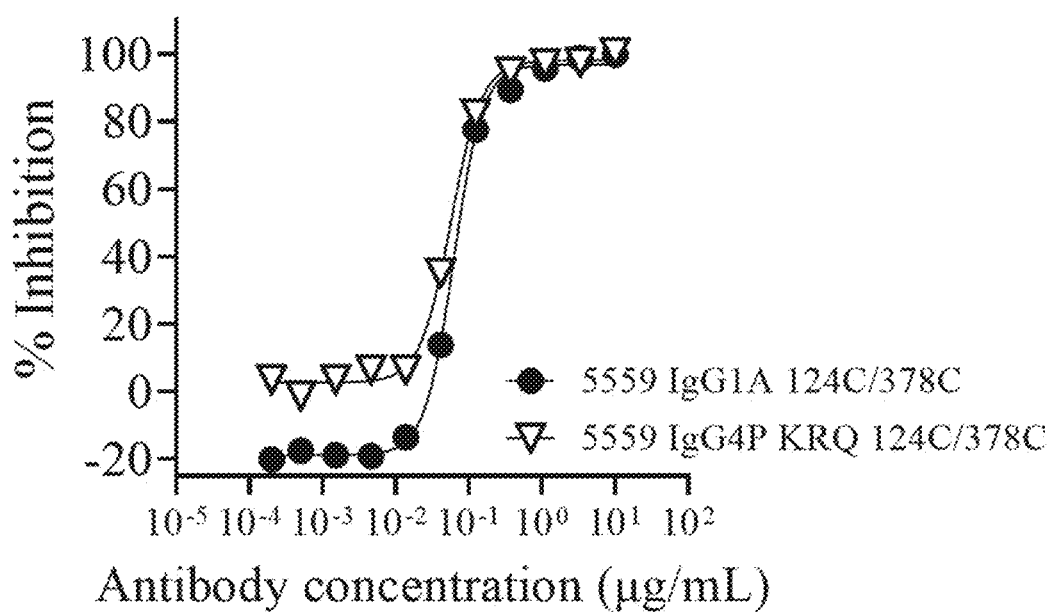
FIG. 6C shows the 5559 human IL-4Rα antibodies inhibit IL-13 induced pSTAT6 phosphorylation in human B cells.

Furthermore, the results as demonstrated in Table 8 and FIG. 6C, show that the exemplified IL-4Rα antibodies also inhibited IL-13 induced STAT6 phosphorylation in B cells (FIG. 6C) in a dose dependent manner. Specifically, the $IC_{50}$ values for inhibition of IL-13 induced pSTAT6 phosphorylation in B cells by the 5559 IgG1A 124C/378C and 5559 IgG4P KRQ 124C/378C antibodies was 0.06 μg/mL for both antibodies.

TABLE 7

Inhibition of IL-4 induced STAT6 phosphorylation in human T and B cells by exemplified human IL4Rα antibodies

| | Inhibition of STAT6 phosphorylation | |
|---|---|---|
| IL-4Rα Antibody | T cells $IC_{50}$ (μg/mL) | B cells $IC_{50}$ (μg/mL) |
| 5559 IgG1A 124C/378C | 0.07 | 0.05 |
| 5559 IgG4P KRQ 124C/378C | 0.07 | 0.05 |

TABLE 8

Inhibition of IL-13 induced STAT6 phosphorylation in human B cells by exemplified human IL4Rα antibodies

| IL-4Rα Antibody | Inhibition of STAT6 phosphorylation in B cells $IC_{50}$ (μg/mL) |
|---|---|
| 5559 IgG1A 124C/378C | 0.06 |
| 5559 IgG4P KRQ 124C/378C | 0.06 |

Inhibition of IL-4 induced B cell proliferation: Inhibition of B cell proliferation by the exemplified human IL-4Rα antibodies was assessed in primary B cells isolated from human PBMCs. Human PBMCs were isolated from human blood samples by standard Ficoll-Paque™ plus (GE HEALTHCARE) density gradient centrifugation methods, and primary B cells were isolated from the PBMC suspension by negative selection with EasySep™ Human Naïve B cell Enrichment kit according to the manufacturer's protocol (STEMCELL™ Technologies). Isolated human primary B cells were resuspended at 1×10⁶ cells/mL and plated in polystyrene 96-well, u-bottom plates in complete medium (RPMI-1640 containing 10% Fetal bovine serum, 1×MEM-nonessential amino acids, 1 mM sodium pyruvate, 1× penicillin-streptomycin solution (all from Corning®) and 1× GlutaMAX™ (Gibco™), 0.1% β-mercaptoethanol (LIFE TECHNOLOGIES). Cell were pretreated with anti-IL-4Rα antibodies or isotype control for 0.5-1 hour at 66.67 nM diluted 4-fold and 10-point titration. Cells were stimulated with Human CD40/TNFRSF5 Antibody (200 ng/mL; R&D SYSTEMS) and with IL-4 recombinant human protein (5 ng/mL; R&D SYSTEMS) for 2 days at 37° C. and 5% $CO_2$. Cells were then pulsed with [³H]-thymidine (1 μCi thymidine/well; PerkinElmer®) for 18 hours at 37° C. and level of [³H]-thymidine incorporation was measured by a Microplate Counter (MicroBeta²; PerkinElmer®) and expressed as a cell count per minute (CCPM). Statistical analysis was performed using GraphPad Prism 9 and curves were generated by fitting a sigmoidal curve of the log(Ab concentration) vs. CCPM.

Figure 7:
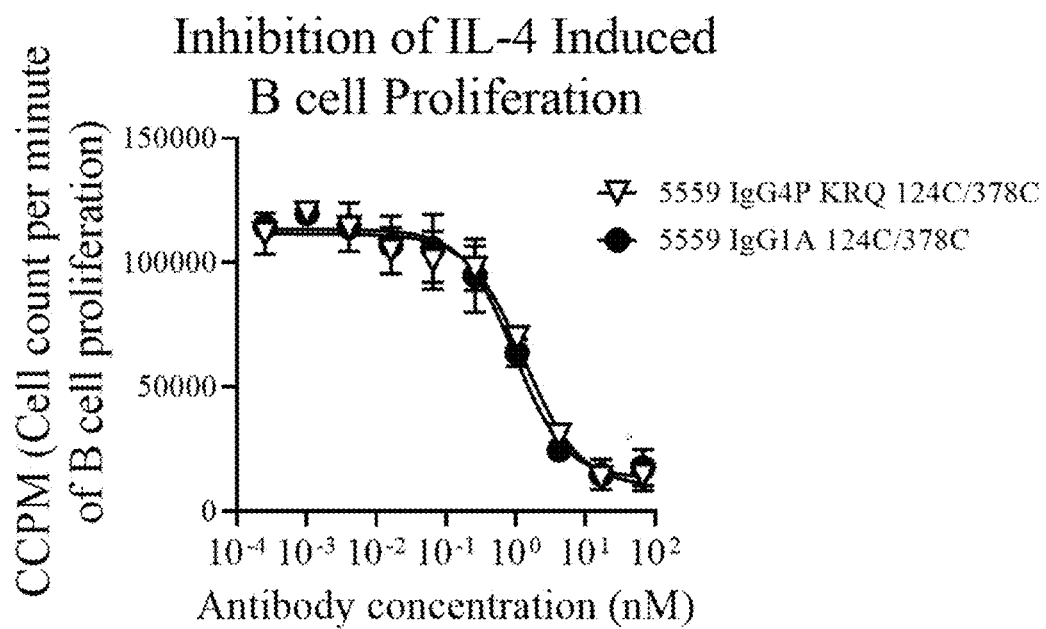
FIG. 7 shows the 5559 human IL-4Rα antibodies inhibit IL-4 induced B cell proliferation.

The results as demonstrated in Table 9 and FIG. 7, show that the exemplified IL-4Rα antibodies inhibited IL-4 induced B cell proliferation in a dose dependent manner. Specifically, the $IC_{50}$ for inhibition of IL-4 induced B cell proliferation by the 5559 IgG1A 124C/378C and 5559 IgG4P KRQ 124C/378C antibodies was 0.95 nM and 1.32 nM, respectively.

TABLE 9

Inhibition of IL-4 induced B cell proliferation by exemplified human IL4Rα antibodies

| IL-4Rα Antibody | Inhibition of B cell proliferation $IC_{50}$ (nM) |
|---|---|
| 5559 IgG1A 124C/378C | 0.95 |
| 5559 IgG4P KRQ 124C/378C | 1.32 |

Inhibition of IL-4 and IL-13 induced CD23 expression on Myeloid cells: Inhibition of IL-4 and IL-13 induced CD23 expression by the exemplified human IL4Rα antibodies was assessed in myeloid cells. Human PBMCs were isolated from human blood samples by standard Ficoll-Paque™ plus (GE HEALTHCARE) density gradient centrifugation methods. Cells were seeded at 2×10⁵ cells/well in a 96-well flat bottom plate. 50 μL of 3× serially diluted antibodies were added to the wells and incubated at 37° C. with 5% $CO_2$ for 30 minutes. Then 50 μL of 3× stimulation of either recombinant human IL-4 or IL-13 (R&D SYSTEMS) in complete media was added to the wells to a final concentration of 10 ng/mL. The plates were incubated 37° C. with 5% $CO_2$ for 48 hours, cells were washed and resuspended in FACS buffer containing Human TruStain FcX™ Brilliant Violet 785™ anti-human CD33 Antibody, FITC anti-human CD3 Antibody (from Biolegend®), CD20 Monoclonal Antibody (2H7) PerCP-Cyanine5.5, and CD23 Monoclonal Antibody (EBVCS2), APC (from THERMO FISHER SCIENTIFIC). Cells were incubated at 4° C. for 30 minutes, washed twice with FACS buffer and resuspended in a final volume of 100 μL FACS buffer. The viability dye, Sytox™ blue (THERMO FISHER SCIENTIFIC) was added to the wells and the samples were analyzed via a flow cytometer (LSR-Fortessa™ X-20; BD BIOSCIENCES). Data analysis was performed using FlowJo software. Myeloid cells were identified as Sytox™ blue, CD3, and CD20 negative, CD33 positive cells. Data was presented as sigmoidal curve fits of percent inhibition vs. the log(Ab concentration) of two donors and statistical analysis is performed using GraphPad Prism 9.

Figure 8A:
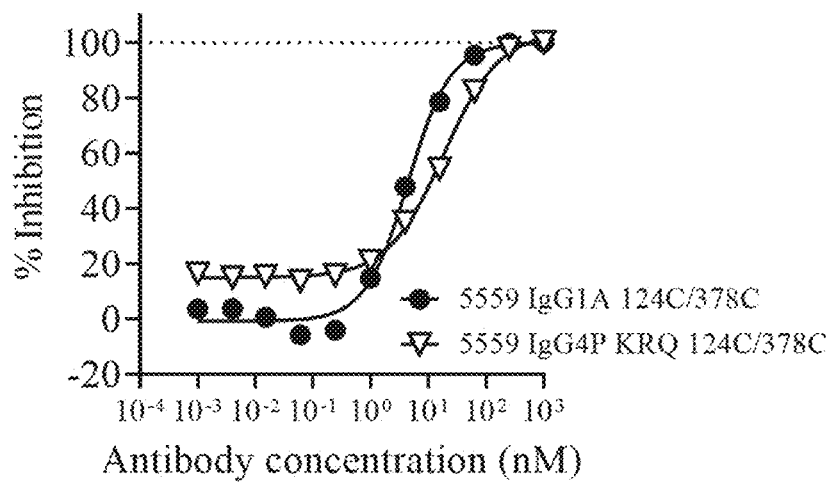
FIGS. 8A-8B show the 5559 human IL-4Rα antibodies inhibit IL-4 (8A) and IL-13 (8B) induced CD23 expression in myeloid cells.
Figure 8B:
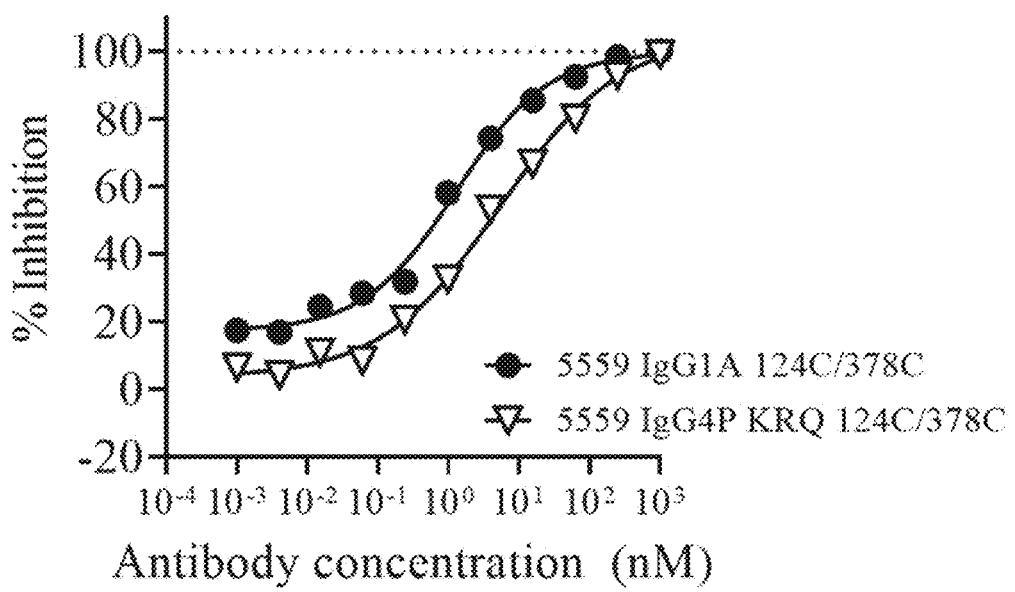

The results as demonstrated in Table 10, and FIGS. 8A and 8B, show that the exemplified IL-4Rα antibodies inhibited both IL-4 (FIG. 8A) and IL-13 (FIG. 8B) induced CD23 expression on myeloid cells. Specifically, the $IC_{50}$ values for inhibition of IL-4 induced CD23 expression by the 5559 IgG1A 124C/378C and 5559 IgG4P KRQ 124C/378C antibodies were 4.44 nM and 18.25 nM, respectively. Furthermore, the $IC_{50}$ values for inhibition of IL-13 induced CD23 expression by the 5559 IgG1A 124C/378C and 5559 IgG4P KRQ 124C/378C antibodies were 1.28 nM and 5.37 nM, respectively.

TABLE 10

Inhibition of IL-4 and IL-13 induced CD23 expression in myeloid cells by exemplified human IL-4Rα antibodies

| IL-4Rα Antibody | Inhibition of CD23 Expression | |
|---|---|---|
| | IL-4 induced $IC_{50}$ (nM) | IL-13 induced $IC_{50}$ (nM) |
| 5559 IgG1A 124C/378C | 4.44 | 1.28 |
| 5559 IgG4P KRQ 124C/378C | 18.25 | 5.37 |

Example 4. Effector Function Activity of the Human IL-4Rα Antibodies

Human Fcγ receptor binding. The binding affinity of the exemplified anti-IL-4Rα antibodies to human Fcγ receptors was evaluated by surface plasmon resonance (SPR) analysis. A series S CM5 chip (Cytiva P/N BR100530) was prepared using the manufacturer's EDC/NHS amine coupling method (Cytiva P/N BR100050). Briefly, the surfaces of all 4 flow cells (FC) were activated by injecting a 1:1 mixture of EDC/NHS for 7 minutes at 10 μL/minute. Protein A (Calbiochem P/N 539202) was diluted to 100 g/mL in 10 mM acetate, pH 4.5 buffer, and immobilized for approximately 4000 RU onto all 4 FCs by 7 minute injection at a flow rate of 10 μL/minute. Unreacted sites were blocked with a 7 minute injection of ethanolamine at 10 μL/minute. Injections of 2×10 L of glycine, pH 1.5, was used to remove any noncovalently associated protein. Running buffer was 1×HBS-EP+(TEKNOVA, P/N H8022). The FcγR extracellular domains (ECDs)—FcγRI (CD64), FcγRIIA_131R, and FcγRIIA_131H (CD32a), FcγRIIIA_158V, FcγRIIIA_158F (CD16a), and FcγRIIb (CD32b) were produced from stable CHO cell expression, and purified using IgG Sepharose and size exclusion chromatography. For FcγRI binding, antibodies were diluted to 2.5 μg/mL in running buffer, and approximately 150 RU of each antibody was captured in FCs 2 through 4 (RU captured). FC1 was the reference FC, therefore no antibody was captured in FC1. FcγRI ECD was diluted to 200 nM in running buffer and then two-fold serially diluted in running buffer to 0.78 nM. Duplicate injections of each concentration were injected over all FCs at 40 μL/minute for 120 seconds followed by a 1200 second dissociation phase. Regeneration was performed by injecting 15 μL of 10 mM glycine, pH 1.5, at 30 L/minute over all FCs. Reference-subtracted data was collected as FC2 FC1, FC3-FC1, and FC4-FC1 and the measurements were obtained at 25° C. The affinity (KD) was calculated using either steady state equilibrium analysis with the Scrubber 2 Biacore Evaluation Software or a "1:1 (Langmuir) binding" model in BIA Evaluation. For FcγRIIa, FcγRIIb, and FcγRIIIa binding, antibodies were diluted to 5 μg/mL in running buffer, and approximately 500 RU of each antibody was captured in FCs 2 through 4). FC1 was the reference FC. Fcγ receptor ECDs were diluted to 10 μM in running buffer and then serially diluted 2-fold in running buffer to 39 nM. Duplicate injections of each concentration were injected over all FCs at 40 μL/minute for 60 seconds followed by a 120 second dissociation phase. Regeneration was performed by injecting 15 μL of 10 mM glycine, pH 1.5, at 30 μL/minute over all FCs. Reference-subtracted data was collected as FC2-FC1, FC3-FC1, and FC4-FC1, and the measurements were obtained at 25° C. The affinity (KD) was calculated using the steady state equilibrium analysis with the Scrubber 2 Biacore Evaluation Software. Each receptor was assayed at least two times.

The results as demonstrated in Table 11, summarize the binding affinities ($K_D$) of the exemplified IL-4Rα antibodies 5559 IgG4P KRQ 124C/378C and 5559 IgG1 Å 124C/378C to human FcγRI, FcγRIIa, FcγRIIb, and FcγRIIIa receptor ECDs.

TABLE 11

Binding affinities of exemplified human IL-4Rα antibodies to human Fcγ receptors

| Fcγ Receptor | Hu IgG1 | | Hu IgG4 SP | | 5559 IgG4P KRQ 124C/378C | | 5559 IgG1A 124C/378C | |
|---|---|---|---|---|---|---|---|---|
| | Average $K_D$ | Std Dev | Average $K_D$ | Std Dev | Average $K_D$ | Std Dev | Average $K_D$ | Std Dev |
| FcγRI | 52.1 pM | 2.1 | 418.7 pM | 16.5 | 442.3 pM | 21.4 | 42.8 pM | 3.9 |
| FcγRIIA_131H | 0.68 μM | 0 | 5.31 μM | 0.03 | 3.75 μM | 0.11 | 1.24 μM | 0.01 |
| FcγRIIA_131R | 0.74 μM | 0 | 2.31 μM | 0.07 | 1.67 μM | 0.06 | 0.78 μM | 0.03 |
| FcγRIIb | 3.11 μM | 0.1 | 2.78 μM | 0.42 | 2.05 μM | 0.2 | 3.02 μM | 0.34 |
| FcγRIIIA_158V | 0.20 μM | 0.01 | 7.35 μM | 0.84 | 6.22 μM | 0.8 | 0.44 μM | 0.01 |
| FcγRIIIA_158F | 1.29 μM | 0.04 | >10 μM | | >10 μM | | 2.63 μM | 0.18 |

C1q binding. The binding of the exemplified anti-IL-4Rα antibodies to human C1q was evaluated by ELISA. 96-well microplates were coated with 100 μL/well of each exemplified antibody diluted in DPBS (Dulbecco's HyClone) from 10 μg/mL to 0.19 g/mL, and incubated overnight at 4° C. The coating reagent was removed, plates were blocked with 200 μL/well casein blocking buffer (Thermo) and incubated for 2 hours at room temperature (RT). Plates were washed 3 times with wash buffer (1×TBE with 0.05% Tween 20), and 10 μg/mL Human C1q (MS Biomedical) diluted in casein blocking reagent is added at 100 μL/well and incubated for 3 hours at RT. Humanized IgG1 and humanized IgG4P isotype control antibodies were used as positive and negative controls respectively. Plates were then washed three times with wash buffer and 100 L/well of a 1:800 times dilution of Sheep anti-human C1q-HRP (Abcam #ab46191) in casein blocker was added and incubated for 1 hour at RT. The plates were then washed 6 times with wash buffer, and 100 μL/well of TMB Substrate (Pierce) was added to each well and incubated for 7 minutes. 100 μL/well of 1 N HCl was added to stop the reaction. Optical density was immediately measured at 450 nm on a colorimetric microplate reader. Data was analyzed using SoftMax Pro 7.1 Data Acquisition and Analysis Software.

Figure 9:
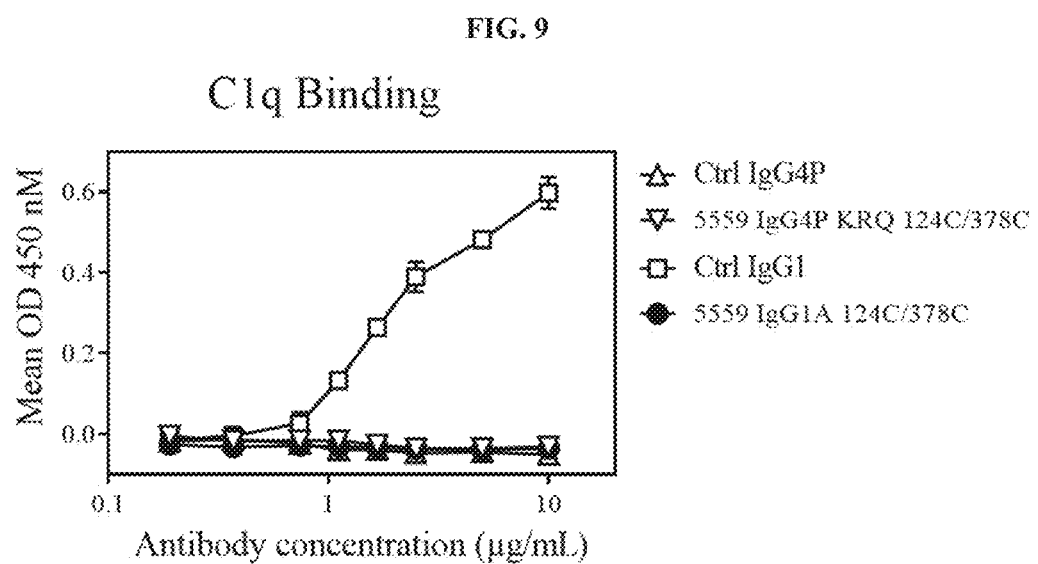
FIG. 9 shows the 5559 human IL-4Rα antibodies do not bind complement component C1q in an ELISA assay.

The results as demonstrated in FIG. 9, show that the exemplified antibodies 5559 IgG1A 124C/378C, and 5559 IgG4P KRQ 124C/378C did not bind complement component C1q.

Antibody dependent cellular cytotoxicity (ADCC): In vitro ADCC assays of the exemplified antibodies was evaluated with, either a reporter gene based ADCC assay or a primary human NK and Th2 cell based ADCC assay.

For the reporter gene based ADCC assay, Daudi cells (ATCC, #CCL-213) expressing human IL-4Rα and human CD20 as the target cell line and Jurkat cells expressing functional FcγRIIIa (V158)-NFAT-Luc (Eli Lilly and Company) as the effector cell line were used. All test antibodies and cells were diluted in assay medium containing RPMI-1640 (no phenol red) with 0.1 mM non-essential amino acids (NEAA), 1 mM sodium pyruvate, 2 mM L-glutamine, 500 U/mL of penicillin-streptomycin, and 0.1% w/v BSA. Test antibodies were first diluted to a 3× concentration of 3.3 μg/mL and then serially diluted 7 times in a 1:4 ratio. 50 μL/well of each antibody was aliquoted in duplicate in white opaque bottom 96-well plate (Costar, #3917). CD20 antibody was used as a positive control. Daudi target cells were then added to the plates at 5×10$^4$ cells/well in 50 μL aliquots, and incubated for 1 hour at 37° C. Next, Jurkat V158 cells were added to the wells at 150,000 cells/well in 50 μL aliquots and incubated for 4 hours at 37° C., followed by addition of 100 μL/well of One-Glo Luciferase substrate (Promega, #E8130). The contents of the plates were mixed using a plate shaker at low speed, incubated at room temperature for 5 minutes, and the luminescence signal was read on a BioTek microplate reader (BioTek Instruments) using 0.2 cps integration. Data was analyzed using GraphPad Prism 9 and the relative luminescence units (RLU) for each antibody concentration were plotted in a scatter format of antibody concentration versus RLU. Results were representative of two independent experiments.

For the primary human NK and Th2 cell based ADCC assay, primary human B cells and human Th2 cells cocultured with primary human NK cells were used. Human primary B cells, NK cells and naïve CD4 T cells were isolated from freshly purified human PBMCs by immunomagnetic negative selection, according to manufacturer's protocols (Human B cell Enrichment Kit, Stemcell Technologies #19054; Human NK Cell Isolation Kit, Stemcell Technologies #17955; Human Naïve CD4+ T cell Isolation Kit II, Stemcell Technologies #17555). Human Th2 cells were differentiated in vitro, by culturing purified naïve CD4 T cells with anti-human CD3 (BioXCell #BE0001-2), anti-human CD28 (BioLegend #302934), anti-human IFNγ (R&D Systems #MAB285-500), recombinant human IL-2 (R&D Systems #202-IL-050/CF), and recombinant human IL-4 (R&D Systems #6507-IL-100/CF), for 14 days. Flow cytometry staining was used to assess cell purity on a BD LSRFortessa Cell Analyzer. NK cells were confirmed CD56$^+$ (anti-human CD56-PE/Dazzle-594, BioLegend #318348) and FcγRIII$^+$ (anti-human CD16-SuperBright-702, Fisher Scientific #67-0168-42), B cells were confirmed as being CD19$^+$ (anti-human CD19-PE-Cy5, Fisher Scientific #15-0199-42) and IL-4Rα+(5559-Alexa Fluor-647, Lilly), and Th2 cells were confirmed as being CD4+(anti-human CD4-eFluor-450, Fisher Scientific #48-0047-42), GATA3+(anti-human GATA3-PerCP/Cyanine5.5, BioLegend #653812), and IL-4Rα+. 5×10$^4$ B cells or Th2 cells/well were treated with 30 μg/mL or 5 μg/mL 5559 IgG1 Å 124C/378C antibody, respectively, and co-cultured with 250,000 NK cells for 24 hrs, at 37° C. Positive control wells were treated with an anti-human CD52 antibody (Eli Lilly and Company). ADCC was measured using the CytoTox-Glo Cytotoxicity Assay (Promega #G9292), according to the manufacturer's protocol. Relative luminescence was detected using a Biotek Cytation 5 Imaging Multi-Mode Reader. The data is representative of three technical replicates per donor. Statistical analysis was performed using GraphPad Prism 9. Data represents the mean+SD of the relative luminescence units. Treatment differences were assessed using one-way ANOVA for each cell type individually and group comparisons against the No Ab group are evaluated using Tukey's test for multiple comparisons, with a significance level of 0.05.

Figure 10A:
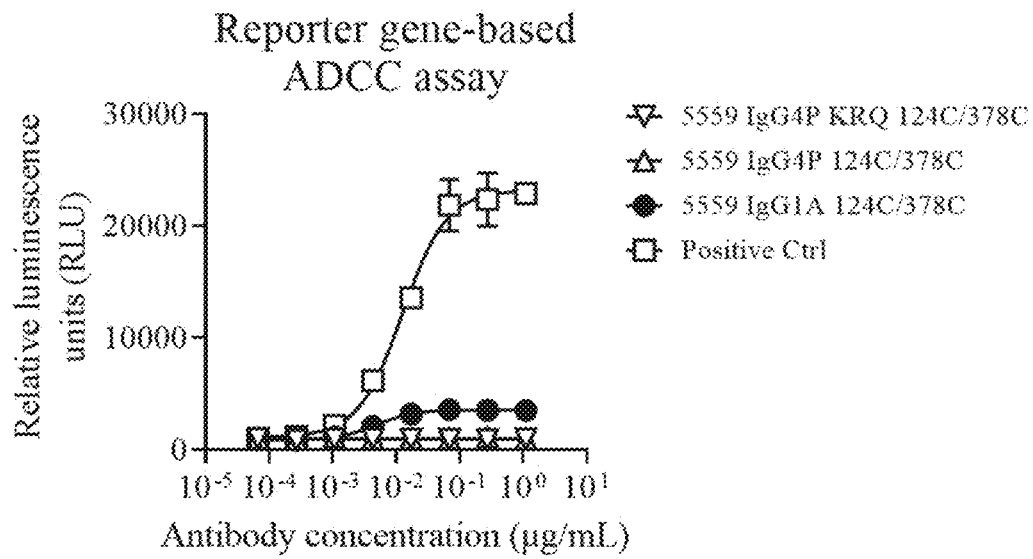
FIGS. 10A-10B show the 5559 human IL-4Rα antibodies do not significantly induce ADCC activity in either a reporter gene-based assay (10A) or a primary cell-based assay (10B).

The results of the reporter gene-based assay, as demonstrated in FIG. 10A, show that the exemplified IL-4Rα antibodies 5559 IgG1A 124C/378C, 5559 IgG4P KRQ 124C/378C and 5559 IgG4P 124C/378C significantly lacked or had no ADCC activity, when compared to the positive control.

Figure 10B:
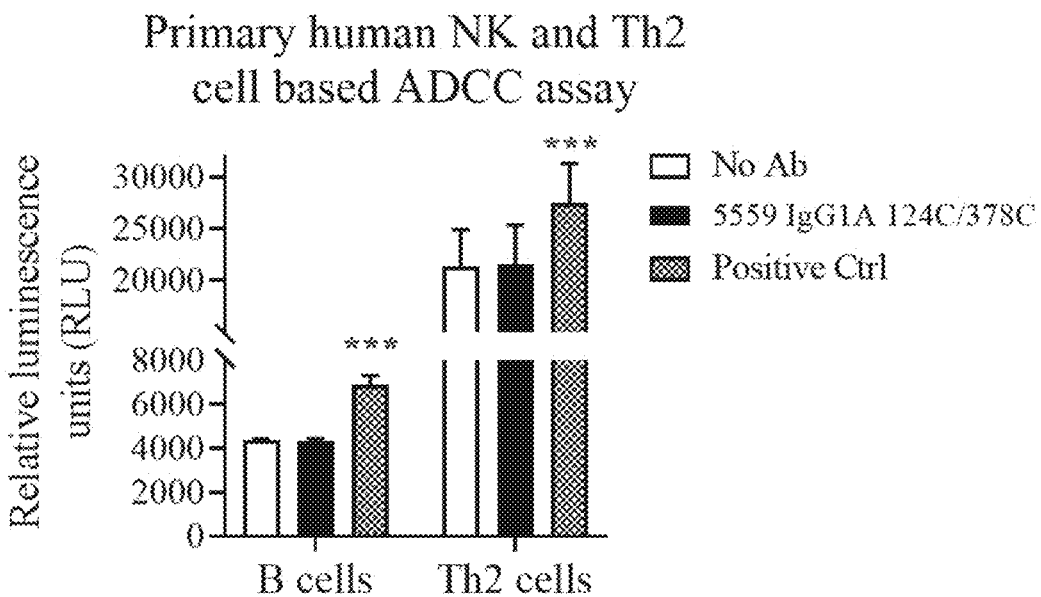

Furthermore, the results of the primary human NK and Th2 cell based ADCC assay, as demonstrated in FIG. 10B, show that the exemplified IL-4Rα antibody 5559 IgG1A 124C/378C did not induce ADCC activity in primary human B cells and human Th2 cells when compared to the positive control which demonstrated significant ADCC activity in both primary human B cells (p<0.0001) and Th2 cells (p=0.032) when compared to the negative control groups.

Complement dependent cellular cytotoxicity (CDC): In vitro CDC assays of the exemplified antibodies was conducted using Daudi cells (ATCC, #CCL-213). All test antibodies, complement, and cells were diluted in assay medium consisting of RPMI-1640 (no phenol red) with 0.1 mM non-essential amino acids (NEAA), 1 mM sodium pyruvate, 2 mM L-glutamine, 500 U/mL of penicillin-streptomycin, and 0.1% w/v BSA. Test antibodies were first diluted to a 3× concentration of 100 μg/mL and then serially diluted 7 times in a 1:4 ratio. 50 μL/well of each antibody (including the CD20 positive control antibody) was aliquoted in duplicate in white opaque bottom 96-well plate (Costar, #3917). Daudi target cells were added at 5×10$^4$ cells/well at 50 μL/well and incubated for 1 hour at 37° C. Next, human serum complement (Quidel, #A113) quickly thawed in a 37° C. water bath was diluted 1:6 in assay medium and added at 50 μL/well to the assay plate. The plate was incubated for 2 hours at 37° C., followed by addition of 100 L/well CellTiter Glo substrate (Promega, #G7571). The contents of the plates were mixed using a plate shaker at low speed, incubated at room temperature for 5 minutes, and the luminescence signal was read on a BioTek microplate reader (BioTek Instruments) using 0.2 cps integration. Data was analyzed using GraphPad Prism 9 and the relative luminescence units (RLU) for each antibody concentration were plotted in a scatter format of antibody concentration versus RLU. Results are representative of two independent experiments.

Figure 11:
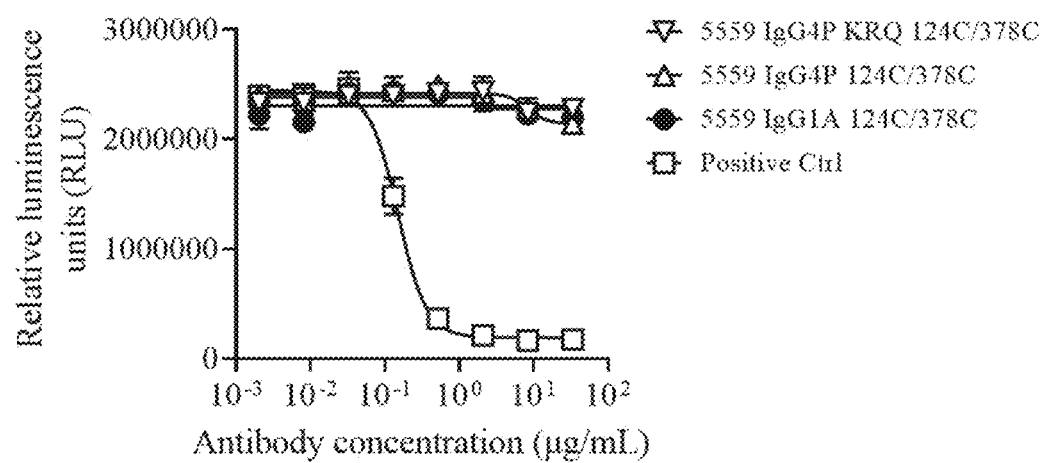
FIG. 11 shows the 5559 human IL-4Rα antibodies do not induce CDC activity in Daudi cells.

The results as demonstrated in FIG. 11, show that exemplified IL-4Rα antibodies 5559 IgG1A 124C/378C, 5559 IgG4P KRQ 124C/378C, and 5559 IgG4P 124C/378C did not induce CDC activity when compared to the positive control.

Example 5. Biophysical Properties of the Human IL-4Rα Antibodies

Biophysical properties of the exemplified human IL-4Rα antibodies 5559 IgG1A, 5559 IgG1A 124C/378C, 5559 IgG4P 124C/378C, and 5559 IgG4P KRQ 124C/378C were evaluated.

Aggregation from cell culture: Exemplified antibodies were transiently expressed in CHO cells. The antibody titers and percentage of high molecular weight (% HMW) species after Protein A affinity chromatography purification are listed in Table 12. The results as demonstrated in Table 12, show that incorporation of the engineered cysteines into the exemplified antibodies, or the introduction of the KRQ mutations into the exemplified 5559 IgG4P antibody did not significantly impact antibody titer or antibody aggregation.

Viscosity: Exemplified antibody samples were concentrated to about 125 mg/mL in a common formulation buffer matrix at pH 6 containing 5 mM histidine with excipients. The viscosity for each antibody was measured using VROC® initium (RheoSense) at 15° C. using the average of 9 replicate measurements. As demonstrated in Table 12, the results show that the 5559 IgG4P KRQ 124C/378C and 5559 IgG4P GNKRQ 124C/378C antibodies exhibited significantly improved viscosity of 11.6 cP and 9.6 cP respectively, when compared to the 5559 IgG4P 124C/378C which lacks the KRQ amino acid residue substitutions. The results further showed that the 5559 IgG4P KRQ 124C/378C and 5559 IgG4P GNKRQ 124C/378C antibodies had comparable viscosity to the 5559 IgG1 Å 124C/378C antibody. The low viscosity of the exemplified antibodies indicated a desirable developability property of the antibodies.

Figure 12A:
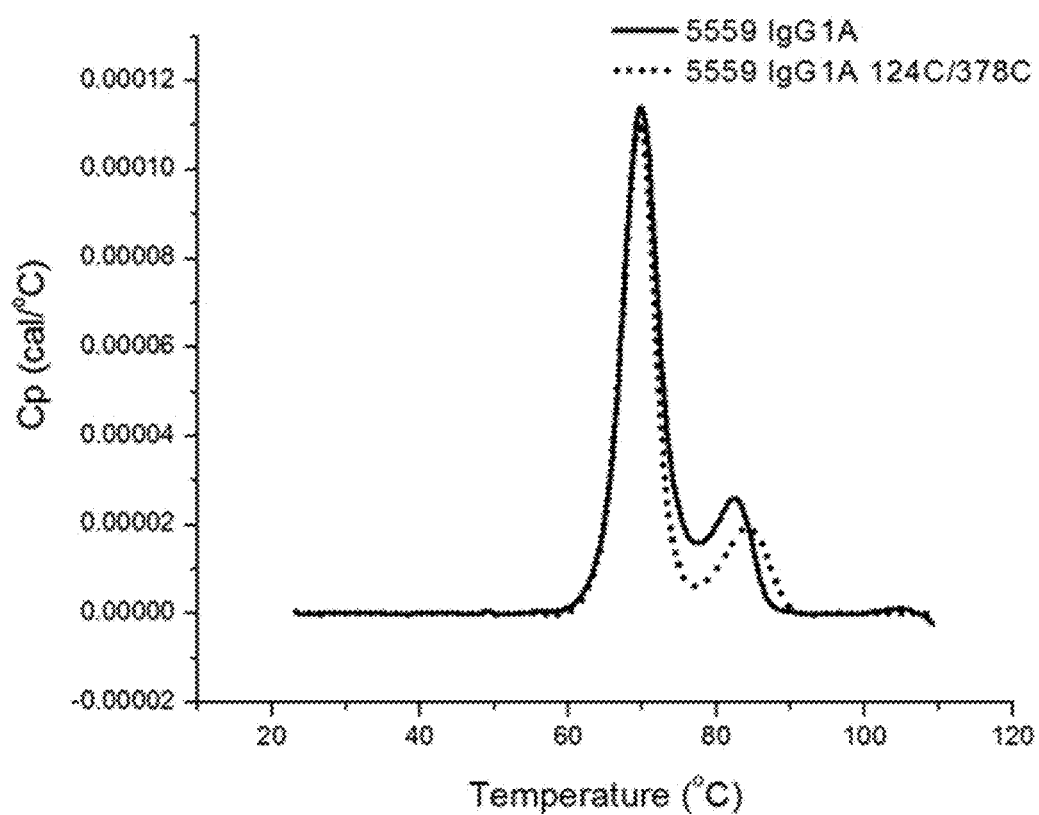
FIGS. 12A-12B show differential scanning calorimetry (DSC) thermograms of 5559 human IL-4Rα antibodies.
Figure 12B:
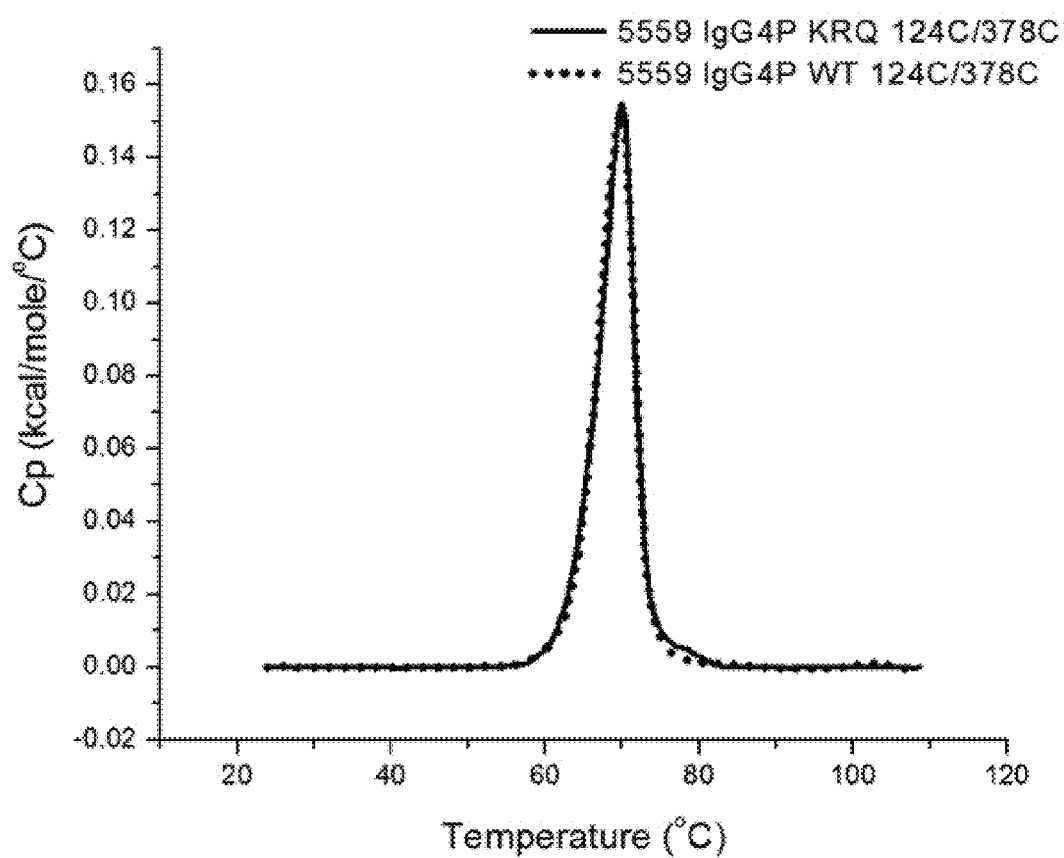
Figure 13:
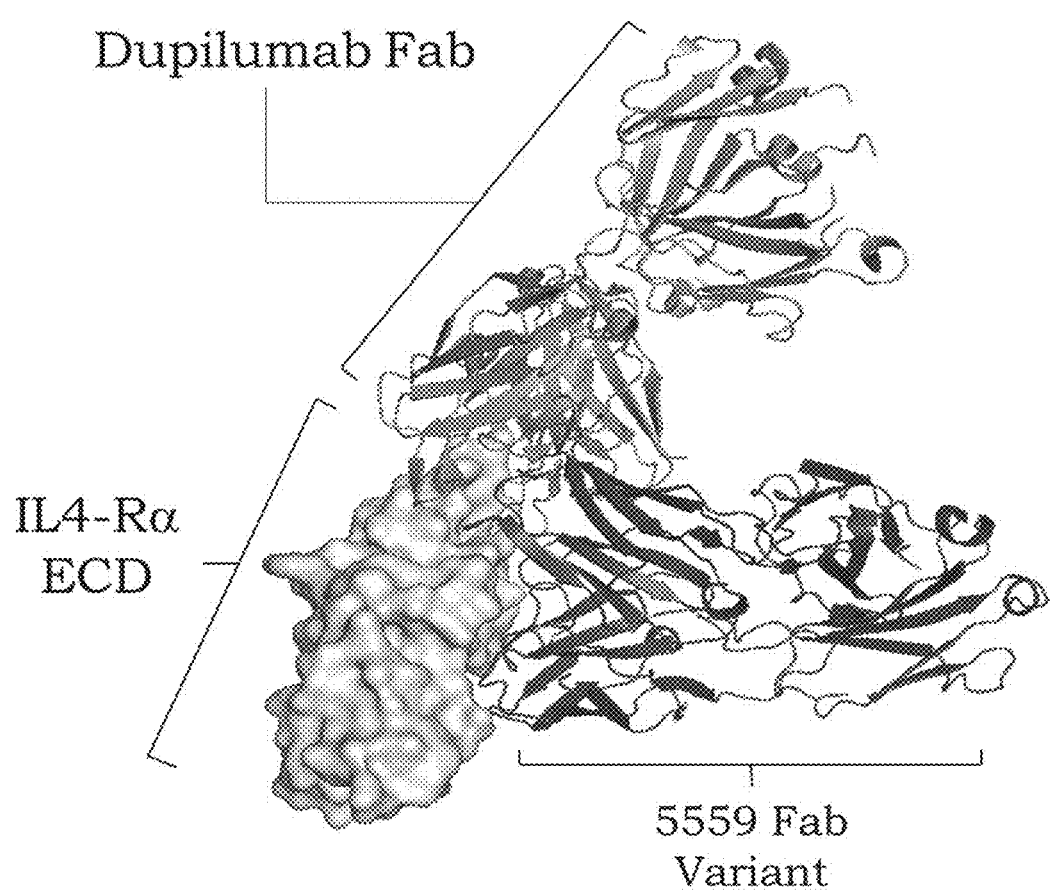
FIG. 13 shows X-ray crystal structure overlay of a Fab portion of the 5559 human IL-4Rα antibody bound to IL-4Rα ECD with the crystal structure of a dupilumab Fab portion with Crystal Kappa design complexed with human IL-4Rα (pdb accession code 6WGL).
Figure 14:
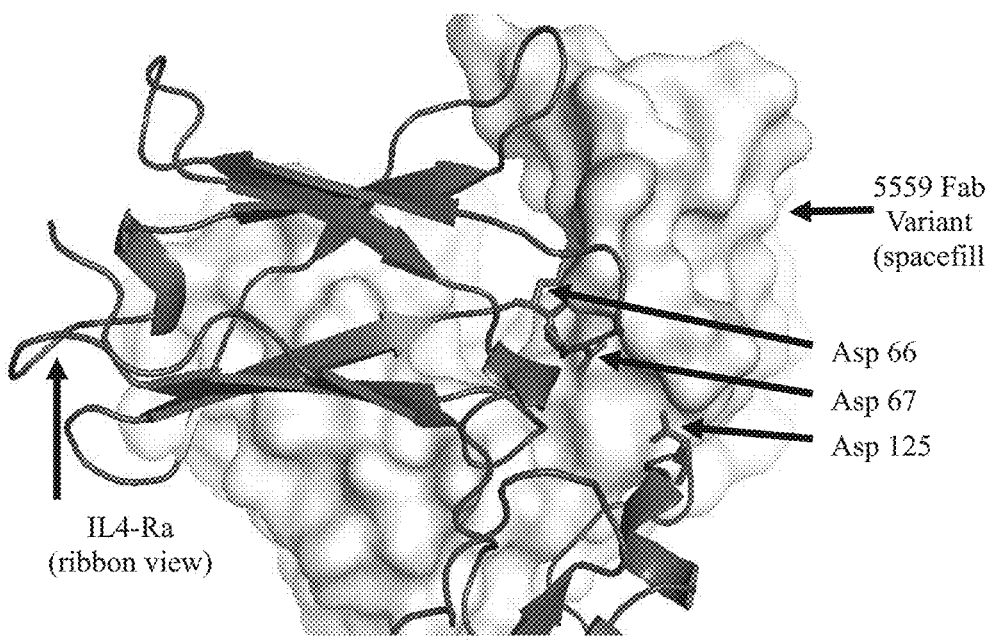
FIG. 14 shows the human IL-4Rα amino acid residue locations Asp66, Asp67 and Asp125 (all identified in the structural epitope; additionally Asp66 identified in functional epitope) in the crystal structure of 5559 Fab portion with Crystal Kappa design complexed with human IL-4Rα ECD.

Thermal stability: Differential Scanning Calorimetry (DSC) was used to evaluate the stability of the exemplified antibodies against thermal denaturation. The thermal melting temperatures of the antibodies in PBS, pH 7.2 buffer are listed in Table 12. Although the thermal transition temperatures for each domain were not well resolved in either the IgG1 or IgG4P constructs, the data as demonstrated in Table 12 and FIGS. 12A and 12B, show that the incorporation of the engineered cysteines into the exemplified antibodies, or the introduction of the KRQ mutations into the exemplified 5559 IgG4P antibody did not negatively impact the thermal stability of the antibodies or alter their structural integrity.

Aggregation upon temperature stress: The solution stability of the exemplified antibodies over time was assessed at approximately 100 mg/mL in a common 5 mM histidine pH 6.0 buffer with excipients. Concentrated samples were incubated for a period of 4 weeks at 5° C. and 35° C., respectively. Following incubation, samples were analyzed for the percentage of high molecular weight (% HMW) species with size exclusion chromatography (SEC). The exemplary results as demonstrated in Table 12, show that incorporation of the engineered cysteines into the exemplified antibodies, or the introduction of the KRQ mutations into the exemplified 5559 IgG4P antibody did not impact the aggregation profile of the antibodies over a 4-week time period at either 5° C. or 35° C.; specifically, the exemplary results show that the antibodies have comparable solution stability.

TABLE 12

Exemplary biophysical properties of exemplified human IL-4Rα antibodies

|  | 5559 IgG1A | 5559 IgG1A 124C/378C | 5559 IgG4P 124C/378C | 5559 IgG4P KRQ 124C/378C | 5559 IgG4P GNKRQ 124C/378C |
|---|---|---|---|---|---|
| tCHO titer (g/L) | 1.0 | 1.0 | 1.1 | 0.9 |  |
| % HMW post-protein A chromatography | 0.8 | 0.9 | 1.2 | 1 |  |
| Viscosity (cP) | 7.9 | 9.2 | 43 | 11.6 | 8.7 |
| $T_{onset}$ (° C.) | 60.8 | 61.3 | 59.0 | 59.1 |  |
| Tm1 (° C.) | 69.8 | 69.5 | 69.8 | 69.9 |  |
| Tm2 (° C.) | 81.7 | 83.4 | — | — |  |
| % HMW after 4-week incubation at 5° C. | 0.8 | 1.4 | 0.1 | 0.2 |  |
| % HMW after 4-week incubation at 35° C. | 1.7 | 3.0 | 2.4 | 2.2 |  |

SEQUENCE LISTING
5559 IgG1A 124C/378C
HCDR1 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
SEQ ID NO: 1
VASGFTFSHSSMN HCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
SEQ ID NO: 2
YISRATGAVY HCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 3
AREPVFDY LCDR1 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
SEQ ID NO: 4
RASQDISNYLA LCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 5
YAASSLQS LCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
SEQ ID NO: 6
LQWSSYPRT VH for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG1A 124C/378C
SEQ ID NO: 9
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDKTHTCP

PCPAPELLGGPSVFLFPPKPKDTLMISRTPEVTCVVVDVSHEDPE

VKFNWYVDGVEVHNAKTKPREEQYNSTYRVVSVLTVLHQDWLNGK

EYKCAVSNKALPAPIEKTISKAKGQPREPQVYTLPPSREEMTKNQ

VSLTCLVKGFYPSDICVEWESNGQPENNYKTTPPVLDSDGSFFLY

SKLTVDKSRWQQGNVFSCSVMHEALHNHYTQKSLSLSPGK

LC for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG1A 124C/378C
SEQ ID NO: 11
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCTAGCACCAAGGGC

CCATGCGTCTTCCCCCTGGCACCCTCCTCCAAGAGCACCTCTGGG

GGCACAGCGGCCCTGGGCTGCCTGGTCAAGGACTACTTCCCCGAA

CCGGTGACGGTGTCGTGGAACTCAGGCGCACTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACCCAGACC

TACATCTGCAACGTGAATCACAAGCCCAGCAACACCAAGGTGGAC

AAGAGAGTTGAGCCCAAATCTTGTGACAAAACTCACACATGCCCA

CCGTGCCCAGCACCTGAACTCCTGGGGGGACCGTCAGTCTTCCTC

TTCCCCCCAAAACCCAAGGACACCCTCATGATCTCCCGGACCCCT

-continued

```
GAGGTCACATGCGTGGTGGTGGACGTGAGCCACGAAGACCCTGAG

GTCAAGTTCAACTGGTATGTGGACGGCGTGGAGGTGCATAATGCC

AAGACAAAGCCGCGGGAGGAGCAGTACAACAGCACGTACCGTGTG

GTCAGCGTCCTCACCGTCCTGCACCAAGACTGGCTGAATGGCAAG

GAGTACAAGTGCGCCGTCTCCAACAAAGCCCTCCCAGCCCCCATC

GAGAAAACCATCTCCAAAGCCAAAGGGCAGCCCCGAGAACCACAG

GTGTACACCCTGCCCCCATCCCGGGAGGAGATGACCAAGAACCAA

GTCAGCCTGACCTGCCTGGTCAAAGGCTTCTATCCCAGCGACATC

TGCGTGGAGTGGGAGAGCAATGGGCAGCCGGAGAACAACTACAAG

ACCACGCCTCCCGTGCTGGACTCCGACGGCTCCTTCTTCCTCTAT

TCCAAGCTCACCGTGGACAAGAGCAGGTGGCAGCAGGGGAACGTC

TTCTCATGCTCCGTGATGCATGAGGCTCTGCACAACCACTACACG

CAGAAGAGCCTCTCCCTGTCTCCGGGCAAA

LC DNA for 5559 IgG1A, 5559 IgG1A
124C/378C, 5559 IgG4P,
5559 IgG4P 124C/378C, 5559 IgG4P
KRQ, 5559 IgG4P KRQ 124C/378C, 5559
IgG4P GNKRQ 124C/378C, and 5559
IgG1AAA 124C/378C
                                        SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC
5559 IgG4P KRQ 124C/378C

HCDR1 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
                                        SEQ ID NO: 1
VASGFTFSHSSMN HCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
                                        SEQ ID NO: 2
YISRATGAVY HCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
                                        SEQ ID NO: 3
AREPVFDY LCDR1 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
                                        SEQ ID NO: 4
RASQDISNYLA LCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
                                        SEQ ID NO: 5
YAASSLQS LCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
                                        SEQ ID NO: 6
LQWSSYPRT VH for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
                                        SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA
124C/378C
                                        SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG4P KRQ 124C/378C
                                        SEQ ID NO: 13
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVKF

NWYVDGVEVHNAKTKPREEQFNSTYRVVSVLTVLHQDWLNGKEYK
```

-continued

CKVSNKGLPSSIEKTISKAKGQPREPQVYTLPPSREEMTKNQVSL

TCLVKGFYPSDICVEWESNGQPENNYKTTPPVLDSDGSFFLYSRL

TVDKSRWQQGNVFSCSVMHEALHNHYTQKSLSLSLG

LC for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 10

DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG4P KRQ 124C/378C
SEQ ID NO: 14

CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATGCGTCTTCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCAAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCGAGAGGAGATGACCAAGAACCAGGTCAGCCTG

ACCTGCCTGGTCAAAGGCTTCTACCCCAGCGACATCGCCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGCAGGGGAATGTCTTCTCATGC

-continued

TCCGTGATGCATGAGGCTCTGCACAACCACTACACACAGAAGAGC

CTCTCCCTGTCTCTGGGT

LC DNA for 5559 IgG1A, 5559 IgG1A 124C/378C,
5559 IgG4P, 5559 IgG4P 124C/378C, 5559 IgG4P
KRQ, 5559 IgG4P KRQ 124C/378C, 5559
IgG4P GNKRQ 124C/378C, and 5559 IgG1AAA
124C/378C
SEQ ID NO: 12

GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

Human IL-4Rα extra-cellular domain
SEQ ID NO: 15

MKVLQEPTCVSDYMSISTCEWKMNGPTNCSTELRLLYQLVFLLSE

AHTCIPENNGGAGCVCHLLMDDVVSADNYTLDLWAGQQLLWKGSF

KPSEHVKPRAPGNLTVHTNVSDTLLLTWSNPYPPDNYLYNHLTYA

VNIWSENDPADFRIYNVTYLEPSLRIAASTLKSGISYRARVRAWA

QCYNTTWSEWSPSTKWHNSYREPFEQH

Cynomolgus monkey IL-4Rα
extra-cellular domain
SEQ ID NO: 16

MKVLQEPTCVSDYMSISTCEWKMGGPTNCSAELRLLYQLVFQSSE

THTCVPENNGGVGCVCHLLMDDVVSMDNYTLDLWAGQQLLWKGSF

KPSEHVKPRAPGNLTVHTNVSDTVLLTWSNPYPPDNYLYNDLTYA

VNIWSENDPAYSRIHNVTYLKPTLRIPASTLKSGISYRARVRAWA

QHYNTTWSEWSPSTKWYNSYREPFEQR

Human IL-4
SEQ ID NO: 17

MGLTSQLLPPLFFLLACAGNFVHGHKCDITLQEIIKTLNSLTEQK

TLCTELTVTDIFAASKNTTEKETFCRAATVLRQFYSHHEKDTRCL

GATAQQFHRHKQLIRFLKRLDRNLWGLAGLNSCPVKEANQSTLEN

FLERLKTIMREKYSKCSS

Human IL-13
SEQ ID NO: 18

MHPLLNPLLLALGLMALLLTTVIALTCLGGFASPGPVPPSTALRE

LIEELVNITQNQKAPLCNGSMVWSINLTAGMYCAALESLINVSGC

SAIEKTQRMLSGFCPHKVSAGQFSSLHVRDTKIEVAQFVKDLLLH

LKKLFREGRFN

5F3IeG4PAA
HCDR1 (North) for 5F3 IgG4PAA
SEQ ID NO: 19
AASGFTFSISSMN

HCDR2 (North) for 5F3 IgG4PAA
SEQ ID NO: 20
YISRATGAIY

HCDR3 (North) for 5559 IgG1A,
5559 IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, 5559 IgG1AAA
124C/378C, and 5F3 IgG4PAA
SEQ ID NO: 3
AREPVFDY LCDR1 (North) for 5F3 IgG4PAA and
8660 IgG4P 124C/378C
SEQ ID NO: 22
RASQGISNYLA LCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 5
YAASSLQS LCDR3 (North) for 5F3 IgG4PAA
SEQ ID NO: 24
LQHNSYPRT VH for 5F3 IgG4PAA
SEQ ID NO: 25
QVQLVESGGGLVQPGGSLRLSCAASGFTFSISSMNWVRQAPGKGL

EWVSYISRATGAIYYADSVKGRFTISRNNAKNSLYLQMNSLRDED

TAVYYCAREPVFDYWGQGTLVTVSS

VL for 5F3 IgG4PAA
SEQ ID NO: 26
DIQMTQSPSAMSASVGDRVTITCRASQGISNYLAWFQQKPGKVPT

RLIYAASSLQSGVPSRFSGSGSGTEFTLTISSLQPEDFATYYCLQ

HNSYPRTFGQGTKVEIK

HC for 5F3 IgG4PAA
SEQ ID NO: 27
QVQLVESGGGLVQPGGSLRLSCAASGFTFSISSMNWVRQAPGKGL

EWVSYISRATGAIYYADSVKGRFTISRNNAKNSLYLQMNSLRDED

TAVYYCAREPVFDYWGQGTLVTVSSASTKGPSVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEAAGGPSVFLFPPKPKDTLMISRTPEVTCVVVDVSQEDPEVQF

NWYVDGVEVHNAKTKPREEQFNSTYRVVSVLTVLHQDWLNGKEYK

CKVSNKGLPSSIEKTISKAKGQPREPQVYTLPPSQEEMTKNQVSL

TCLVKGFYPSDIAVEWESNGQPENNYKTTPPVLDSDGSFFLYSRL

TVDKSRWQEGNVFSCSVMHEALHNHYTQKSLSLSLG

LC for 5F3 IgG4PAA
SEQ ID NO: 28
DIQMTQSPSAMSASVGDRVTITCRASQGISNYLAWFQQKPGKVPT

RLIYAASSLQSGVPSRFSGSGSGTEFTLTISSLQPEDFATYYCLQ

HNSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5F3 IgG4PAA
SEQ ID NO: 29
CAGGTACAGCTGGTGGAGTCTGGGGGAGGCTTGGTACAGCCTGGG

GGGTCCCTGAGACTCTCCTGTGCAGCCTCTGGATTCACCTTCAGT

ATCTCTAGCATGAACTGGGTCCGCCAGGCTCCAGGGAAGGGGCTG

GAGTGGGTTTCATACATTAGTCGTGCTACTGGTGCCATATACTAC

GCAGACTCTGTAAAGGGCCGATTCACCATCTCCAGAAACAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCTTCTACCAAGGGC

CCATCGGTCTTCCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGGCCGCCGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCCAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCAGGAGGAGATGACCAAGAACCAGGTCAGCCTG

ACCTGCCTGGTCAAAGGCTTCTACCCCAGCGACATCGCCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGGAGGGGAATGTCTTCTCATGC

TCCGTGATGCATGAGGCTCTGCACAACCACTACACACAGAAGAGC

CTCTCCCTGTCTCTGGGT

LC DNA for 5F3 IgG4PAA
SEQ ID NO: 30
GACATCCAGATGACCCAGTCTCCATCTGCCATGTCTGCATCTGTG

GGAGACAGAGTCACCATCACTTGTCGGGCGAGTCAGGGCATTAGC

-continued

```
AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

CATAATAGTTACCCTCGGACGTTCGGCCAAGGGACCAAGGTGGAA

ATCAAACGAACTGTGGCGGCGCCATCTGTCTTCATCTTCCCGCCA

TCTGATGAGCAGTTGAAATCCGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC
```

5559 IgG4P 124C/378C
HCDR1 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C
SEQ ID NO: 1
VASGFTFSHSSMN HCDR2 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, and 5559 IgG1AAA 124C/378C
SEQ ID NO: 2
YISRATGAVY HCDR3 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, 5559 IgG1AAA 124C/378C, and 5F3 IgG4PAA
SEQ ID NO: 3
AREPVFDY LCDR1 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C
SEQ ID NO: 4
RASQDISNYLA LCDR2 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, 5559 IgG1AAA 124C/378C, and 5F3 IgG4PAA
SEQ ID NO: 5
YAASSLQS LCDR3 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, and 5559 IgG1AAA 124C/378C
SEQ ID NO: 6
LQWSSYPRT VH for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C
SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C
SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG4P 124C/378C
SEQ ID NO: 31
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVQF

NWYVDGVEVHNAKTKPREEQFNSTYRVVSVLTVLHQDWLNGKEYK

CKVSNKGLPSSIEKTISKAKGQPREPQVYTLPPSQEEMTKNQVSL

TCLVKGFYPSDICVEWESNGQPENNYKTTPPVLDSDGSFFLYSRL

TVDKSRWQEGNVFSCSVMHEALHNHYTQKSLSLSLG

LC for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C
SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG4P 124C/378C
SEQ ID NO: 32
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

-continued

```
GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATGCGTCTTCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCCAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCAGGAGGAGATGACCAAGAACCAGGTCAGCCTG

ACCTGCCTGGTCAAAGGCTTCTACCCCAGCGACATCTGCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGGAGGGGAATGTCTTCTCATGC

TCCGTGATGCATGAGGCTCTGCACAACCACTACACACAGAAGAGC

CTCTCCCTGTCTCTGGGT

LC DNA for 5559 IgG1A, 5559
IgG1A 124C/378C, 5559 IgG4P,
5559 IgG4P 124C/378C, 5559 IgG4P KRQ,
5559 IgG4P KRQ 124C/378C, 5559
IgG4P GNKRQ 124C/378C, and 5559
IgG1AAA 124C/378C
                                        SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC
```

5559 IgG1A
HCDR1 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
                                        SEQ ID NO: 1
VASGFTFSHSSMN HCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
                                        SEQ ID NO: 2
YISRATGAVY HCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
                                        SEQ ID NO: 3
AREPVFDY LCDR1 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
                                        SEQ ID NO: 4
RASQDISNYLA LCDR2 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
                                        SEQ ID NO: 5
YAASSLQS LCDR3 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
                                        SEQ ID NO: 6
LQWSSYPRT VH for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
                                        SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG1A
SEQ ID NO: 33
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPSVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDKTHTCP

PCPAPELLGGPSVFLFPPKPKDTLMISRTPEVTCVVVDVSHEDPE

VKFNWYVDGVEVHNAKTKPREEQYNSTYRVVSVLTVLHQDWLNGK

EYKCAVSNKALPAPIEKTISKAKGQPREPQVYTLPPSREEMTKNQ

VSLTCLVKGFYPSDIAVEWESNGQPENNYKTTPPVLDSDGSFFLY

SKLTVDKSRWQQGNVFSCSVMHEALHNHYTQKSLSLSPGK

LC for 5559 IgG1A, 5559 IgG1A 124C/378C,
5559 IgG4P, 5559
IgG4P 124C/378C, 5559 IgG4P KRQ, 5559
IgG4P KRQ 124C/378C, 5559 IgG4P
GNKRQ 124C/378C, and 5559 IgG1AAA 124C/378C
SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG1A
SEQ ID NO: 34
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCTAGCACCAAGGGC

CCATCGGTCTTCCCCCTGGCACCCTCCTCCAAGAGCACCTCTGGG

GGCACAGCGGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACCCAGACC

TACATCTGCAACGTGAATCACAAGCCCAGCAACACCAAGGTGGAC

AAGAGAGTTGAGCCCAAATCTTGTGACAAAACTCACACATGCCCA

CCGTGCCCAGCACCTGAACTCCTGGGGGGACCGTCAGTCTTCCTC

TTCCCCCCAAAACCCAAGGACACCCTCATGATCTCCCGGACCCCT

GAGGTCACATGCGTGGTGGTGGACGTGAGCCACGAAGACCCTGAG

GTCAAGTTCAACTGGTATGTGGACGGCGTGGAGGTGCATAATGCC

AAGACAAAGCCGCGGGAGGAGCAGTACAACAGCACGTACCGTGTG

GTCAGCGTCCTCACCGTCCTGCACCAAGACTGGCTGAATGGCAAG

GAGTACAAGTGCGCCGTCTCCAACAAAGCCCTCCCAGCCCCCATC

GAGAAAACCATCTCCAAAGCCAAAGGGCAGCCCCGAGAACCACAG

GTGTACACCCTGCCCCCATCCCGGGAGGAGATGACCAAGAACCAA

GTCAGCCTGACCTGCCTGGTCAAAGGCTTCTATCCCAGCGACATC

GCCGTGGAGTGGGAGAGCAATGGGCAGCCGGAGAACAACTACAAG

ACCACGCCTCCCGTGCTGGACTCCGACGGCTCCTTCTTCCTCTAT

TCCAAGCTCACCGTGGACAAGAGCAGGTGGCAGCAGGGGAACGTC

TTCTCATGCTCCGTGATGCATGAGGCTCTGCACAACCACTACACG

CAGAAGAGCCTCTCCCTGTCTCCGGGCAAA

LC DNA for 5559 IgG1A, 5559 IgG1A
124C/378C, 5559 IgG4P,
5559 IgG4P 124C/378C, 5559 IgG4P
KRQ, 5559 IgG4P KRQ 124C/378C, 5559 IgG4P
GNKRQ 124C/378C, and 5559 IgG1AAA 124C/378C
SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

5559 IgG4P KRQ
HCDR1 (North) for 5559 IgG1A,
5559 IgG1A 124C/378C, 5559
IgG4P, 5559 IgG4P 124C/378C, 5559 IgG4P KRQ,
5559 IgG4P KRQ 124C/378C,
5559 IgG4P GNKRQ 124C/378C, and
5559 IgG1AAA 124C/378C -continued

VASGFTFSHSSMN

HCDR2 (North) for 5559 IgG1A,
5559 IgG1A 124C/378C, 5559
IgG4P, 5559 IgG4P 124C/378C, 5559 IgG4P KRQ,
5559 IgG4P KRQ 124C/378C,
8660 IgG4P 124C/378C, 5559 IgG4P GNKRQ
124C/378C, and 5559 IgG1AAA
124C/378C

SEQ ID NO: 2

YISRATGAVY

HCDR3 (North) for 5559 IgG1A, 5559
IgG1A 124C/378C, 5559
IgG4P, 5559 IgG4P 124C/378C, 5559 IgG4P KRQ,
5559 IgG4P KRQ 124C/378C,
8660 IgG4P 124C/378C, 5559 IgG4P GNKRQ
124C/378C, 5559 IgG1AAA
124C/378C, and 5F3 IgG4PAA

SEQ ID NO: 3

AREPVFDY

LCDR1 (North) for 5559 IgG1A,
5559 IgG1A 124C/378C, 5559
IgG4P, 5559 IgG4P 124C/378C, 5559 IgG4P KRQ,
5559 IgG4P KRQ 124C/378C,
5559 IgG4P GNKRQ 124C/378C, and
5559 IgG1AAA 124C/378C

SEQ ID NO: 4

RASQDISNYLA

LCDR2 (North) for 5559 IgG1A,
5559 IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, 5559 IgG1AAA
124C/378C, and 5F3 IgG4PAA

SEQ ID NO: 5

YAASSLQS

LCDR3 (North) for 5559 IgG1A,
5559 IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, and 5559 IgG1AAA
124C/378C

SEQ ID NO: 6

LQWSSYPRT

VH for 5559 IgG1A, 5559 IgG1A
124C/378C, 5559 IgG4P, 5559
IgG4P 124C/378C, 5559 IgG4P KRQ, 5559 IgG4P
KRQ 124C/378C, 5559 IgG4P
GNKRQ 124C/378C, and 5559 IgG1AAA 124C/378C

SEQ ID NO: 7

QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A
124C/378C, 5559 IgG4P, 5559
IgG4P 124C/378C, 5559 IgG4P KRQ, 5559 IgG4P
KRQ 124C/378C, 5559 IgG4P
GNKRQ 124C/378C, and 5559 IgG1AAA 124C/378C

SEQ ID NO: 8

DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG4P KRQ

SEQ ID NO: 35

QVQLVESGGGLVQPGGSLRLSCVASGFTFSHSSMNWVRQAPGKGL

EWVSYISRATGAVYYADSVKGRFTISRDNAKNSLYLQMNSLRDED

-continued

SEQ ID NO: 1

TAVYYCAREPVFDYWGQGTLVTVSSASTKGPSVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVKF

NWYVDGVEVHNAKTKPREEQFNSTYRVVSVLTVLHQDWLNGKEYK

CKVSNKGLPSSIEKTISKAKGQPREPQVYTLPPSREEMTKNQVSL

TCLVKGFYPSDIAVEWESNGQPENNYKTTPPVLDSDGSFFLYSRL

TVDKSRWQQGNVFSCSVMHEALHNHYTQKSLSLSLG

LC for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C

SEQ ID NO: 10

DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG4P KRQ

SEQ ID NO: 36

CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATCGGTCTTCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCAAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

```
CTGCCCCCATCCCGAGAGGAGATGACCAAGAACCAGGTCAGCCTG

ACCTGCCTGGTCAAAGGCTTCTACCCCAGCGACATCGCCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGCAGGGGAATGTCTTCTCATGC

TCCGTGATGCATGAGGCTCTGCACAACCACTACACACAGAAGAGC

CTCTCCCTGTCTCTGGGT

LC DNA for 5559 IgG1A, 5559
IgG1A 124C/378C, 5559 IgG4P,
5559 IgG4P 124C/378C, 5559 IgG4P
KRQ, 5559 IgG4P KRQ 124C/378C, 5559 IgG4P
GNKRQ 124C/378C, and 5559 IgG1AAA 124C/378C
                                        SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

5559 IgG4P
HCDR1 (North) for 5559 IgG1A, 5559
IgG1A 124C/378C, 5559
IgG4P, 5559 IgG4P 124C/378C, 5559 IgG4P
KRQ, 5559 IgG4P KRQ 124C/378C,
5559 IgG4P GNKRQ 124C/378C, and 5559
IgG1AAA 124C/378C
                                         SEQ ID NO: 1
VASGFTFSHSSMN HCDR2 (North) for 5559 IgG1A, 5559
IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, and 5559 IgG1AAA
124C/378C
                                         SEQ ID NO: 2
YISRATGAVY HCDR3 (North) for 5559 IgG1A, 5559
IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG1AAA
124C/378C, and 5F3 IgG4PAA
                                         SEQ ID NO: 3
AREPVFDY LCDR1 (North) for 5559 IgG1A, 5559 IgG1A
124C/378C, 5559
IgG4P, 5559 IgG4P 124C/378C, 5559 IgG4P
KRQ, 5559 IgG4P KRQ 124C/378C,
5559 IgG4P GNKRQ 124C/378C, and 5559
IgG1AAA 124C/378C
                                         SEQ ID NO: 4
RASQDISNYLA LCDR2 (North) for 5559 IgG1A, 5559 IgG1A
124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, 5559 IgG1AAA
124C/378C, and 5F3 IgG4PAA
                                         SEQ ID NO: 5
YAASSLQS LCDR3 (North) for 5559 IgG1A,
5559 IgG1A 124C/378C, 5559
IgG4P, 5559 IgG4P 124C/378C, 5559 IgG4P
KRQ, 5559 IgG4P KRQ 124C/378C,
8660 IgG4P 124C/378C, 5559 IgG4P GNKRQ
124C/378C, and 5559 IgG1AAA
124C/378C
                                         SEQ ID NO: 6
LQWSSYPRT VH for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
                                         SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
                                         SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG4P
                                         SEQ ID NO: 37
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPSVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVQF

NWYVDGVEVHNAKTKPREEQFNSTYRVVSVLTVLHQDWLNGKEYK

CKVSNKGLPSSIEKTISKAKGQPREPQVYTLPPSQEEMTKNQVSL

TCLVKGFYPSDIAVEWESNGQPENNYKTTPPVLDSDGSFFLYSRL

TVDKSRWQEGNVFSCSVMHEALHNHYTQKSLSLSLG
```

LC for 5559 IgG1A, 5559 IgG1A
124C/378C, 5559 IgG4P, 5559
IgG4P 124C/378C, 5559 IgG4P KRQ,
5559 IgG4P KRQ 124C/378C, 5559 IgG4P
GNKRQ 124C/378C, and 5559 IgG1AAA 124C/378C
SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG4P
SEQ ID NO: 38
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATCGGTCTTCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCCAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCAGGAGGAGATGACCAAGAACCAGGTCAGCCTG

ACCTGCCTGGTCAAAGGCTTCTACCCCAGCGACATCGCCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGGAGGGGAATGTCTTCTCATGC

TCCGTGATGCATGAGGCTCTGCACAACCACTACACACAGAAGAGC

CTCTCCCTGTCTCTGGGT

LC DNA for 5559 IgG1A, 5559 IgG1A
124C/378C, 5559 IgG4P,
5559 IgG4P 124C/378C, 5559 IgG4P KRQ,
5559 IgG4P KRQ 124C/378C, 5559
IgG4P GNKRQ 124C/378C, and 5559
IgG1AAA 124C/378C
SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

Human IL-4Rα
SEQ ID NO: 39
MGWLCSGLLFPVSCLVLLQVASSGNMKVLQEPTCVSDYMSISTCEWKM

NGPTNCSTELRLLYQLVFLLSEAHTCIPENNGGAGCVCHLLMDDV

VSADNYTLDLWAGQQLLWKGSFKPSEHVKPRAPGNLTVHTNVSDT

LLLTWSNPYPPDNYLYNHLTYAVNIWSENDPADFRIYNVTYLEPS

LRIAASTLKSGISYRARVRAWAQCYNTTWSEWSPSTKWHNSYREP

FEQHLLLGVSVSCIVILAVCLLCYVSITKIKKEWWDQIPNPARSR

LVAIIIQDAQGSQWEKRSRGQEPAKCPHWKNCLTKLLPCFLEHNM

KRDEDPHKAAKEMPFQGSGKSAWCPVEISKTVLWPESISVVRCVE

LFEAPVECEEEEEVEEEKGSFCASPESSRDDFQEGREGIVARLTE

SLFLDLLGEENGGFCQQDMGESCLLPPSGSTSAHMPWDEFPSAGP

KEAPPWGKEQPLHLEPSPPASPTQSPDNLTCTETPLVIAGNPAYR

SFSNSLSQSPCPRELGPDPLLARHLEEVEPEMPCVPQLSEPTTVP

QPEPETWEQILRRNVLQHGAAAAPVSAPTSGYQEFVHAVEQGGTQ

ASAVVGLGPPGEAGYKAFSSLLASSAVSPEKCGFGASSGEEGYKP

FQDLIPGCPGDPAPVPVPLFTFGLDREPPRSPQSSHLPSSSPEHL

GLEPGEKVEDMPKPPLPQEQATDPLVDSLGSGIVYSALTCHLCGH

LKQCHGQEDGGQTPVMASPCCGCCCGDRSSPPTTPLRAPDPSPGG

VPLEASLCPASLAPSGISEKSKSSSSFHPAPGNAQSSSQTPKIVN

FVSVGPTYMRVS

Cynomolgus monkey IL-4Rα
SEQ ID NO: 40
MGWLCSGLLFPVSCLVLLQVASSGCSCVSPGSMKVLQEPTCVSDY

MSISTCEWKMGGPTNCSAELRLLYQLVFQSSETHTCVPENNGGVG

CVCHLLMDDVVSMDNYTLDLWAGQQLLWKGSFKPSEHVKPRAPGN

LTVHTNVSDTVLLTWSNPYPPDNYLYNDLTYAVNIWSENDPAYSR

IHNVTYLKPTLRIPASTLKSGISYRARVRAWAQHYNTTWSEWSPS

TKWYNSYREPFEQRLLWGVSAACVFILFFCLSCYFSVTKIKKEWW

DQIPNPARSHLVAIIQDAQESQWEKRSRGQEAAKCPYWKNCLTK

LLPCFLEHNMKRDEDPHKAVKDLPFRGSGKSAWCPVEISKTVLWP

ESISVVRCVELFEAPVECKEEEEVEEEKGSFCTSSESNRDDFQEG

REGIVARLTESLFLDLLGGENGGFFQQDMGESCLLPPLGSTSAHV

PWDEFPSAGSKEVPPWGKEQPLHQEPSPPASPTQSPDNPTCTEMP

LVISSNPAYRSFSNSLSQSPCPRELGPDPLLARHLEEVDPEMPCA

PQLSEPTTVAPAEPETWEQILRRNVLQHGAAAAPASAPTSGYREF

VHAVQQGGIQASAVAGLGPPGEAGYKAFSSLLASSAVSPGECGFG

ASSGEEGYKPFQDLTPGCPGDPAPVPVPLFTFGLDREPPHSPQSS

HLPSNSPEHLALEPGEKVEDMQKPPLPPEQATDPLGDSLGSGIVY

SALTCHLCGHLKQCHGQEDGGQAPVVASPCCGCCCGDRSSPPTTP

LRAPDPSLGGVPLEASLCPASLAPSGISEKSKSSLSFHPAPGSAQ

SSSQTPQIVNFVSVGPTCMRVS

Human CD23
SEQ ID NO: 41
MEEGQYSEIEELPRRRCCRRGTQIVLLGLVTAALWAGLLTLLLLW

HWDTTQSLKQLEERAARNVSQVSKNLESHHGDQMAQKSQSTQISQ

ELEELRAEQQRLKSQDLELSWNLNGLQADLSSFKSQELNERNEAS

DLLERLREEVTKLRMELQVSSGFVCNTCPEKWINFQRKCYYFGKG

TKQWVHARYACDDMEGQLVSIHSPEEQDFLTKHASHTGSWIGLRN

LDLKGEFIWVDGSHVDYSNWAPGEPTSRSQGEDCVMMRGSGRWND

AFCDRKLGAWVCDRLATCTPPASEGSAESMGPDSRPDPDGRLPTP

SAPLHS

8660 IgG4P 124C/378C

HCDR1 (North) for 8660 IgG4P 124C/378C
SEQ ID NO: 42
AASGFTFSHSSMN

HCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
SEQ ID NO: 2
YISRATGAVY HCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 3
AREPVFDY LCDR1 (North) for 5F3 IgG4PAA and
8660 IgG4P 124C/378C
SEQ ID NO: 22
RASQGISNYLA LCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 5
YAASSLQS LCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
SEQ ID NO: 6
LQWSSYPRT VH for 8660 IgG4P 124C/378C
SEQ ID NO: 44
QVQLVESGGGLVQPGGSLRLSCAASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 8660 IgG4P 124C/378C
SEQ ID NO: 45
DIQMTQSPSAMSASVGDRVTITCRASQGISNYLAWFQQKPGKVPT

RLIYAASSLQSGVPSRFSGSGSGTEFTLTISSLQPEDFATYYCLQ

WSSYPRTFGQGTKVEIK

HC for 8660 IgG4P 124C/378C
SEQ ID NO: 46
QVQLVESGGGLVQPGGSLRLSCAASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPCSRSTSE

STAALGCLVKDYFPEPVTVSWNSGALTSGVHTFPAVLQSSGLYSL

SSVVTVPSSSLGTKTYTCNVDHKPSNTKVDKRVESKYGPPCPPCP

APEFLGGPSVFLFPPKPKDTLMISRTPEVTCVVVDVSQEDPEVQF

NWYVDGVEVHNAKTKPREEQFNSTYRVVSVLTVLHQDWLNGKEYK

CKVSNKGLPSSIEKTISKAKGQPREPQVYTLPPSQEEMTKNQVSL

TCLVKGFYPSDICVEWESNGQPENNYKTTPPVLDSDGSFFLYSRL

TVDKSRWQEGNVFSCSVMHEALHNHYTQKSLSLSLG

LC for 8660 IgG4P 124C/378C
SEQ ID NO: 47
DIQMTQSPSAMSASVGDRVTITCRASQGISNYLAWFQQKPGKVPT

RLIYAASSLQSGVPSRFSGSGSGTEFTLTISSLQPEDFATYYCLQ

-continued

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 8660 IgG4P 124C/378C
SEQ ID NO: 48
CAGGTACAGCTGGTGGAGTCTGGGGGAGGCTTGGTACAGCCTGGG

GGGTCCCTGAGACTCTCCTGTGCAGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATGCGTCTTCCCGCTAGCGCCCTGCTCCAGGAGCACCTCCGAG

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAGATCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCCAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCAGGAGGAGATGACCAAGAACCAGGTCAGCCTG

ACCTGCCTGGTCAAAGGCTTCTACCCCAGCGACATCGCCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGGAGGGGAATGTCTTCTCATGC

TCCGTGATGCATGAGGCTCTGCACAACCACTACACACAGAAGAGC

CTCTCCCTGTCTCTGGGT

LC DNA for 8660 IgG4P 124C/378C
SEQ ID NO: 49
GACATCCAGATGACCCAGTCTCCATCTGCCATGTCTGCATCTGTG

GGAGACAGAGTCACCATCACTTGTCGGGCGAGTCAGGGCATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

5559 IgG4P GNKRO 124C/378C

HCDR1 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and 5559
IgG1AAA 124C/378C
SEQ ID NO: 1
VASGFTFSHSSMN HCDR2 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, and 5559 IgG1AAA
124C/378C
SEQ ID NO: 2
YISRATGAVY HCDR3 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P
GNKRQ 124C/378C, 5559 IgG1AAA
124C/378C, and 5F3 IgG4PAA
SEQ ID NO: 3
AREPVFDY LCDR1 (North) for 5559 IgG1A,
5559 IgG1A 124C/378C, 5559
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C
SEQ ID NO: 4
RASQDISNYLA LCDR2 (North) for 5559 IgG1A, 5559 IgG1A
124C/378C, 5559 IgG4P, 5559 IgG4P 124C/378C,
5559 IgG4P KRQ, 5559 IgG4P KRQ 124C/378C,
8660 IgG4P 124C/378C, 5559 IgG4P GNKRQ
124C/378C, 5559 IgG1AAA
124C/378C, and 5F3 IgG4PAA
SEQ ID NO: 5
YAASSLQS LCDR3 (North) for 5559 IgG1A, 5559
IgG1A 124C/378C, 5559
IgG4P, 5559 IgG4P 124C/378C, 5559
IgG4P KRQ, 5559 IgG4P KRQ 124C/378C,
8660 IgG4P 124C/378C, 5559 IgG4P GNKRQ
124C/378C, and 5559 IgG1AAA
124C/378C
SEQ ID NO: 6
LQWSSYPRT VH for 5559 IgG1A, 5559 IgG1A 124C/378C,
5559 IgG4P, 5559
IgG4P 124C/378C, 5559 IgG4P KRQ, 5559

IgG4P KRQ 124C/378C, 5559 IgG4P
GNKRQ 124C/378C, and 5559 IgG1AAA 124C/378C
SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A 124C/378C,
5559 IgG4P, 5559 IgG4P 124C/378C, 5559
IgG4P KRQ, 5559 IgG4P KRQ 124C/378C, 5559 IgG4P
GNKRQ 124C/378C, and 5559 IgG1AAA 124C/378C
SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG4P GNKRQ 124C/378C
SEQ ID NO: 50
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPCSRSTSG

STAALGCLVKDYFPEPVTVSWNSGALTSGVHTFPAVLQSSGLYSL

SSVVTVPSSSLGTKTYTCNVNHKPSNTKVDKRVESKYGPPCPPCP

APEFLGGPSVFLFPPKPKDTLMISRTPEVTCVVVDVSQEDPEVKF

NWYVDGVEVHNAKTKPREEQFNSTYRVVSVLTVLHQDWLNGKEYK

CKVSNKGLPSSIEKTISKAKGQPREPQVYTLPPSREEMTKNQVSL

TCLVKGFYPSDICVEWESNGQPENNYKTTPPVLDSDGSFFLYSRL

TVDKSRWQQGNVFSCSVMHEALHNHYTQKSLSLSLG

LC for 5559 IgG1A, 5559 IgG1A 124C/378C,
5559 IgG4P, 5559 IgG4P 124C/378C, 5559 IgG4P
KRQ, 5559 IgG4P KRQ 124C/378C, 5559 IgG4P
GNKRQ 124C/378C, and 5559 IgG1AAA 124C/378C
SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG4P GNKRQ 124C/378C
SEQ ID NO: 51
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCCTCCACCAAGGGC

CCATGCGTCTTCCCGCTAGCGCCCTGCTCCAGGAGCACCTCCGGC

AGCACAGCCGCCCTGGGCTGCCTGGTCAAGGACTACTTCCCCGAA

CCGGTGACGGTGTCGTGGAACTCAGGCGCCCTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACGAAGACC

TACACCTGCAACGTAAACCACAAGCCCAGCAACACCAAGGTGGAC

AAGAGAGTTGAGTCCAAATATGGTCCCCCATGCCCACCCTGCCCA

GCACCTGAGTTCCTGGGGGGACCATCAGTCTTCCTGTTCCCCCCA

AAACCCAAGGACACTCTCATGATCTCCCGGACCCCTGAGGTCACG

TGCGTGGTGGTGGACGTGAGCCAGGAAGACCCCGAGGTCAAGTTC

AACTGGTACGTGGATGGCGTGGAGGTGCATAATGCCAAGACAAAG

CCGCGGGAGGAGCAGTTCAACAGCACGTACCGTGTGGTCAGCGTC

CTCACCGTCCTGCACCAGGACTGGCTGAACGGCAAGGAGTACAAG

TGCAAGGTCTCCAACAAAGGCCTCCCGTCCTCCATCGAGAAAACC

ATCTCCAAAGCCAAAGGGCAGCCCCGAGAGCCACAGGTGTACACC

CTGCCCCCATCCCGAGAGGAGATGACCAAGAACCAGGTCAGCCTG

ACCTGCCTGGTCAAAGGCTTCTACCCCAGCGACATCTGCGTGGAG

TGGGAAAGCAATGGGCAGCCGGAGAACAACTACAAGACCACGCCT

CCCGTGCTGGACTCCGACGGCTCCTTCTTCCTCTACAGCAGGCTA

ACCGTGGACAAGAGCAGGTGGCAGCAGGGGAATGTCTTCTCATGC

TCCGTGATGCATGAGGCTCTGCACAACCACTACACACAGAAGAGC

CTCTCCCTGTCTCTGGGT

LC DNA for 5559 IgG1A, 5559 IgG1A 124C/378C,
5559 IgG4P, 5559 IgG4P 124C/378C, 5559 IgG4P
KRQ, 5559 IgG4P KRQ 124C/378C, 5559
IgG4P GNKRQ 124C/378C, and 5559 IgG1AAA 124C/378C
SEQ ID NO: 12
GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

5559 IgG1AAA 124C/378C
HCDR1 (North) for 5559 IgG1A
5559 IgG1A 124C/378C, 5559,
IgG4P, 5559 IgG4P 124C/378C, 5559
IgG4P KRQ, 5559 IgG4P KRQ 124C/378C,
5559 IgG4P GNKRQ 124C/378C, and
5559 IgG1AAA 124C/378C -continued HCDR1 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, and 5559 IgG1AAA 124C/378C

SEQ ID NO: 1
VASGFTFSHSSMN

HCDR2 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, and 5559 IgG1AAA 124C/378C

SEQ ID NO: 2
YISRATGAVY

HCDR3 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, 5559 IgG1AAA 124C/378C, and 5F3 IgG4PAA

SEQ ID NO: 3
AREPVFDY

LCDR1 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C

SEQ ID NO: 4
RASQDISNYLA

LCDR2 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, 5559 IgG1AAA 124C/378C, and 5F3 IgG4PAA

SEQ ID NO: 5
YAASSLQS

LCDR3 (North) for 5559 IgG1A, 5559 IgG1A 124C/378C, 5559 IgG4P, 5559 IgG4P 124C/378C, 5559 IgG4P KRQ, 5559 IgG4P KRQ 124C/378C, 8660 IgG4P 124C/378C, 5559 IgG4P GNKRQ 124C/378C, and 5559 IgG1AAA 124C/378C

SEQ ID NO: 6
LQWSSYPRT

VH for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C

SEQ ID NO: 7
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSS

VL for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C

SEQ ID NO: 8
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIK

HC for 5559 IgG1AAA 124C/378C

SEQ ID NO: 52
QVQLVESGGGLVQPGGSLRLSCVASGFTFSHSSMNWVRQAPGKGL

EWVSYISRATGAVYYADSVKGRFTISRDNAKNSLYLQMNSLRDED

TAVYYCAREPVFDYWGQGTLVTVSSASTKGPCVFPLAPSSKSTSG

GTAALGCLVKDYFPEPVTVSWNSGALTSGVHTFPAVLQSSGLYSL

SSVVTVPSSSLGTQTYICNVNHKPSNTKVDKRVEPKSCDKTHTCP

PCPAPEAAGGPSVFLFPPKPKDTLMISRTPEVTCVVVDVSHEDPE

VKFNWYVDGVEVHNAKTKPREEQYNSTYRVVSVLTVLHQDWLNGK

EYKCKVSNKALAAPIEKTISKAKGQPREPQVYTLPPSREEMTKNQ

VSLTCLVKGFYPSDICVEWESNGQPENNYKTTPPVLDSDGSFFLY

SKLTVDKSRWQQGNVFSCSVMHEALHNHYTQKSLSLSPGK

LC for 5559 IgG1A, 5559 IgG1A 124C/378C, 5559 IgG4P, 5559 IgG4P 124C/378C, 5559 IgG4P KRQ, 5559 IgG4P KRQ 124C/378C, 5559 IgG4P GNKRQ 124C/378C, and 5559 IgG1AAA 124C/378C

SEQ ID NO: 10
DIQMTQSPSAMSASVGDRVTITCRASQDISNYLAWFQQKPGKVPT

RLIYAASSLQSGVPSRFSGSGSGTEFTLTISSLQPEDFATYYCLQ

WSSYPRTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

HC DNA for 5559 IgG1AAA 124C/378C

SEQ ID NO: 53
CAGGTACAGCTGGTGGAGTCTGGGGGAGGCTTGGTACAGCCTGGG

GGGTCCCTGAGACTCTCCTGTGTCGCCTCTGGATTCACCTTCAGT

CATTCTAGCATGAACTGGGTCCGCCAGGCTCCAGGGAAGGGGCTG

GAGTGGGTTTCATACATTAGTCGTGCTACTGGTGCCGTCTACTAC

GCAGACTCTGTAAAGGGCCGATTCACCATCTCCAGAGATAATGCC

AAAAACTCACTGTATCTGCAAATGAACAGCCTGAGAGACGAGGAC

ACGGCTGTGTATTACTGTGCGAGAGAGCCGGTTTTTGACTACTGG

GGCCAGGGAACCCTGGTCACCGTCTCCTCAGCTAGCACCAAGGGC

CCATGCGTCTTCCCCCTGGCACCCTCCTCCAAGAGCACCTCTGGG

GGCACAGCGGCCCTGGGCTGCCTGGTCAAGGACTACTTCCCCGAA

CCGGTGACGGTGTCGTGGAACTCAGGCGCACTGACCAGCGGCGTG

CACACCTTCCCGGCTGTCCTACAGTCCTCAGGACTCTACTCCCTC

AGCAGCGTGGTGACCGTGCCCTCCAGCAGCTTGGGCACCCAGACC

TACATCTGCAACGTGAATCACAAGCCCAGCAACACCAAGGTGGAC

AAGAGAGTTGAGCCCAAATCTTGTGACAAAACTCACACATGCCCA

CCGTGCCCAGCACCTGAAGCCGCCGGGGGACCGTCAGTCTTCCTC

TTCCCCCCAAAACCCAAGGACACCCTCATGATCTCCCGGACCCCT

GAGGTCACATGCGTGGTGGTGGACGTGAGCCACGAAGACCCTGAG

GTCAAGTTCAACTGGTATGTGGACGGCGTGGAGGTGCATAATGCC

AAGACAAAGCCGCGGGAGGAGCAGTACAACAGCACGTACCGTGTG

GTCAGCGTCCTCACCGTCCTGCACCAAGACTGGCTGAATGGCAAG

-continued

GAGTACAAGTGCAAGGTCTCCAACAAAGCCCTCGCCGCCCCCATC

GAGAAAACCATCTCCAAAGCCAAAGGGCAGCCCCGAGAACCACAG

GTGTACACCCTGCCCCCATCCCGGGAGGAGATGACCAAGAACCAA

GTCAGCCTGACCTGCCTGGTCAAAGGCTTCTATCCCAGCGACATC

TGCGTGGAGTGGGAGAGCAATGGGCAGCCGGAGAACAACTACAAG

ACCACGCCTCCCGTGCTGGACTCCGACGGCTCCTTCTTCCTCTAT

TCCAAGCTCACCGTGGACAAGAGCAGGTGGCAGCAGGGGAACGTC

TTCTCATGCTCCGTGATGCATGAGGCTCTGCACAACCACTACACG

CAGAAGAGCCTCTCCCTGTCTCCGGGCAAA

LC DNA for 5559 IgG1A, 5559
IgG1A 124C/378C, 5559 IgG4P,
5559 IgG4P 124C/378C, 5559 IgG4P
KRQ, 5559 IgG4P KRQ 124C/378C, 5559
IgG4P GNKRQ 124C/378C, and 5559
IgG1AAA 124C/378C

SEQ ID NO: 12

GACATCCAGATGACCCAGTCTCCATCTGCCATGTCTGCATCTGTG

GGAGACAGAGTCACCATCACTTGTCGGGCGAGTCAGGACATTAGC

AATTATTTAGCCTGGTTTCAGCAGAAACCAGGGAAAGTCCCTACG

CGCCTGATCTATGCTGCATCCAGTTTGCAAAGTGGGGTCCCATCA

AGGTTCAGCGGCAGTGGATCTGGGACAGAATTCACTCTCACAATC

AGCAGCCTGCAGCCTGAAGATTTTGCAACTTATTACTGTCTACAG

TGGTCCAGTTACCCTCGGACGTTCGGCCAAGGGACCAAGGTGGAA

ATCAAACGGACCGTGGCTGCACCATCTGTCTTCATCTTCCCGCCA

TCTGATGAGCAGTTGAAATCTGGAACTGCCTCTGTTGTGTGCCTG

CTGAATAACTTCTATCCCAGAGAGGCCAAAGTACAGTGGAAGGTG

GATAACGCCCTCCAATCGGGTAACTCCCAGGAGAGTGTCACAGAG

CAGGACAGCAAGGACAGCACCTACAGCCTCAGCAGCACCCTGACG

CTGAGCAAAGCAGACTACGAGAAACACAAAGTCTACGCCTGCGAA

GTCACCCATCAGGGCCTGAGCTCGCCCGTCACAAAGAGCTTCAAC

AGGGGAGAGTGC

---

The invention claimed is:

1. An antibody or antigen binding fragment thereof that specifically binds human IL-4Rα, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:
the HCDR1 comprises SEQ ID NO: 1;
the HCDR2 comprises SEQ ID NO: 2;
the HCDR3 comprises SEQ ID NO: 3;
the LCDR1 comprises SEQ ID NO: 4;
the LCDR2 comprises SEQ ID NO: 5; and
the LCDR3 comprises SEQ ID NO: 6.

2. The antibody or antigen binding fragment thereof of claim 1, wherein the VH comprises SEQ ID NO: 7 and the VL comprises SEQ ID NO: 8.

3. An antibody or antigen binding fragment thereof that specifically binds human IL-4Rα, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:
the HCDR1 comprises SEQ ID NO: 42;
the HCDR2 comprises SEQ ID NO: 2;
the HCDR3 comprises SEQ ID NO: 3;
the LCDR1 comprises SEQ ID NO: 22;
the LCDR2 comprises SEQ ID NO: 5; and
the LCDR3 comprises SEQ ID NO: 6.

4. The antibody or antigen binding fragment thereof of claim 3, wherein the VH comprises SEQ ID NO: 44 and the VL comprises SEQ ID NO: 45.

5. The antibody or antigen binding fragment thereof of claim 1, wherein the antibody comprises:
i. a heavy chain (HC) comprising SEQ ID NO: 33 and a light chain (LC) comprising SEQ ID NO: 10;
ii. a heavy chain (HC) comprising SEQ ID NO: 35 and a light chain (LC) comprising SEQ ID NO: 10;
iii. a heavy chain (HC) comprising SEQ ID NO: 9 and a light chain (LC) comprising SEQ ID NO: 10;
iv. a heavy chain (HC) comprising SEQ ID NO: 13 and a light chain (LC) comprising SEQ ID NO: 10;
v. a heavy chain (HC) comprising SEQ ID NO: 31 and a light chain (LC) comprising SEQ ID NO: 10;
vi. a heavy chain (HC) comprising SEQ ID NO: 37 and a light chain (LC) comprising SEQ ID NO: 10;
vii. a heavy chain (HC) comprising SEQ ID NO: 52 and a light chain (LC) comprising SEQ ID NO: 10; or
viii. a heavy chain (HC) comprising SEQ ID NO: 50 and a light chain (LC) comprising SEQ ID NO: 10.

6. The antibody or antigen binding fragment thereof of claim 3, wherein the antibody comprises a HC comprising SEQ ID NO: 46 and a LC comprising SEQ ID NO: 47.

7. The antibody or antigen binding fragment thereof of claim 1, wherein the antibody comprises a human IgG1 isotype.

8. The antibody or antigen binding fragment thereof of claim 3, wherein the antibody comprises a human IgG1 isotype.

9. The antibody or antigen binding fragment thereof of claim 7, wherein the antibody comprises an alanine at amino acid residue 322 (EU numbering).

10. The antibody or antigen binding fragment thereof of claim 8, wherein the antibody comprises an alanine at amino acid residue 322 (EU numbering).

11. The antibody or antigen binding fragment thereof of claim 1, wherein the antibody comprises a human IgG4 isotype.

12. The antibody or antigen binding fragment thereof of claim 3, wherein the antibody comprises a human IgG4 isotype.

13. The antibody or antigen binding fragment thereof of claim 11, wherein the antibody comprises one or more of the following: a glycine at amino acid residue 137 (EU numbering); an asparagine at amino acid residue 203 (EU numbering); a lysine at amino acid residue 274 (EU numbering); an arginine at amino acid residue 355 (EU numbering); or a glutamine at amino acid residue 419 (EU numbering).

14. The antibody or antigen binding fragment thereof of claim 12, wherein the antibody comprises one or more of the following: a glycine at amino acid residue 137 (EU numbering); an asparagine at amino acid residue 203 (EU numbering); a lysine at amino acid residue 274 (EU numbering); an arginine at amino acid residue 355 (EU numbering); or a glutamine at amino acid residue 419 (EU numbering).

15. The antibody or antigen binding fragment thereof of claim 11, wherein the antibody comprises:
    a lysine at amino acid residue 274 (EU numbering), an arginine at amino acid residue 355, and a glutamine at amino acid residue 419 (EU numbering).

16. The antibody or antigen binding fragment thereof of claim 12, wherein the antibody comprises:
    a lysine at amino acid residue 274 (EU numbering), an arginine at amino acid residue 355, and a glutamine at amino acid residue 419 (EU numbering).

17. The antibody or antigen binding fragment thereof of claim 11, wherein the antibody comprises:
    a glycine at amino acid residue 137 (EU numbering), an asparagine at amino acid residue 203 (EU numbering), a lysine at amino acid residue 274 (EU numbering), an arginine at amino acid residue 355, and a glutamine at amino acid residue 419 (EU numbering).

18. The antibody or antigen binding fragment thereof of claim 12, wherein the antibody comprises:
    a glycine at amino acid residue 137 (EU numbering), an asparagine at amino acid residue 203 (EU numbering), a lysine at amino acid residue 274 (EU numbering), an arginine at amino acid residue 355, and a glutamine at amino acid residue 419 (EU numbering).

19. An antibody or antigen binding fragment thereof that specifically binds human IL-4Rα, wherein the antibody comprises a heavy chain variable region (VH) and a light chain variable region (VL), wherein the VH comprises heavy chain complementarity determining regions HCDR1, HCDR2, and HCDR3, and the VL comprises light chain complementarity determining regions LCDR1, LCDR2, and LCDR3, wherein:
    the HCDR1 comprises SEQ ID NO: 19;
    the HCDR2 comprises SEQ ID NO: 20;
    the HCDR3 comprises SEQ ID NO: 3;
    the LCDR1 comprises SEQ ID NO: 22;
    the LCDR2 comprises SEQ ID NO: 5; and
    the LCDR3 comprises SEQ ID NO: 24.

20. The antibody or antigen binding fragment thereof of claim 19, wherein the VH comprises SEQ ID NO: 25 and the VL comprises SEQ ID NO: 26.

21. The antibody or antigen binding fragment thereof of claim 19, wherein the antibody comprises a HC comprising SEQ ID NO: 27 and a LC comprising SEQ ID NO: 28.

22. The antibody or antigen binding fragment thereof of claim 1, wherein the antibody comprises:
    a cysteine at amino acid residue 124 (EU numbering);
    a cysteine at amino acid residue 378 (EU numbering); or
    a cysteine at amino acid residue 124 (EU numbering) and cysteine at amino acid residue 378 (EU numbering).

23. The antibody or antigen binding fragment thereof of claim 3, wherein the antibody comprises:
    a cysteine at amino acid residue 124 (EU numbering);
    a cysteine at amino acid residue 378 (EU numbering); or
    a cysteine at amino acid residue 124 (EU numbering) and cysteine at amino acid residue 378 (EU numbering).

24. The antibody or antigen binding fragment thereof of claim 19, wherein the antibody comprises:
    a cysteine at amino acid residue 124 (EU numbering);
    a cysteine at amino acid residue 378 (EU numbering); or
    a cysteine at amino acid residue 124 (EU numbering) and cysteine at amino acid residue 378 (EU numbering).

25. The antibody or antigen binding fragment thereof of claim 1, wherein the antibody inhibits binding of human IL-4 to human IL-4Rα.

26. The antibody or antigen binding fragment thereof of claim 3, wherein the antibody inhibits binding of human IL-4 to human IL-4Rα.

27. The antibody or antigen binding fragment thereof of claim 19, wherein the antibody inhibits binding of human IL-4 to human IL-4Rα.

28. The antibody or antigen binding fragment thereof of claim 1, wherein the antibody inhibits binding of human IL-13 to human IL-4Rα.

29. The antibody or antigen binding fragment thereof of claim 3, wherein the antibody inhibits binding of human IL-13 to human IL-4Rα.

30. The antibody or antigen binding fragment thereof of claim 19, wherein the antibody inhibits binding of human IL-13 to human IL-4Rα.

31. A nucleic acid comprising a sequence encoding SEQ ID NO: 9, 10, 13, 27, 28, 31, 33, 35, 37, 46, 47, 50, or 52.

32. A vector comprising the nucleic acid of claim 31.

33. The vector of claim 32, wherein the vector comprises a first nucleic acid sequence encoding SEQ ID NO: 9, 13, 31, 33, 35, 37, 46, 50, or 52 and a second nucleic acid sequence encoding SEQ ID NO: 10 or 47.

34. The vector of claim 32, wherein the vector comprises a first nucleic acid sequence encoding SEQ ID NO: 27, and a second nucleic acid sequence encoding SEQ ID NO: 28.

35. A composition comprising a first vector comprising a nucleic acid sequence encoding SEQ ID NO: 9, 13, 31, 33, 35, 37, 46, 50, or 52 and a second vector comprising a nucleic acid sequence encoding SEQ ID NO: 10 or 47.

36. A composition comprising a first vector comprising a nucleic acid sequence encoding SEQ ID NO: 27, and a second vector comprising a nucleic acid sequence encoding SEQ ID NO: 28.

37. A cell comprising the vector of claim 32.

38. A cell comprising the vector of claim 33.

39. A cell comprising the vector of claim 34.

40. The cell of claim 37, wherein the cell is a mammalian cell.

41. The cell of claim 38, wherein the cell is a mammalian cell.

42. The cell of claim 39, wherein the cell is a mammalian cell.

43. A process of producing an antibody or antigen binding fragment thereof comprising culturing the cell of claim 37, under conditions such that the antibody is expressed and recovering the expressed antibody from the culture medium.

44. A process of producing an antibody or antigen binding fragment thereof comprising culturing the cell of claim 38, under conditions such that the antibody is expressed and recovering the expressed antibody from the culture medium.

45. A process of producing an antibody or antigen binding fragment thereof comprising culturing the cell of claim 39, under conditions such that the antibody is expressed and recovering the expressed antibody from the culture medium.

46. An antibody or antigen binding fragment thereof produced by the process of claim 43.

47. An antibody or antigen binding fragment thereof produced by the process of claim 44.

48. An antibody or antigen binding fragment thereof produced by the process of claim 45.

49. An antibody drug conjugate comprising the antibody of claim 1.

50. An antibody drug conjugate comprising the antibody of claim 3.

51. An antibody drug conjugate comprising the antibody of claim 19.

52. A pharmaceutical composition comprising the antibody or antigen binding fragment thereof of claim 1, and a pharmaceutically acceptable excipient, diluent, or carrier.

53. A pharmaceutical composition comprising the antibody or antigen binding fragment thereof of claim 3, and a pharmaceutically acceptable excipient, diluent, or carrier.

54. A pharmaceutical composition comprising the antibody or antigen binding fragment thereof of claim 19, and a pharmaceutically acceptable excipient, diluent, or carrier.

55. A method of treating an IL-4R associated disorder, in a subject in need thereof, comprising administering to the subject a therapeutically effective amount of the antibody or antigen binding fragment thereof of claim 1.

56. A method of treating an IL-4R associated disorder, in a subject in need thereof, comprising administering to the subject a therapeutically effective amount of the antibody or antigen binding fragment thereof of claim 3.

57. A method of treating an IL-4R associated disorder, in a subject in need thereof, comprising administering to the subject a therapeutically effective amount of the antibody or antigen binding fragment thereof of claim 19.

58. The method of claim 55, wherein IL-4R associated disorder is an immune inflammatory disorder.

59. The method of claim 56, wherein IL-4R associated disorder is an immune inflammatory disorder.

60. The method of claim 57, wherein IL-4R associated disorder is an immune inflammatory disorder.

61. The method of claim 58, wherein the immune inflammatory disorder is a Type 2 inflammatory disorder.

62. The method of claim 59, wherein the immune inflammatory disorder is a Type 2 inflammatory disorder.

63. The method of claim 60, wherein the immune inflammatory disorder is a Type 2 inflammatory disorder.

64. The method of claim 61, wherein the Type 2 inflammatory disorder is selected from atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU).

65. The method of claim 62, wherein the Type 2 inflammatory disorder is selected from atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU).

66. The method of claim 63, wherein the Type 2 inflammatory disorder is selected from atopic dermatitis, eosinophilic esophagitis, nasal polyposis, asthma, chronic rhinosinusitis (CRS), allergic disease, chronic obstructive pulmonary disease (COPD), or chronic spontaneous urticaria (CSU).

67. The method of claim 55, wherein the IL-4R associated disorder is cancer.

68. The method of claim 56, wherein the IL-4R associated disorder is cancer.

69. The method of claim 57, wherein the IL-4R associated disorder is cancer.

* * * * *